(12) United States Patent
Vehniäinen et al.

(10) Patent No.: US 10,808,024 B2
(45) Date of Patent: Oct. 20, 2020

(54) ANTIBODIES AGAINST IMMUNOCOMPLEXES COMPRISING CYANOBACTERIAL CYCLIC PEPTIDE HEPATOTOXINS

(71) Applicant: TURUN YLIOPISTO, Turun yliopisto (FI)

(72) Inventors: Markus Vehniäinen, Littoinen (FI); Urpo Lamminmäki, Vanhalinna (FI); Sultana Akter, Turku (FI)

(73) Assignee: TURUN YLIOPISTO, Turun Yliopisto (FI)

( * ) Notice: Subject to any disclaimer, the term of this patent is extended or adjusted under 35 U.S.C. 154(b) by 0 days.

(21) Appl. No.: 16/064,790

(22) PCT Filed: Dec. 21, 2016

(86) PCT No.: PCT/FI2016/050911
§ 371 (c)(1),
(2) Date: Jun. 21, 2018

(87) PCT Pub. No.: WO2017/109290
PCT Pub. Date: Jun. 29, 2017

(65) Prior Publication Data
US 2019/0010218 A1 Jan. 10, 2019

(30) Foreign Application Priority Data
Dec. 21, 2015 (FI) .................................... 20155980

(51) Int. Cl.
| | | |
|---|---|---|
| *A61K 39/395* | (2006.01) | |
| *C07K 16/12* | (2006.01) | |
| *C07K 16/44* | (2006.01) | |
| *G01N 33/543* | (2006.01) | |
| *C07K 16/00* | (2006.01) | |
| *C12N 15/62* | (2006.01) | |
| *C12N 15/85* | (2006.01) | |
| *G01N 33/564* | (2006.01) | |
| *G01N 33/569* | (2006.01) | |

(52) U.S. Cl.
CPC ............ *C07K 16/12* (2013.01); *C07K 16/005* (2013.01); *C07K 16/44* (2013.01); *C12N 15/62* (2013.01); *C12N 15/85* (2013.01); *G01N 33/54306* (2013.01); *G01N 33/564* (2013.01); *G01N 33/56911* (2013.01); *C07K 2317/33* (2013.01); *C07K 2317/622* (2013.01); *G01N 2333/195* (2013.01)

(58) Field of Classification Search
CPC .................................................... C07K 16/12
See application file for complete search history.

(56) References Cited

FOREIGN PATENT DOCUMENTS

| EP | 2759551 A1 | 7/2014 |
|---|---|---|
| JP | 2000055917 A | 2/2000 |
| WO | 01-18059 A2 | 3/2001 |
| WO | 2004046733 A1 | 6/2004 |

OTHER PUBLICATIONS

S. Nagata et al., "A New Type Sandwich Immunoassay for Microcystin: Production of Monoclonal Antibodies Specific to the Immune Complex Formed by Microcystin and an Anti-microcystin Monoclonal Antibody", Natural Toxins, 1999, pp. 49-55, vol. 7.
J. McElhiney et al., "Rapid Isolation of a Single-Chain Antibody against the Cyanobacterial Toxin Microcystin-LR by Phage Display and Its Use in the Immunoaffinity Concentration of Microcystins from Water", Applied and Environmental Microbiology, Nov. 2002, pp. 5288-5295, vol. 68, No. 11.
N. Khreich et al., "A highly sensitive competitive enzyme immunoassay of broad specificity quantifying microcystins and nodularins in water samples", Toxicon, Jan. 14, 2009, pp. 551-559, vol. 53.
M. Niemi et al., "A Structural Insight into the Molecular Recognition of a (-)-Δ9-Tetrahydrocannabinol and the Development of a Sensitive, One-Step, Homogeneous Immunocomplex-Based Assay for Its Detection", JMB, May 26, 2010, pp. 803-814, vol. 400.
S. Akter et al., "Broad-Spectrum Noncompetitive Immunocomplex Immunoassay for Cyanobacterial Peptide Hepatotoxins {Microcystins and Nodularins)", Analytical Chemistry, 2016, pp. 10080-10087, vol. 88.
M. Weller, "Immunoassays and Biosensors for the Detection of Cyanobacterial Toxins in Water", Sensors, 2013, pp. 15085-15112, vol. 13.
T. Tsutsumi et al., "Development and Application of Highly Sensitive Anti-immune Complex ELISAs for Microcystins in Tap Water", Food and Agricultural Immunology, 2000, pp. 231-241, vol. 12.
T. Huovinen et al., "Two Scfv antibody libraries derived from identical VL-VH framework with different binding site designs display distinct binding profiles", Protein Engineering, Design & Selection, Aug. 11, 2013, pp. 683-693, vol. 26, No. 10.
E. Brockmann et al., "Synthetic single-framework antibody library integrated with rapid affinity maturation by VL shuffling", Protein Engineering, Design & Selection, Jun. 16, 2011, pp. 691-700, vol. 24, No. 9.
A. Krebber et al., "Reliable cloning of functional antibody variable domains from hybridomas and spleen cell repertoires employing a reengineered phage display system", Journal of Immunological Methods, 1997, pp. 35-55, vol. 201.

(Continued)

*Primary Examiner* — Albert M Navarro
(74) *Attorney, Agent, or Firm* — Buchanan Ingersoll & Rooney PC

(57) ABSTRACT

The present invention relates to means and methods for detecting cyanobacterial cyclic peptide hepatotoxins (CCPH) in aqueous samples. More specifically, the invention provides recombinant anti-immunocomplex (anti-IC) antibodies which bind to immunocomplexes formed between one or more CCPH variants and an anti-CCPH primary antibody, and immunoassays, preferably non-competitive immunoassays, employing the same.

42 Claims, 18 Drawing Sheets

Specification includes a Sequence Listing.

(56) References Cited

OTHER PUBLICATIONS

J. Meriluoto et al., "Toxic Cyanobacterial Monitoring and Cyanotoxin analysis", Abo Akademis Förlag—Åbo Akademi University Press, 2005, vol. 65, No. 1 (164 pages).

H. Hautala et al., "Quantitative PCR detection and improved sample preparation of microcystin-producing Anabaena, Microcystis and Planktothrix", Ecotoxicology and Environmental Safety, 2013, pp. 49-56, vol. 87.

Office Action and Search Report dated May 20, 2016, by the Finnish Patent Office in corresponding Finnish Patent Application No. 20155980. (12 pages).

| A | B | C | | D | E | F | G | H | I | J | K | X | Y |
|---|---|---|---|---|---|---|---|---|---|---|---|---|---|
| LR | dmLR | RR | | dmRR | LA | LY | LF | LW | YR | WR | Nodularin-R | no CCPH, no ADDA Mab | no CCPH, with ADDA Mab |
| | | | | Microcystins (MC) | | | | | | | | | |

Figure 12

| A | B | C | D | E | F | G | H | I | J | K | X | Y |
|---|---|---|---|---|---|---|---|---|---|---|---|---|
| LR | dmLR | RR | dmRR | LA | LY | LF | LW | YR | WR | Nodularin-R | no CCPH, no ADDA Mab | no CCPH, with ADDA Mab |
| | | | Microcystins (MC) | | | | | | | | | |

Figure 12 cont.

| A | B | C | D | E | F | G | H | I | J | K | X | Y |
|---|---|---|---|---|---|---|---|---|---|---|---|---|
| LR | dmLR | RR | dmRR | LA | LY | LF | LW | YR | WR | Nodularin-R | no CCPH, no ADDA Mab | no CCPH, with ADDA Mab |
| Microcystins (MC) | | | | | | | | | | | | |

Figure 12 cont.

ANTIBODIES AGAINST IMMUNOCOMPLEXES COMPRISING CYANOBACTERIAL CYCLIC PEPTIDE HEPATOTOXINS

FIELD OF THE INVENTION

The present invention relates to means and methods for detecting cyanobacterial cyclic peptide hepatotoxins (CCPH) in aqueous samples. More specifically, the invention relates to anti-immunocomplex (anti-IC) antibodies which bind to immunocomplexes formed between one or more different CCPH variants and an anti-CCPH primary antibody, and immunoassays, preferably non-competitive immunoassays, employing the same. The invention also relates to uses of and kits comprising said anti-IC antibodies, as well as to polynucleotides encoding said anti-IC antibodies, vectors comprising said polynucleotides, and isolated host cells comprising said vectors. The invention also relates to a method for the preparation of the present anti-IC antibodies.

BACKGROUND OF THE INVENTION

Cyanobacteria, also known as blue-green algae, are ancient photosynthetic prokaryotes that have an essential role in ecosystems as primary producers and nitrogen fixers. Cyanobacteria produce hundreds of bioactive compounds which are often either small cyclic peptides with a multitude of enzyme inhibition capacities or diverse alkaloids with neurotoxic or cytotoxic properties. Some of their bioactive substances have pharmaceutical potential but many of them can be classified as potent mammalian biotoxins.

The most frequently reported cyanotoxins are cyclic heptapeptide hepatotoxins, microcystins, found in some species of the freshwater cyanobacteria. Microcystins form a class of over 90 analogues. Although relatively few cyanobacterial genera produce microcystins, the main producer organisms are unfortunately among the most common cyanobacteria world-wide: *Microcystis, Anabaena*, and *Planktothrix*. Related hepatotoxic pentapeptides, nodularins, have been detected in the brackish water cyanobacterium *Nodularia*. Most microcystins and nodularins are potent hepatotoxins (liver toxins) with an acute LD50 value of 50-600 µg/kg (mouse, i.p.). Besides acute toxicity, microcystins and nodularins are tumor promoters and possible carcinogens. The molecular basis of microcystin/nodularin toxicity is the inhibition of protein phosphatases 1 and 2A. Human fatalities clearly related to microcystins have been reported in the context of haemodialysis treatment with toxin-containing water. In addition, epidemiological evidence points to increased prevalence of liver cancer in populations exposed to microcystins.

Cyanobacteria commonly form mass occurrences in fresh and brackish waters worldwide. Such blooms are often toxic, causing animal poisonings and posing a risk to human health. Problems with cyanobacterial toxins arise from the use of surface water for preparation of drinking water and for recreation. There are no morphological markers which differentiate toxic and non-toxic cyanobacterial strains. Thus, visual testing is insufficient.

Current analytical methods for cyanotoxins include competitive immunoassays, enzyme based protein phosphatase inhibition assays (PPIAs) and chromatographical methods including high performance liquid chromatography (HPLC) with different detectors like UV absorbance, fluorescence or mass spectrometry (MS). PPIA is not unfortunately specific to only MCs, and LC-methods are poorly suited for preliminary screening purposes due to their complexity and limited number of available reference material for toxin variants. Competitive immunoassays are usually based on antibodies which are obtained with MC-LR immunization and thus have limited capability of recognizing multiple MC and Nod variants equally. Better coverage can be obtained when the Adda-group, present in all MCs/Nods, is specifically targeted (WO 01/18059). However, competitive immunoassays in general suffer from lower overall sensitivity and specificity than non-competitive assay formats.

The development of secondary antibodies for the non-competitive assay formats is very difficult due to the small size of the antigen, especially using traditional methods based on immunization. One means to produce antibodies for the detection of small analytes is disclosed in WO 2004/046733, describing a method of producing antibodies that bind to an immunocomplex between a primary antibody and its specific analyte but which do not to significant extent bind the primary antibody or the analyte alone. The method is based on obtaining the immunocomplex-binding antibody by selecting it from a display recombinant binding partner library. A different approach for the same but using animal immunization instead of recombinant binding partner library has been described by Nagata et al. (Nat. Toxins 7:49-55, 1999). Nagata et al. managed to produce three mAbs partly specific to the immunocomplex formed by MC-LR and an anti-MC-LR mAb and disclosed a non-competitive ELISA assay employing the same. However, due to the poor performance characteristics of the immunocomplex-binding antibodies, the assay requires one, or even two overnight incubations, for instance, and is therefore unacceptably slow from the practical point of view. They also show that their anti-IC antibody has affinity towards the primary antibody without CCPH, which explains the need for overnight incubations in their immunoassay.

Thus, there is a need for rapid, simple, and sensitive antibodies suitable for high-throughput first-line screening of cyanobacterial hepatotoxins, both in field and laboratory conditions.

BRIEF DESCRIPTION OF THE INVENTION

In one aspect the invention proves an antibody binding to an immunocomplex formed by a cyanobacterial cyclic peptide hepatotoxin (CCPH) and an antibody generated using an immunogen comprising a carrier and a compound of formula (I)

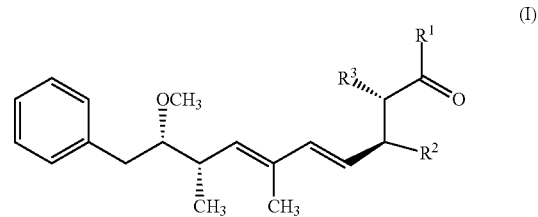

wherein $R^1$ is a halogen atom, $-OSO_3$, $-OR'$ or $-NR'R''$,

R' is hydrogen, substituted or unsubstituted $(C_1-C_4)$alkyl or $(C_1-C_4)$acyl, when bound to nitrogen, R" is hydrogen, substituted or unsubstituted (C1-C4)alkyl or (C1-C4)acyl, when bound to nitrogen, $R^2$ is hydrogen, $(C_1-C_4)$alkyl, $(C_1-C_4)$alkoxy, $(C_1-C_4)$acyl, $(C_1-C_4)$aminoacyl or $(C_1-C_4)$carboxyaminoacyl, or $R^1$ and $R^2$ are connected to each other to form a cyclic moiety, $R^3$ is hydrogen or $(C_1-C_4)$alkyl, and wherein the phenyl group may be substituted or unsubstituted.

Some embodiments provide group-specific antibodies which recognize at least CCPH variants MC-LR, MC-dmLR, MC-LA, MC-RR, MC-dmRR, MC-YR, MC-LY, MC-LF, MC-LW, MC-WR and Nod-R. Preferred antibodies include those that comprise light chain variable region comprising CDRs 1-3 having at least 80% sequence identity with CDRs 1-3 set forth in SEQ ID NOs: 5 or 6, and a respective heavy light chain variable region comprising CDRs 1-3 having at least 80% sequence identity with CDRs 1-3 set forth in SEQ ID NOs: 30 or 31. Further preferred group-specific antibodies comprise a light chain variable region having at least 80% sequence identity with SEQ ID NO: 5, and a heavy chain variable region having at least 80% sequence identity with SEQ ID NO: 30; a light chain variable region having at least 80% sequence identity with SEQ ID NO: 6, and a heavy chain variable region having at least 80% sequence identity with SEQ ID NO: 31.

Some other embodiments provide subgroup-specific antibodies, preferably those comprising a light chain variable region comprising CDRs 1-3 having at least 80% sequence identity with CDRs 1-3 set forth in a sequence selected from the group consisting of SEQ ID NOs: 15-29; and a respective heavy light chain variable region comprising CDRs 1-3 having at least 80% sequence identity with CDRs 1-3 set forth in a sequence selected from the group consisting of SEQ ID NOs: 40-55. Further preferred subgroup-specific antibodies include those comprising a light chain variable region comprising an amino acid sequence having at least 80% sequence identity with an amino sequence selected from the group consisting of SEQ ID NOs: 15-29; and a respective heavy light chain variable region comprising an amino acid sequence having at least 80% sequence identity with an amino acid sequence selected from the group consisting of SEQ ID NOs: 40-55.

Furthermore, some other embodiments provide variant-specific antibodies comprising a light chain variable region comprising CDRs 1-3 having at least 80% sequence identity with CDRs 1-3 set forth in a sequence selected from the group consisting of SEQ ID NOs: 7-14; and a respective heavy light chain variable region comprising CDRs 1-3 having at least 80% sequence identity with CDRs 1-3 set forth in a sequence selected from the group consisting of SEQ ID NOs: 32-39. Still further variant specific antibodies include those comprising a light chain variable region comprising an amino acid sequence having at least 80% sequence identity with an amino sequence selected from the group consisting of SEQ ID NOs: 7-14; and a respective heavy light chain variable region comprising an amino acid sequence having at least 80% sequence identity with an amino acid sequence selected from the group consisting of SEQ ID NOs: 32-39.

Other aspects of the invention provide different sets of the present antibodies.

Also provided is a method for the preparation of the present antibodies. The method comprises obtaining the antibody from a recombinant expression library by selecting an antibody that binds to an immunocomplex of a CCPH and an primary antibody generated using an immunogen comprising a carrier and a compound of formula (I) set forth above. Antibodies obtained by such a method are also provided and may be used in the same manner as the antibodies disclosed above, or comprised in a set of antibodies.

In some further aspects, provided herein are a polynucleotide encoding an anti-IC antibody according to the present invention, an expression vector comprising said polynucleotide, and an isolated host cell or in vitro expression system comprising said vector.

In a still further aspect, the present invention provides an immunoassay for detecting one or more CCPH variants in an aqueous sample, comprising a) reacting the sample with a set of antibodies comprising at least one anti-IC antibody and an anti-CCPH primary antibody, wherein said anti-CCPH primary antibody binds to the one or more CCPH variants present in the sample, if any, and forms an immunocomplex therewith, and wherein said at least one anti-IC antibody binds to said immunocomplex forming a sandwiched immunocomplex; and b) detecting the presence or absence of said sandwiched immunocomplex indicating the presence or absence of said one or more CCPH variants in said sample, respectively.

In an even further aspect, provided herein is use of an anti-IC antibody or a set of anti-IC antibodies according to the present invention for detecting the presence or absence of one or more CCPH variants in an aqueous sample.

In a yet further aspect, provided herein is a kit for use in detecting one or more CCPH variants in an aqueous sample, comprising at least one anti-IC antibody or a set of anti-IC antibodies according to the present invention.

Other objectives, aspects, embodiments, details and advantages of the present invention will become apparent from the following figures, detailed description, examples, and dependent claims.

BRIEF DESCRIPTION OF THE DRAWINGS

In the following the invention will be described in greater detail by means of preferred embodiments with reference to the attached drawings, in which FIG. 1A shows structure of MC variants (above) and Nod-R (below) used in this study. Commonly found variations at positions X, Z, and R are described. Uncommon amino acid with ADDA side chain is present in both MCs and Nods.

FIG. 4 shows single-step TR-IFMA non-competitive immunoassay using SA51D1 as a secondary antibody for recognizing the IC. Figure presents the standard curves for eleven different CCPH variants in 1 h assay. Each point is average signal of four replicates. Error bars representing the standard deviation are also shown. The average blank signal with no toxin was 381 counts per second (cps) and blank+ 3SD was 555 cps. The sensitivity varies from 0.0108 µg/L (MC-LR) to 0.05 µg/L (MC-LA) for the tested toxin variants.

DETAILED DESCRIPTION OF THE INVENTION

Figure 1B:
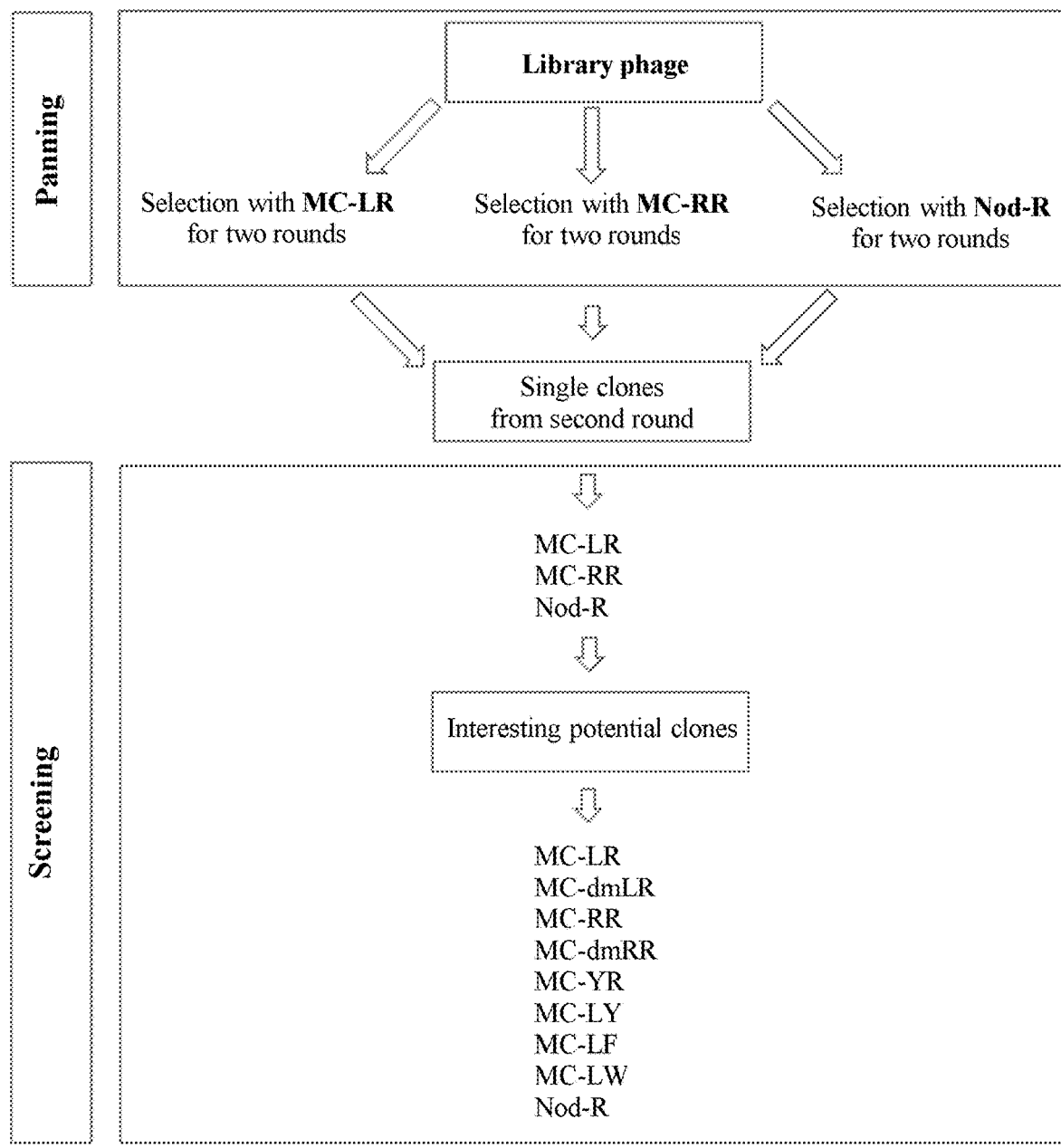
FIG. 1B illustrates the panning and screening scheme for isolation of the anti-IC binders specific to different MCs and Nods. Two rounds of phage display selections were done using a single CCPH variant (either MC-LR, MC-RR or Nod-R). Single clones, expressed as ScFv-AP in E. coli, from each of the second panning round were screened with MC-LR, MC-RR and Nod-R. Several clones were further tested with different CCPHs shown in FIG. 1A.

The present invention provides an anti-immunocomplex (anti-IC) antibody which binds to an immune complex between a cyanobacterial cyclic peptide hepatotoxin and a primary antibody recognizing the same.

As used herein, the singular forms "a," "an," and "the" include the plurals unless the context clearly dictates otherwise.

As used herein, the term "cyanobacterial cyclic peptide hepatotoxin" (CCPH) refers to at least one liver toxin selected from the group consisting of cyclic heptapeptides (microcystins) and pentapeptides (nodularins) produced by cyanobacteria. Microcystins (MC) form a class of over 90 variants with differing toxicities, produced by some species of the freshwater cyanobacteria. MC-LR, the most studied and widely distributed variant is considered to be the most toxic variant. Nodularins (Nod) form a class of about 10 variants and they have been detected in the brackish water cyanobacterium *Nodularia* and in the marine sponge *Theonella swinhoei*. Besides acute toxicity, microcystins and nodularins are tumor promoters and possible carcinogens.

As used herein, the term "antibody" refers to an immunoglobulin structure comprising two heavy (H) chains and two light (L) chains interconnected by disulfide bonds. The heavy and light chains are both comprised of a variable region (abbreviated herein as $V_H$ and $V_L$, respectively) and a constant region (abbreviated herein as $C_H$ and $C_L$, respectively). The $C_H$ region is further comprised of three domains, $C_{H1}$, $C_{H2}$ and $C_{H3}$. The $V_H$ and $V_L$ regions are composed of regions of hypervariability, termed complementarity determining regions (CDR), interspersed with regions that are more conserved, termed framework regions (FR). Each $V_H$ and $V_L$ is composed of three CDRs (HCRDs 1-3 and LCDRs 1-3, respectively) and four FRs (HFRs 1-4 and LFRs 1-4, respectively), arranged from amino-terminus to carboxy-terminus in the order of FR1, CDR1, FR2, CDR2, FR3, CDR3, FR4. Herein, the CDRs are identified by the Kabat numbering scheme.

Antibodies can exist as intact immunoglobulins or as any of a number of well-characterized antigen-binding fragments or single chain variants thereof, all of which are herein encompassed by the term "antibody". Said fragments and variants may be produced by recombinant DNA techniques, or by enzymatic or chemical separation of intact immunoglobulins as is well known in the art. The term "antibody" also includes, but is not limited to, polyclonal, monoclonal, and recombinant antibodies of isotype classes IgA, IgD, IgE, IgG, and IgM and subtypes thereof.

As used herein, the term "Fab fragment" refers to a monomeric antigen-biding fragment of an antibody that consists of the $V_L$, $V_H$, $C_L$ and $C_{H1}$ domains.

As used herein, the term "Fab' fragment" refers to an antigen-biding fragment of an antibody that is essentially a Fab fragment with part of the hinge region.

As used herein, the term "F(ab')$_2$ fragment" refers to a dimeric antigen-biding fragment of an antibody that comprises two Fab' fragments linked by a disulfide bridge at the hinge region.

As used herein, the term "Fv fragment" refers to a monomeric antigen-biding fragment of an antibody that consists of the $V_L$, and $V_H$ domains.

As used herein, the term "single-chain variable fragment" (scFv) refers to an antigen-biding fragment of an antibody that is a recombinant polypeptide in which a $V_L$ and $V_H$ are joined together by a linker, such as a peptide linker. In a particular non-limiting embodiment, said linker comprises an amino acid sequence of SEQ ID NO:1 or a conservative sequence variant thereof. Also encompassed are scFvs comprising a linker having at least 80%, 85%, 90%, 91%, 92%, 93%, 94%, 95%, 96%, 97%, 98%, or 99% sequence identity with SEQ ID NO:1, provided that the scFvs retain their specificity. Other possible linker peptides are available in the art, and a skilled person can easily test whether or not a given linker peptide is suitable for use in the present svFcs.

As used herein, the terms "nanobody" or "VHH" refer to the monomeric variable domains of camelid heavy chain antibodies.

As used herein, the term "independent variable domain" refers to the monomeric variable domain of antibody.

As used herein, the terms "darpin", "affibody", "monobody" refer to the engineered recombinant protein scaffold based binders derived from the ankyrinrepeat proteins, the 10th domain of type 3 fibronectin, or *Staphylococcus aureus* Protein A, respectively. Other type of recombinant protein scaffolds and binders derived from these are well known in the art.

As used herein, the term "recombinant expression library" refers to in-a-heterologous-host- or in vitro-expressed repertoire of antibodies or that of binders based on other recombinant protein scaffold. The number of different antibodies or other type of binders in such a library is typically >1E6, more preferably >1E7, even more preferably >1E8, even more preferably >1E9, and most preferably >1E10.

As used herein, the term "group-specific antibody" refers to an antibody that selectively binds all or substantially all members of a group of related polypeptides, such as CCPHs, or immunocomplexes thereof, and does not selectively bind polypeptides or immunocomplexes outside the group of said related polypeptides or immunocomplexes. The term "group-specific" is herein interchangeable with the term "generic".

As used herein, the term "subgroup-specific antibody" refers to an antibody that selectively binds substantially all members of a subgroup of related polypeptides, such as MCs, MC-LZs, MC-XRs, XRs, or Nods, or immunocomplexes thereof, and does not selectively bind polypeptides or immunocomplexes outside the subgroup of said related polypeptides or immunocomplexes. The term "subgroup-specific" is herein interchangeable with the term "subgeneric".

As used herein, the term "primary antibody" refers to an antibody that specifically binds to an analyte of interest. In some specific embodiments, the analyte of interest is at least one type of a CCPH variant and the primary anti-CCPH antibody is an anti-Adda antibody which specifically binds to an Adda-group present in all MCs/Nods. Owing to their broad specificity, anti-Adda antibodies may be called as antibodies group-specific for cyanobacterial cyclic peptide hepatotoxins. A preferred primary antibody is a monoclonal Adda-specific antibody, such as AD4G2 made commercially available by Enzo Life Sciences, Inc. (USA), or any biosimilar or antigen-binding fragment thereof.

According to some embodiments, the primary antibody may have been generated using an immunogen comprising a carrier and a compound of formula (I)

wherein
$R^1$ is a halogen atom, —OSO$_3$, —OR' or —NR'R",
R' is hydrogen, substituted or unsubstituted (C$_1$-C4)alkyl or (C$_1$-C$_4$)acyl, when bound to nitrogen,
R" is hydrogen, substituted or unsubstituted (C$_1$-C4)alkyl or (C$_1$-C$_4$)acyl, when bound to nitrogen,
$R^2$ is hydrogen, (C$_1$-C$_4$)alkyl, (C$_1$-C$_4$)alkoxy, (C$_1$-C$_4$)acyl, (C$_1$-C$_4$)aminoacyl or (C$_1$-C$_4$)carboxyaminoacyl,
or $R^1$ and $R^2$ are connected to each other to form a cyclic moiety,
$R^3$ is hydrogen or (C$_1$-C$_4$)alkyl, and
wherein the phenyl group may be substituted or unsubstituted.

In some preferred embodiments, $R^1$ is Br.
In some further preferred embodiments, $R^3$ is methyl.
In some further embodiments, $R^1$ is aminoacyl and $R^2$ is (C$_1$-C$_4$)acyl, or group $R^1$ is glycyl or D-alanyl, and $R^2$ is acetyl, or $R^1$ is NH$_2$ and group $R^2$ is glutamidyl or 2-aminoproprionamidyl.

Alternatively, the primary antibody may have been generated using an immunogen comprising a carrier and a compound of formula (II)

wherein R is a linear or branched linker comprising 3 to 50, preferably 3 to 30, more preferably 3 to 20, even more preferably 3 to 15 atoms selected from the group consisting of C, N, S, P, O, H, and halogen, and any combinations thereof.

Suitable carries comprised in the immunogen include, but are not limited to, keyhole limpet hemocyanin, bovine serum albumin, ovalbumin, cationised bovine serum albumin and horseradish peroxidase.

As used herein, the term "an antibody generated using an immunogen" encompasses polyclonal and monoclonal antibodies obtained by traditional animal immunization, as well as any recombinant versions thereof.

For generation of the primary antibody against wide class of molecules like CCPH's, a carefully selected immunization strategy is important. Immunization using immunogen comprising a generic substructure of the analyte molecule, Adda ((2S,3S,8S,9S)-3-amino-9-methoxy-2,6,8-trimethyl-10-phenyldeca-4(E),6(E)-dienoic acid), is used to achieve class selectivity. Molecules presenting the generic Adda substructure are covalently conjugated to a suitable carrier, such as bovine serum albumin or keyhole limpet hemocyanine, and the conjugate is used to immunize animals such as mouse or rabbit. Equally important can be to use a very short linker, or neglect the linker totally when coupling the hapten to the carrier protein. This can facilitate the generation of primary antibodies that have a deep binding pocket for the common part of CCPH's, the Adda group. When this primary antibody binds the native CCPH from Adda group, the cyclic amino acid moiety of CCPH, together with the closely located parts of the primary antibody itself, are presenting a new epitope on surface of immunocomplex, that is available for generating secondary antibodies. Using different CCPH's to form the immunocomplex with anti-Adda antibody, secondary antibodies towards different CCPH's in immunocomplex can be obtained using for example phage display panning with recombinantly expressed antibody library.

As used herein, the term "anti-IC antibody" refers to an antibody that specifically binds to an immunocomplex between a primary antibody and its analyte but does not to a significant extent bind the primary antibody or the analyte alone. The anti-IC antibody may also be called as a secondary antibody.

As used herein, the term "conservative sequence variant" refers to an amino acid sequence comprising modifications which do not significantly alter the binding properties or specificities of the antibody in question. Conservative amino acid sequence variants include variants arising from amino acid substitutions with similar amino acids. As is well known in the art, said similarity may be determined on the basis of similarity in polarity, charge, solubility, hydrophobicity, hydrophilicity, and/or the amphipathic nature of the residues involved. For example, nonpolar (hydrophobic) amino acids include alanine (Ala, A), leucine (Leu, L), isoleucine (Ile, I), valine (Val, V), proline (Pro, P), phenylalanine (Phe, F), tryptophan (Trp, W), and methionine (Met, M); polar neutral amino acids include glycine (Gly, G), serine (Ser, S), threonine (Thr, T), cysteine (Cys, C), tyrosine (Tyr, Y), asparagine (Asn, N), and glutamine (Gln, Q); positively charged (basic) amino acids include arginine (Arg, R), lysine (Lys, K), and histidine (His, H); and negatively charged (acidic) amino acids include aspartic acid (Asp, D) and glutamic acid (Glu, E). Conservative amino acid sequence variants also include variants comprising small amino acid deletions and/or insertions.

As used herein, the percent similarity between two amino acid sequences is equivalent to the percent identity between the two sequences. The percent identity between the two sequences is a function of the number of identical positions shared by the sequences (i.e., % identity=# of identical positions/total # of positions×100), taking into account the number of gaps, and the length of each gap, which need to be introduced for optimal alignment of the two sequences. The comparison of sequences and determination of percent identity between two sequences can be accomplished using standard methods known in the art.

Since traditional animal immunization is a tedious and problematic procedure with low success rate, especially when antibodies against immunocomplexes comprising small analytes are to be raised, the present antibodies are preferably obtained from a recombinant expression library, e.g. by employing a phage display based strategy. Alternatively, other display techniques such as ribosome display, bacterial cell surface display, yeast cell surface display or mammalian cell surface display can be used to isolate the binders from a recombinant expression library. In addition to antibodies or antibody fragments such as Fabs, scFvs, nanobodies or VHHs such libraries can be used to generate binders based on alternative protein scaffolds e.g., darpins, affibodies, monobodies. For example, recombinant expression library enables use of negative selection, where antibodies recognizing the primary antibody are removed before selection with IC. This is not possible with immunization strategy. For instance, anti-IC antibodies may be isolated from a synthetic antibody phage library, such as a scFv or Fab library, using an immunocomplex (IC) panning approach as is well known in the art.

In one aspect, the present invention provides a method for the preparation of anti-IC antibodies disclosed herein. In some embodiments, the method comprises obtaining an anti-IC antibody from a suitable and appropriate recombinant expression library by selecting an antibody that binds to an immunocomplex formed between a CCPH and an anti-CCPH primary antibody, preferably an anti-Adda antibody, or a primary antibody generated using an immunogen comprising a carrier and a compound of formula (I). The method may comprise one or more rounds of selections with or without negative selection steps for excluding antibodies that bind to the primary antibody when not in complex with a CCPH. Preferably, the anti-IC antibody or a fragment thereof is obtained from a phage display library. Accordingly, an expression library may be first preincubated with an immobilized primary antibody to sort out those antibodies binding to the primary antibody as such, whereafter unbound phages are separated and incubated with a mixture of a CCPH and a primary antibody to select those phages that bind to the immunocomplex formed between the immobilized primary antibody and CCPH, but not to the primary antibody as such.

In other words, a method for the preparation of the present anti-IC antibodies may comprises steps of:

a) immobilizing a primary antibody on a solid support or a carrier, such as a microtiter well or a bead, using methods well known in the art;

b) performing a negative selection by reacting the immobilized primary antibody with the library in conditions well known in the art;

c) collecting a first non-bound fraction of the library;

d) contacting the immobilized primary antibody with a CCPH species for forming an immunocomplex between the CCPH species and the primary antibody;

e) reacting the immunocomplex obtained in step d) with the non-bound fraction of the library obtained in step c);

f) removing a second non-bound library by washing in conditions well known in the art;

g) separating and collecting one or more anti-IC antibodies bound to the immunocomplex; and h) expressing said one or more anti-IC antibodies in any suitable expression system.

Typically, the method is repeated two to five times by subjecting the anti-IC antibodies obtained in step g) to repeated rounds of steps b) to g) or to steps d) to g) prior to carrying out step h). The method may also be carried out without the negative selection step b). If desired, different rounds of the method may be carried out using different CCPH species in different rounds of step d). Each phage particle carries genetic information for the recombinant polypeptide that it displays on its surface. This feature allows for identifying DNA encoding a present antibody exhibiting desired specificity by selecting that phage particle which carries it from a potentially very complex phage library. DNA from the best clones may then be isolated, inserted into a suitable expression vector, and transfected or transformed into a compatible expression host to produce the antibody according to standard recombinant technology.

Numerous types of suitable expression vectors are available and include, but are not limited to, plasmids or modified viruses which are maintained in the host cell as autonomous DNA molecules or integrated in genomic DNA. The vector system must be compatible with the host cell employed as is well known in the art. Preferably, DNA encoding an anti-IC antibody according to the present invention is operably linked to one or more heterologous expression control sequences permitting expression of the antibody. Suitable control sequences are readily available in the art and include, but are not limited to, promoter, leader, polyadenylation, and signal sequences.

In some embodiments, it may be desirable to express an anti-IC antibody of the invention as a fusion to one or more peptide or small protein tags that facilitate purification, isolation, immobilization and/or detection. Non-limiting examples of suitable affinity tags for purification or immobilization purposes include polyhistidine tags (His-tags), hemagglutinin tags (HA-tags), glutathione-S-transferase tags (GST-tags), and biotin tags. Suitable detection tags include fluorescent proteins, such as GFP, and enzyme tags that will generate a colored product upon contact with a chromogenic substrate. Non-limiting examples of suitable enzyme tags include alkaline phosphatase (AP), and (horseradish) hydrogen peroxidase (HRP). Also other tags such as biotin, avidin, and streptavidin may be employed for detection purposes. They can be detected with a biotin/avidin/strepstavidin-binding protein that is conjugated to an enzyme, fluorophore or other reporter molecule. Vectors, other means, and methods for producing present anti-IC antibodies as fusion proteins are readily available in the art.

Non-limiting examples of suitable host cells include prokaryotic hosts such as bacteria (e.g. *E. coli*, bacilli), yeast (e.g. *Pichia pastoris, Saccharomyces cerevisae*), and fungi (e.g. filamentous fungi), as well as eukaryotic hosts such as insect cells (e.g. Sf9), and mammalian cells (e.g. CHO cells). In some embodiments, host cells transfected with an expression vector comprising a polynucleotide encoding for an anti-IC antibody of the invention are cultured under conditions suitable for the production of a present anti-IC antibody followed by recovering the antibody obtained.

Expression vectors may be transfected into host cells by standard techniques. As used herein, the term "transfection" refers to a wide variety of techniques commonly used for the introduction of exogenous DNA into a prokaryotic or eukaryotic host cell including, but not limited to, electroporation, nucleofection, sonoporation, magnetofection, heat shock, calcium-phosphate precipitation, DEAE-dextran transfection and the like. As used herein, the term "transfection" and all verbal forms thereof is interchangeable with the term "transformed" and all verbal forms thereof, respectively.

An anti-IC antibody of the invention may also be produced by in vitro protein expression, also known as in vitro translation, cell-free protein expression, cell-free translation, or cell-free protein synthesis. Several cell-free expression systems based on, for instance, bacterial (e.g. *E. coli*), rabbit reticulocyte, CHO, or human lysates are commercially available in the art. In some embodiments, in vitro protein expression may be performed either in batch reactions or in a dialysis mode.

The present invention provides anti-IC antibodies specific for immunocomplexes formed between a CCPH and an anti-CCPH primary antibody, preferably a monoclonal anti-Adda antibody, or a primary antibody generated using an immunogen comprising a carrier and a compound of formula (I). Importantly, the present anti-IC antibodies show no significant binding to the primary antibody or the CCPH as such.

Anti-IC antibodies whose sequences are provided herein all comprise a light chain variable region with CDR1 comprising SEQ ID NO:2, CDR2 comprising SEQ ID NO:3, and CDR3 comprising SEQ ID NO:4. According to an alternative definition, said anti-IC antibodies comprise a light chain variable region, wherein CDR1 comprises amino acids 24-35, CDR2 comprises amino acids 51-57, and CDR3 comprises amino acids 90-98 of an amino acid sequence selected from the group consisting of SEQ ID NOs: 5 to 29. Said anti-IC antibodies comprise respective heavy chain CDR1, CDR2, and CDR3 sequences as indicated in SEQ ID NOs: 30 to 54. Also encompassed are conservative sequence variants and variants having at least 80%, at least 85%, at least 90%, at least 91%, at least 92%, at least 93%, at least 94%, at least 95%, at least 96%, at least 97%, at least 98%, or at least 99% sequence identity with said CDR sequences, provided that the antibodies substantially retain their specificities.

In some embodiments, the present anti-IC antibodies comprise identical framework regions such that LFR1 comprises amino acids 1-23, LFR2 comprises amino acids 36-50, LFR3 comprising amino acids 58-89, and LFR4 comprising amino acids 99-110 of any SEQ ID NO: 5, for instance, and wherein HFR1 comprises amino acids 1-30, HFR2 comprises amino acids 36-49, HFR3 comprises amino acids 67-98, and HFR4 comprises amino acids 111-121 of SEQ ID NO: 31, for instance. However, in some embodiments, one or more of the framework regions may be conservative sequence variants of, or have at least 80%, 85%, 90%, 91%, 92%, 93%, 94%, 95%, 96%, 97%, 98%, or 99% sequence identity with the sequences set forth above, provided that the specificities of the antibodies are not significantly altered. In some further embodiments, the present CDRs may be grafted into a different framework by recombinant techniques, again provided that the specificities of the antibodies are not significantly altered.

In some embodiments, light chain variable regions of the present anti-IC antibodies are as depicted in SEQ ID NOs: 5-29, while their respective heavy chain variable regions are as depicted in SEQ ID Nos: 31-55. Also encompassed are conservative sequence variants and variants having at least 80%, 85%, 90%, 91%, 92%, 93%, 94%, 95%, 96%, 97%, 98%, or 99% sequence identity with said sequences, provided that the antibodies substantially retain their specificities.

Unexpectedly, some of the present anti-IC antibodies, are group-specific, i.e. they recognize immunocomplexes between a number of different, preferably all or substantially all, variants of CCPHs and an anti-CCPH primary antibody, preferably an anti-Adda antibody. This is surprising since these antibodies were obtained by panning of a phage display library only with a single CCPH variant, namely either MC-LR, MC-RR or Nod-R. Nevertheless, these antibodies are specific for at least CCPH variants MC-LR, MC-dmLR, MC-LA, MC-RR, MC-dmRR, MC-YR, MC-LY, MC-LF, MC-LW, MC-WR and Nod-R as demonstrated in the examples. However, specificities of these antibodies are considerably broader than this because they tolerate at least L, R, W or Y at position 2; A, R, Y, F, or W at position 4; and $R^1$ be either methylated or demethylated in the microcystin structure without significant effect in their binding properties. They also tolerate amino acids at positions 1 and 2 be absent, thus enabling recognition of immunocomplexes comprising nodularins.

NO: 6 and a heavy chain variable region comprising SEQ ID NO: 31. Particular non-limiting examples of preferred group-specific anti-1C antibodies include SA51D1 and SA51F6.

Some of the present antibodies are subgeneric although they, too, were panned from a phage display library only with a single CCPH variant, namely either MC-LR, MC-RR or Nod-R. For instance, antibodies SA42E10 and SA52C2 are MC subgroup-specific binders which recognize immunocomplexes of all or substantially all MC variants but not the Nods, whereas antibody SA55D1 is an MC-LZ subgroup-specific binder which recognizes immunocomplexes of MCs having leucine (L) at position 2. Non-limiting examples of variant members of subgroup MC-LZ include MC-LR, dmMC-LR, MC-LY, MC-LF, MC-LA and MC-LW. Furthermore, antibodies SA41A5 and SA51H4, for example, are specific for a subgroup MC-XR, i.e. they recognize immunocomplexes of MCs having arginine (R) at position 4, but not corresponding Nods. Non-limiting General Structure of Microcystin with Amino Acid Numbering Shown Thus, the present group-specific anti-IC antibodies are capable of recognizing eleven or more, for example, fifteen or more, twenty or more, thirty or more, forty or more, fifty or more, sixty or more, seventy or more, eighty or more, or ninety or more different CCPH-anti-CCPH antibody immunocomplexes. The present anti-IC antibodies may even bind immunocomplexes between all or substantially all known CCPH variants and an anti-CCPH antibody recognizing said variants, preferably a group-specific antibody, such as an anti-Adda antibody.

In some embodiments, the present group-specific anti-IC antibodies comprise a light chain variable region wherein CDR1 comprises SEQ ID NO:2, CDR2 comprises SEQ ID NO:3, and CDR3 comprises SEQ ID NO:4; and a heavy chain variable region, wherein CDRs 1-3 comprise amino acid sequences indicated in SEQ ID NOs: 30 or 31. According to an alternative definition, the light chain CDRs 1-3 comprise amino acid sequences set forth in SEQ ID NOs: 5 or 6.

Non-limiting examples of preferred group-specific anti-IC antibodies include those that comprise a light chain variable region comprising SEQ ID NO: 5 and a heavy chain variable region comprising SEQ ID NO: 30; and those that comprise a light chain variable region comprising SEQ ID examples of variant members of subgroup MC-XR include MC-LR, MC-RR, dmMC-RR, and MC-YR. Furthermore, antibodies SA58A12, SA41F2, SA52B4, and SA33D5, for example, are specific for a subgroup XR, i.e. they recognize immunocomplexes of both MCs and Nods having arginine (R) at position 4. Non-limiting examples of variant members of subgroup XR include MC-LR, MC-RR, dmMC-RR, MC-YR, and Nod-R. Finally, antibodies such as SA56D5, SA57A3, and SA60A1 are subgroup specific antibodies with MC-LR preferring specificity, whereas antibody SA42A3, for example, is a subgroup specific antibody with MC-RR-preferring specificity.

In addition to the above-mentioned non-limiting examples of particular subgroup specific antibodies, the present invention provides MC subgroup-specific antibodies comprising a light chain variable region, wherein CDRs 1-3 comprise amino acid sequences set forth in SEQ ID NOs: 15 or 16; and a respective heavy chain variable region, wherein CDRs 1-3 comprise amino acid sequences set forth in SEQ ID NOs: 40 or 41; MC-LZ subgroup-specific antibodies comprising a light chain variable region, wherein CDRs 1-3 comprise amino acid sequences set forth in SEQ ID NO: 17; and a respective heavy chain variable region, wherein CDRs 1-3 comprise amino acid sequences set forth in SEQ ID NOs: 42; MC-XR subgroup-specific antibodies comprising a light chain variable region, wherein CDRs 1-3 comprise amino acid sequences set forth in SEQ ID NOs: 18 or 19; and a respective heavy chain variable region, wherein CDRs 1-3 comprise amino acid sequences set forth in SEQ ID NOs: 43 or 44; XR subgroup-specific antibodies comprising and a light chain variable region, wherein CDRs 1-3 comprise amino acid sequences set forth in SEQ ID NOs: 20-23; and a respective heavy chain variable region, wherein CDRs 1-3 comprise amino acid sequences set forth in SEQ ID NOs: 45-48; antibodies with MC-LR preferring specificity comprising a light chain variable region, wherein CDRs 1-3 comprise amino acid sequences set forth in SEQ ID NOs: 24-27; and a respective heavy chain variable region, wherein CDRs 1-3 comprise amino acid sequences set forth in SEQ ID NOs: 49-52; and antibodies with MC-RR-preferring specificity comprising a light chain variable region, wherein CDRs 1-3 comprise amino acid sequences set forth in SEQ ID NOs: 28 or 29; and a respective heavy chain variable region, wherein CDRs 1-3 comprise amino acid sequences set forth in SEQ ID NOs: 53 or 54.

Further non-limiting examples of preferred subgroup-specific anti-IC antibodies include those that are MC subgroup-specific and comprise a light chain variable region comprising SEQ ID NO: 15 and a heavy chain variable region comprising SEQ ID NO: 40; or a light chain variable region comprising SEQ ID NO: 16 and a heavy chain variable region comprising SEQ ID NO: 41; those that are MC-LZ subgroup-specific and comprise a light chain variable region comprising SEQ ID NO: 17 and a heavy chain variable region comprising SEQ ID NO: 42; those that are MC subgroup-specific and comprise a light chain variable region comprising SEQ ID NO: 18 and a heavy chain variable region comprising SEQ ID NO: 43; or a light chain variable region comprising SEQ ID NO: 19 and a heavy chain variable region comprising SEQ ID NO: 44; those that are XR subgroup-specific and comprise a light chain variable region comprising SEQ ID NO: 20 and a heavy chain variable region comprising SEQ ID NO: 45, a light chain variable region comprising SEQ ID NO: 21 and a heavy chain variable region comprising SEQ ID NO: 46; a light chain variable region comprising SEQ ID NO: 22 and a heavy chain variable region comprising SEQ ID NO: 47; or a light chain variable region comprising SEQ ID NO: 23 and a heavy chain variable region comprising SEQ ID NO: 48; those that show MC-LR-preferring specificity and comprise a light chain variable region comprising SEQ ID NO: 24 and a heavy chain variable region comprising SEQ ID NO: 49, a light chain variable region comprising SEQ ID NO: 25 and a heavy chain variable region comprising SEQ ID NO: 50; or a light chain variable region comprising SEQ ID NO: 26 and a heavy chain variable region comprising SEQ ID NO: 51; or a light chain variable region comprising SEQ ID NO: 27 and a heavy chain variable region comprising SEQ ID NO: 52; and those that show MC-RR-preferring specificity and comprise a light chain variable region comprising SEQ ID NO: 28 and a heavy chain variable region comprising SEQ ID NO: 53, or a light chain variable region comprising SEQ ID NO: 29 and a heavy chain variable region comprising SEQ ID NO: 54.

Some of the present anti-IC antibodies are variant-specific, i.e. recognize only immunocomplexes of a single CCPH variant and an anti-CCPH antibody recognizing the same. For instance, antibodies SA56B8, SA59G2, SA56E7, and SA51D12 recognize immunocomplexes comprising MC-LR, antibodies SA41B5, and SA44E11 recognize immunocomplexes comprising MC-RR, whereas antibodies SA32C11, SA32F1, and SA34G1, recognize immunocomplexes comprising Nod-R.

In addition to the above-mentioned non-limiting examples of particular variant specific antibodies, the present invention provides MC-LR-specific antibodies comprising a light chain variable region, wherein CDRs 1-3 comprise respective amino acid sequences set forth in SEQ ID NOs: 7-10; and a heavy chain variable region, wherein CDRs 1-3 comprise respective amino acid sequences set forth in SEQ ID NOs: 32-35; MC-RR subgroup-specific antibodies comprising and a light chain variable region, wherein CDRs 1-3 comprise respective amino acid sequences set forth in SEQ ID NO: 11; and a heavy chain variable region, wherein CDRs 1-3 comprise respective amino acid sequences set forth in SEQ ID NO: 36; Nod-R subgroup-specific antibodies comprising and a light chain variable region, wherein CDRs 1-3 comprise respective amino acid sequences set forth in SEQ ID NOs: 12-14; and a heavy chain variable region, wherein CDRs 1-3 comprise respective amino acid sequences set forth in SEQ ID NOs: 37-39.

Further non-limiting examples of preferred variant-specific anti-IC antibodies include those that are MC-LR-specific and comprise a light chain variable region comprising SEQ ID NO: 7 and a heavy chain variable region comprising SEQ ID NO: 32, or a light chain variable region comprising SEQ ID NO: 8 and a heavy chain variable region comprising SEQ ID NO: 33, a light chain variable region comprising SEQ ID NO: 9 and a heavy chain variable region comprising SEQ ID NO: 34, or a light chain variable region comprising SEQ ID NO: 10 and a heavy chain variable region comprising SEQ ID NO: 35; those that are MC-RR subgroup-specific and comprise a light chain variable region comprising SEQ ID NO: 11 and a heavy chain variable region comprising SEQ ID NO: 36; and those that are Nod-R subgroup-specific and comprise a light chain variable region comprising SEQ ID NO: 12 and a heavy chain variable region comprising SEQ ID NO: 27, a light chain variable region comprising SEQ ID NO: 13 and a heavy chain variable region comprising SEQ ID NO: 38; or a light chain variable region comprising SEQ ID NO: 14 and a heavy chain variable region comprising SEQ ID NO: 39.

In one aspect, the present invention also provides a set of present anti-IC antibodies for profiling a sample for CCPHs. In some embodiments, said set comprises at least two antibodies selected from the group consisting of group-specific anti-IC antibodies set forth above including, but not limited to SA51D1 and SA51F6; subgroup-specific anti-IC antibodies including but not limited to SA42E10, SA52C2, SA55D1, SA41A5, SA51H4, SA58A12, SA41F2, SA52B4, SA33D5, SA56D5, SA57A3, SA60A1, SA57D4, SA42A3, and SA44E11; and variant-specific antibodies set forth above including, but not limited to, SA56B8, SA59G2, SA56E7, SA51D12, SA41B5, SA32C11, SA32F1, and SA34G1. In other words, said set may comprise any number of said antibodies beyond two in any desired combination.

In some other embodiments, said set comprises at least one antibody selected from generic antibodies set forth above including, but not limited to SA51D1 and SA51F6, and at least one other antibody selected from the group consisting of subgroup-specific antibodies SA42E10, SA52C2, SA55D1, SA41A5, SA51H4, SA58A12, SA41F2, SA52B4, SA33D5, SA56D5, SA57A3, SA60A1, SA57D4, SA42A3, SA44E11, and variant-specific antibodies set forth above including, but not limited to, SA56B8, SA59G2, SA56E7, SA51D12, SA41B5, SA32C11, SA32F1, and SA34G1.

Being specific for immunocomplexes enables that the present antibodies are suitable for use in non-competitive assay formats allowing sensitive and simple detection of CCPHs in a picomolar range, i.e. well below the WHO guideline limit (1 μg/L) for MC-LR. Non-competitive assays, also known as reagent excess assays, sandwich, immunometric or two-site assays, generally involve use of two antibodies targeting different epitopes, one antibody for antigen capture and the other labeled for detection. Especially the capture but, in some extent, also the detection antibody can be added in excess compared to the analyte. At low analyte concentration, unoccupied capture binding sites are always available, but as signal measurement occurs only at the occupied binding sites, the signal is directly proportional to the amount of analyte present. The situation is opposite in the reagent limited, competitive assays, where the analyte and the labeled tracer analyte compete for a limited number of binding sites of a single-type anti-analyte antibody used. In general, sandwich format provides considerable benefits in terms of assay robustness, sensitivity, specificity and kinetics. In addition, the working range typically is more extended compared to the competitive assay. For small sized analytes like CCPHs, the competitive assays are generally employed as finding two antibodies with separate epitopes is rare.

The present anti-IC antibodies may be employed in any available non-competitive immunoassay type as is readily understood by those skilled in the art. Non-limiting examples of suitable immunoassays include enzyme linked immunoabsorbent assays (ELISA), immunoflurometric assays (IFMA), fluorescent immunosorbent assays (FIA), such as time-resolved immunoflurometric assays (TR-IFMA), chemiluminescence immunoassay (CLIA), radioimmunoassay (RIA), open sandwich immunoassays (OS) and microsphere-based immunoassays (MIA).

Depending on the assay type employed, either the primary anti-CCPH antibody or the present anti-IC antibody, or both, may be conjugated or otherwise associated with a detectable label selected from the group including, but not limited to, optical agents such as fluorescent labels including a variety of organic and/or inorganic small molecules or a variety of fluorescent proteins and derivatives thereof, phosphorescent labels, chemiluminescent labels, and chromogenic labels; radioactive labels such as radionuclides that emit gamma rays, positrons, beta or alpha particles, or X-rays, and enzymes such as alkaline phosphatase (AP), or (horseradish) hydrogen peroxidase (HRP). Said association can be direct, e.g. through a covalent bond, or indirect, e.g. via a secondary binding agent, chelator, or linker. Techniques for conjugating or otherwise associating detectable agents to antibodies are well known and antibody labelling kits are commercially available from dozens of sources. One or both of the antibodies may also be expressed as fusion proteins with a detectable label or a detection tag by recombinant techniques.

In some embodiments, the anti-IC antibody is labelled. In some other embodiments, the anti-IC antibody is recognized by a further antibody (e.g. a species-specific antibody) comprising a detectable label. In some still other embodiments, the anti-IC antibody comprises a tag that is recognizable by a further antibody comprising a detectable label. In some still further embodiments, the anti-IC and said further antibodies are both labelled with the same label, e.g. for improving sensitivity in assays where the immunocomplex to be detected is expected to be rare. The anti-IC antibody and said further antibody may also be labeled with different labels.

An immunoassay provided herein may be a solid-phase immunoassay, such as a lateral flow assay or a conventional sandwich assay carried out on a solid surface, e.g. a microtiter plate. In these assay formats, either the primary anti-CCPH antibody or the anti-IC antibody is immobilized on the solid surface. Preferably, the antibody to be immobilized is the primary anti-CCPH antibody, preferably an anti-Adda antibody. A detectable sandwich between the analyte and the primary and secondary antibodies forms if the sample to be analyzed contains said analyte, i.e. one or more CCPH variants. Said solid-phase immunoassay may be either heterogeneous or homogeneous. In the heterogeneous assay, any free analytes or antibodies are physically separated from immunocomplexes formed, e.g. by washings, while no such separation is necessary in homogeneous assays making homogeneous assays preferable.

The present anti-IC antibodies are suitable for use not only in homogeneous solid-phase assay formats also in homogeneous immunoassays carried out in solution. Such in-solution immunoassays are particularly advantageous because no immobilization or washing steps are required, making them simple and easy to perform. Thus, in some preferred embodiments, the immunoassay is liquid-based homogeneous immunoassay.

In some embodiments, the immunoassay may be multiplex, with multiple simultaneous or sequential assays, and/or they may be carried out automatically using means and methods available in the art.

The present immunoassay for detecting the presence or absence, quantifying, and/or identifying of at least one CCPH variant in an aqueous sample may comprise the steps of a) reacting an aqueous sample suspected to contain one or more CCPH variants with a set of antibodies comprising at least one anti-IC antibody disclosed herein and an anti-CCPH primary antibody, wherein said anti-CCPH primary antibody binds to one or more CCPH variants present in the sample, if any, and forms an immunocomplex therewith, and wherein said at least one anti-IC antibody binds to said immunocomplex forming a sandwiched immunocomplex, and b) detecting the presence or absence of said sandwiched immunocomplex indicating the presence or absence of said one or more CCPH variants in said aqueous sample, respectively.

Anti-IC antibodies according to the present invention or combined sets thereof are particularly suitable for use in assays, such as on-site detection assays, and methods where a simple yes/no answer for the presence or absence of one or more CCPHs is enough. Thus, in one aspect, the present invention provides an assay which gives a yes/no result regarding on the presence or absence of toxin variants against whose immunocomplexes with a primary antibody the one or more anti-IC antibodies employed in the assay are specific for. The assay may give a single combined result regarding the presence or absence of any or a number of different CCPH variants. The broader the specificity of the anti-IC antibody or a combination thereof, the lower the risk for a false negative result. Alternatively or in addition, the assay may give multiple yes/no result regarding the presence or absence of specific CCPH variants or any combinations or subgroups thereof. Typical examples of samples to be analyzed by such yes/no tests include, but are not limited to, samples of recreational bathing waters.

The present anti-IC antibodies and combinations thereof are also suitable for fast and sensitive quantitative analysis of CCPHs in aqueous samples such as samples of drinking or environmental waters. Indeed, eleven major hepatotoxins, namely MC-LR, -dmLR, -LA, -RR, -dmRR, -YR, -LY, -LF-LW, -WR and Nod-R, were detected with sensitivities ranging from 0.011 g/L to 0.0499 μg/L in a 1 h TR-FIA assay disclosed in Example 2. The sensitivity of 0.029±0.008 µg/L, far below the World Health Organization guideline limit (1 µg/L), was obtained for MC-LR using an assay time as low as 10 min.

Furthermore, the present anti-IC antibodies and combinations thereof are suitable for use in assay formats that allow identifying or profiling CCPH variants present in a sample to be analyzed. The results may be expressed as yes/no results or as absolute or relative values indicating the amount of said CCPH variants in the sample to be analyzed.

In accordance with the above, the invention also provides use of the present anti-IC antibodies or combined sets thereof detecting the presence or absence, quantifying, and/or identifying of at least one CCPH variant in an aqueous sample, preferably a water sample, such as a sample of drinking water (e.g. a well water sample), recreational water (e.g. a bathing water sample), or any other environmental water.

In yet another aspect, the present invention provides a kit for immunodetecting, quantifying, and/or identifying at least one CCPH variant in an aqueous sample, wherein the kit comprises at least one anti-IC antibody disclosed herein. In some embodiments, said at least one anti-IC antibody is detectably labeled and/or comprises an affinity tag for immobilization purposes.

The kit may also comprise a primary anti-CCPH antibody, preferably an anti-Adda antibody, which may or may not comprise a detectable label or an affinity tag for immobilization purposes. In some further embodiments, either the anti-IC antibody or the anti-CCPH antibody is immobilized on a solid surface. The anti-IC and anti-CCPH antibodies may, independently from each other, be intact immunoglobulins or any antigen-binding fragments thereof, such as Fab, Fab', F(ab')$_2$, Fv or scFv fragments. In some still further embodiments, the antibodies may be provided in dried form.

In some embodiments, the kit may also comprise one or more other components for carrying out an immunoassay, such as blots (e.g., nylon or nitrocellulose), microtiter plates, reaction vials, lateral flow strips, appropriate standards, and reagents such as buffers, detection reagents (e.g. labels, chromogenic substrates, labelled further antibodies recognizing the present anti-IC antibodies, etc.), and wash solutions.

Typically, the kit also includes instructions for use, or direction to an outside source of instruction such as a website.

Any disclosed detail, advantage, embodiment, etc. relating to any aspect of the present invention also apply to other aspects of the intention unless clearly indicated otherwise.

It will be obvious to a person skilled in the art that, as the technology advances, the inventive concept can be implemented in various ways. The invention and its embodiments are not limited to the examples described below but may vary within the scope of the claims.

EXAMPLES

Example 1. Generation of Anti-IC Antibodies

Materials and Methods
Common Materials, Instruments and Reagents

Common inorganic and organic chemical reagents were obtained from commercial source either Sigma or Merck unless otherwise specified. The water used was purified by Millipore Milli-Q Plus water filtration purification system (Millipore Corporation, country). Restriction enzymes were either from Fermentas (Vilna, Lithuania) or from New England Biolabs (Ipswich, UK). Oligonucleotides were custom-synthesized by Tag Copenhagen or biomers.net. Molecular biology techniques were performed according to the standard protocols (Sambrook and Russell, 2001) if not mentioned. DNA manipulation kits were from Qiagen (Hamburg, Germany) or from Thermo Scientific (Fisher Scientific, Finland). Streptavidin-coupled magnetic beads (Dynabeads® MyOne™ Streptavidin C1, and Dynabeads® M-280 Streptavidin) and Dynal MPC magnet were purchased from Invitrogen Dynal AS, Oslo, Norway. Multilabel counter Victor™ 1420 for fluorescence measurement was from PerkinElmer Life Sciences, Finland. Assay buffer, enhancement solution, wash concentrate and streptavidin or rabbit anti-mouse (RAM) IgG coated microtiter plates were from Kaivogen (Turku, Finland). Monoclonal anti-Adda antibody, AD4G2 (Adda specific, anti-Microcystins) was from Enzo Life Sciences, Inc. (USA). Bacterial anti-alkaline phosphatase polyclonal antibody (anti-bAP pAb) was from LifeSpan Biosciences, Inc. (USA). Streptavidin was from BioSpa (Milan, Italy). Histidin tag scFv purification was done by His Spin Trap™ kit (GE Healthcare, UK). DNA and protein concentration were measured by NanoDrop ND1000 spectrophotometer (Thermo Scientific). Helper phage VCS M13 and the bacterial host *Escherichia coli* (*E. coli*) XL1-Blue were from Stratagene, La Jolla, Calif. TBT 0.05 and TBT 0.5 used in phage selection contained 50 mM TrisCl, 150 mM NaCl, pH 7.5 and tween 20 (0.05 and 0.5% respectively).

Biotinylation of Anti-Adda mAb

Biotinylation of anti-Adda mAb was performed with 40-fold molar excess of BITC (Biotinisothiocyanat, MW 404 g/mol) or NHS—SS-PEG4-Biotin (Pierce Biotechnology, USA) in 50 mM sodium carbonate buffer (pH 9.8). The biotinylated mAb was purified through two consecutive desalting columns (NAP5 and NAP10) and was eluted in TSA buffer (50 mM Tris, 150 mM NaCl, 0.02% NaN3), 0.1% BSA, pH 7.5 and kept at 4° C.

Eu Labeling of Detection Antibody

Polyclonal antibody raised against bacterial alkaline phosphatase, i,e, anti-bAP pAb (2 mg) was coupled with 120-fold molar excess of Europium (Eu) chelate [N1-(4-isothiocyanatobenzyl) diethylenetriamine-N1,N2,N3,N3-tetrakis(acetato)europium(III)] (Mukkala et al., 1989) in 50 mM carbonate buffer (pH 9.8) in total 1 ml volume. The reaction in dark was carried out overnight at RT and the Eu-labeled anti-bAP pAb was purified by FPLC (Pharmacia Biotech, Sweden) with a Superdex 200 column and finally eluted in TSA buffer, pH 7.75 and stored at 4° C.

Affinity Selection of Anti-Immunocomplex Antibodies

Immunocomplex specific binders were isolated from a synthetic universal scFv library where scFvs are displayed as fusions to truncated p3 protein of the filamentous VCS M13 phage (Brockmann et al., 2011; Huovinen et al., 2013). Three independent pannings were done in parallel using streptavidin coupled magnetic beads saturated with biotinylated anti-Adda mAb bound to either MC-LR, MC-RR or Nod-R.

To remove unwanted binders against streptavidin and anti-Adda mAb, phage library suspension [5×10$^{12}$ transforming units (tfu)/ml, in TSA, pH 7.5, 1% BSA] was incubated (2 h) on streptavidin coated microtiter wells saturated with BITC biotinylated anti-Adda mAb (300 ng/well) and collected. After the subtractive step, unspecific native mouse Ig G (1 µg/ml), biotinylated anti-Adda mAb (35 ng/ml), biotin-blocked streptavidin (2.5 µg/ml) and free biotin (25 µM) were added as blocking agents and divided into five aliquots (1 ml each). Meanwhile 100 µl (10 mg/ml)

streptavidin magnetic beads were used to saturate with biotinylated anti-Adda mAb and divided into four aliquots. In three aliquots excess of free toxin (either MC-LR, MC-RR or Nod-R) were added to prepare three different immunocomplex saturatated beads suspension (200 µl of TBT 0.05). Each aliquot (1 ml) of pretreated library suspension (mentioned earlier) was incubated for 30 min at RT with 200 µl of corresponding immunocomplex saturated beads (7-10× $10^9$ beads/ml). For monitoring background binding two parallel control reactions (uncoated beads and beads coated only with Bio adda mAb) were run. After three washes with 0.9 ml of TBT 0.5, phages bound to the beads were eluted with 100 µl of trypsin (60 µg/ml, in TBS) for 30 min at 37° C. with shaking (300 rpm) and the reaction was stopped with 100 µl of soybean trypsin inhibitor (100 µg/ml, in TBS). Each elution was used to infect 1 ml of exponential phase ($OD_{600}$=~0.5) XL1-Blue E. coli cells (grown in SB supplemented with 10 µg/ml tetracycline) for 30 min at 37° C. 10 µl of infected cells were used to titer the eluted phages and the rest were plated on LA (0.2% (w/v) glucose, 12.5 µg/ml tet and 25 µg/ml cam) and grown overnight at 30° C. The grown cells were then used to inoculate 20 ml SB [1% (w/v) glucose, 10 µg/ml tetracycline and 25 µg/ml cam] media with initial $OD_{600}$ of 0.1. To amplify phages, cultures were incubated at 37° C., 300 rpm and when the OD600 was 0.5, the cells were infected with 20-fold excess of helper phage, VCS M13 at 37° C. for 30 min with 50 rpm. Only the cells were collected and resuspended into 50 ml of fresh SB medium of the same composition except glucose was missing. The cultures were continued to grow at 30° C., 300 rpm and after 1.5 hours phagemid were selected by addition of 50 µg/ml kanamycin followed by induction with 100 µM isopropyl-β-D-1-thiogalactopyranoside (IPTG). Phages were produced o/n at 26° C., 250 rpm and were isolated in TSA buffer (pH 7.5, 0.1% BSA) by double precipitation with 4% polyethylene glycol (PEG) 8000/3% NaCl.

For each panning, selection was repeated for another cycle using the same corresponding toxin with the following modifications. In the second round, NHS-SS-PEG4-biotinylated anti-Adda mAb was used to form immunocomplex. Also, after the subtractive step, $1 \times 10^{10}$ tfu of the phage was mixed with 5 µl (~6-7×$10^8$ beads/ml) of immunocomplex coated beads (Dynabeads® M-280). Amount of unspecific native mouse Ig G (blocking agent) was increased to 500 µg/ml. From the beads, bound phages were eluted by addition of 200 µl of 50 mM dithiothreitol (DTT).

Phage Immunoassay

Corresponding phage stocks were prepared after each selection round and phage enrichment during each selection was followed by phage immunoassay. In prewashed streptavidin wells, biotinylated anti-Adda mAb or unspecific biotinylated antiHK2 mAb (6H10) as negative control were added (50 ng/well), incubated for 1 h with shaking and washed four times. Each phage stock was tested with three free antigens (MC-LR, MC-RR and Nod-R) as 50 ng/well. Assay buffer with no toxin was added in the blank and control wells. After 1 h incubation, plates were washed four times and 2e10 phage from each panning rounds were added and incubated for 1 h and washed four times. Bound phage were detected with N1 Eu labeled rabbit anti-fd (anti-phage) pAb (Sigma-Aldrich). Each sample was measured as a duplicate.

Cloning, Expression, Screening Purification

ScFv gene isolated from the second panning round plasmid DNA were ligated at SfiI sites in vector pAK600 His6, a derivative from pAK600 (Krebber et al., 1997) for the expression of histidine tagged scFv as a fusion to alkaline phosphatase (scFv-AP) in XL1-Blue E. coli cells.

Manually picked single colonies were grown in SB (100 µg/ml Amp, 10 µg/ml Tet, 0.05% glucose) on the 96-well microtiter plates (SARSTEDT) and the scFv-AP protein was expressed by o/n induction with 100 µM IPTG at 26° C.

Expression cultures were frozen and thawed at least twice, the cells were pelleted by centrifugation and the supernatant was used for the primary screening immunoassays. Screening was done using RAM or SA surface to capture IC comprising MC-LR, MC-RR or Nod-R (10 µg/L). Presence of anti-IC scFv-AP in supernatant of expression cultures were detected by AP activity or by Eu labelled anti-AP antibody. Selected clones (based on specificity profile and high signal) were expressed as a 5 ml tube cultures and were checked again for their specificities towards nine different toxin variants, MC-LR, -dmLR, -RR, -dmRR, -YR, -LY, -LF, -LW and Nod-R (FIG. 1A) in a similar manner. Selected clones with differing specificity profiles towards the nine toxin variants were sequenced. Finally, selected clones were expressed as 50 ml culture and purified by His trap column according to the manufacturer's instructions. Results obtained with generic antibody SA51D1 are shown in FIG. 4, while results obtained with antibodies SA56B8, SA55D1, SA58A12 and SA32C11 are shown in FIG. 5.

Measuring the Cross Reactivity Profile of the Antibody with MC Variants and Nod

Different purified MC variants and Nod (FIG. 1A) at different concentration range from 0.001 to 300 μg/L were analyzed to determine cross reactivity profile of the selected clone by the single-step non-competitive assay disclosed in Example 2.

Measuring the Cross Reactivity Profile of the Antibody with Immunocomplex and Naked Anti-Adda mAb Binding of SA51D1 was explored using Octet RED384 instrument (Pall ForteBio). Three measurements (A, B and C) were performed in duplicates using tilted-bottom 384-well microplates (ForteBio) with 1000 rpm agitation at 30° C. Colorless Assay Buffer (Kaivogen) [0.05 M Tris-HCl, pH 7.75, 0.9% (w/v) NaCl, 0.05% (w/v) NaN3, 0.01% (v/v) Tween 40, 0.05% (w/v) bovine-γ-globulin, 20 μM diethylenetriaminepentaacetate (DTPA), and 0.5% (w/v) bovine serum albumin (BSA)] was used.

Biotinylated ADDA Mab AD4G2 (1 μg/ml) was immobilized on Streptavidin biosensor (Dip and Read SA Biosensors, ForteBio) for 200 sec. In order to form IC, another loading was performed with MC-LR (1 μg/ml) for 200 sec. In blank measurement (C) only buffer was used instead of MC-LR. All sensors were incubated in buffer for 60 sec. In measurement B and C, association of SA51D1 (1 μg/ml) was observed for 200 sec after which sensors were directed back to buffer for dissociation phase for 600 sec. For measurement A, SA51D1 (1 μg/ml) was pre-incubated for 15 min in presence of 500 μg/L of MC-LR and association was observed in presence of 500 μg/L of MC-LR in buffer.

Results

Immunocomplex Panning

As set forth in more detail above, biotinylated anti-Adda mAb was immobilized on the surface of streptavidin coated magnetic beads together with either MC-LR, MC-RR, thus forming an immunocomplex (IC). The beads were used for the selection of the binders from the synthetic scFv library displayed on the phage. For each antigen, two rounds of panning were performed in addition to the subtractive panning meant for removal of binders specific towards streptavidin or mere anti-Adda mAb. Phages rescued at different panning rounds were tested for their immunoreactivity towards ICs consisting of anti-Adda mAb bound either with MC-LR, MC-RR or Nod.

Enrichment of IC binders was noticeable (9-16×) already in the first panning round and especially after the second round (47-49×). After second panning round, although some enrichment of binders towards free anti-Adda mAb occurred (11.6×), binding to the ICs was clearly more efficient (at least three times more). No significant enrichment (less than 2.3×) was observable towards streptavidin surface, or to unspecific $IgG_1$ antibody. Despite using only a single antigen (MC-LR, MC-RR or Nod-R) during each panning, interestingly the phage population showed immunoreactivity towards all the three types of ICs, suggesting the possible presence of generic or group specific binders capable of recognizing other toxin variants.

Screening Summary

The selection output from each second round was subcloned into the expression vector PLK06H, which leads to expression of scFv-AP antibody fragments with a His tag. A total of around 1600 individual clones were screened for binding towards the IC of either MC-LR, MC-RR or Nod-R and anti-Adda mAb immobilized on RAM or streptavidin wells. The binding of scFv-AP was detected by AP activity or by Eu labelled anti-bAP antibody. Over 70% of the clones were found to be positive (S/B>3) against at least single type of IC.

Clones with the highest S/B ratio (usually top 25-30%) together with all clones having interesting profile (specific to single toxin) were further tested for their cross reactivity towards nine different cyanotoxins: MC-LR, -dmLR, -RR, -dmRR, -YR, -LY, -LF-LW, and Nod-R (FIG. 1A). Potential clones with different binding characteristics were sequenced to reveal their DNA and amino acid composition. Selected clones were purified. For example, ScFv-AP clone SA51D1 was purified with his tag affinity column and used to develop the single-step non-competitive assay disclosed in Example 2.

Figure 11:
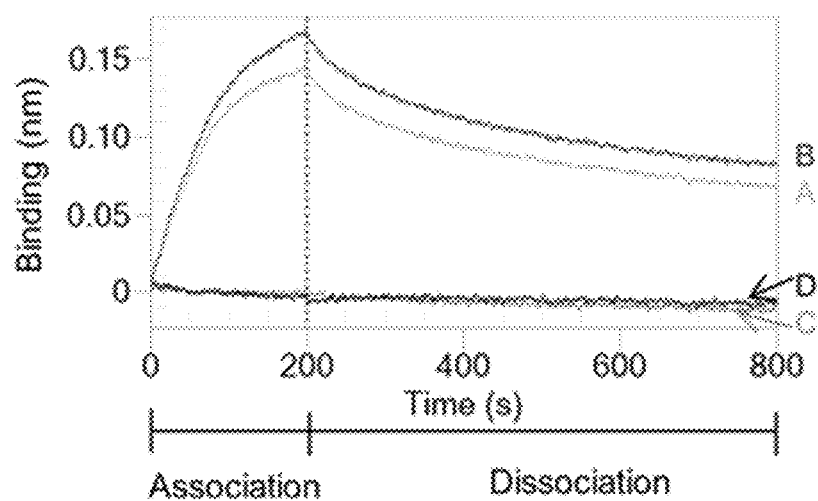
FIG. 11 shows the specificity of binding of clone SA51D1 towards immunocomplex (formed by anti-Adda Mab and MC-LR) and to anti-Adda mAb without MC-LR. Sensogram A and B show the association and dissociation of SA51D1 to immunocomplex in presence (A) or absence (B) of MC-LR in buffer. As shown in sensogram A, presence of free MC-LR in the buffer did not have effect to the association or dissociation of SA54D1 to IC, thus indicating that SA51D1 has no affinity towards free MC-LR. The sensogram C shows neglegtable binding of SA51D1 to the anti-Adda mAb alone. The sensogram D represent matrix background (streptavidin surface, D). The results showed SA51D1 binds specifically to the immune complex.

Binding interaction between IC and anti-IC SA51D1 was observed in presence of MC-LR on Octet instrument which uses BioLayer Interferometry (BLI) for label free measurements. The sensograms obtained in realtime measurements revealed that there is no interaction of the scFv-AP SA51D1 towards the primary antibody when no IC was formed. Also pre-incubation of SA51D1 with MC-LR did not hinder the association of scFv-AP SA51D1 to the IC, revealing that the scFv-AP does not have affinity towards free toxin only (FIG. 11).

Example 2. Single-Step Non-Competitive Time-Resolved Immuno-Fluorometric Assay

This example demonstrates the use of an anti-IC antibody according to the present invention in a single-step non-competitive (i.e. sandwich) time-resolved immunofluorometric (TR-IFMA). The assay was validated with spiked as well as with environmental water samples.

Materials and Methods

Toxin Standards

Specific amount of the purified toxins: MC-LR, dm-MC-LR, MC-RR, dmMC-RR, MC-YR, MC-LY, MC-LF, MC-LW, Nod-R (FIG. 1A) were obtained from Dr. Meriluoto's Lab (Åbo Akademi University) as a lyophilized dried powder. The toxins were purified by preparative HPLC (Column: Nucleosil C 18 250×21 mm, 7 µm particles, Eluent: 27% ACN and 73% 0.013 M ammonium acetate). Toxin identification was done in fractions and purity was checked on analytical HPLC. Concentration was done on SPE cartridges. Second purification was done on a semi-preparative HPLC column when needed. Purity was checked on LC-MS (ion trap HCT Ultra) and determination of toxin concentration was done by analytical HPLC. MC-LA and MC-WR (FIG. 1A) were purchased from Enzo Life Science. All the toxin standards were stored dry at −20° C. until required. Dry powder was dissolved in 50% methanol (100-250 µg/ml original stock), further working stocks were diluted in MQ and kept at −20° C. or 4° C. in sealed condition. Standards were prepared in Milli-Q water and stored short term at 4° C.

Single-Step Non-Competitive Assay

In prewashed streptavidin strips, samples or toxin standards (0-300 µg/L) were added as 100 µl/well. Reagent mixture comprising biotinylated anti-Adda mAb (100 ng/well), purified SA51D1 scFv-AP (100 ng/well), and N1-Euanti-bAP PAb, (50 ng/well) was added as 100 µl/well. The strips were incubated for 55 min at RT with slow shaking followed by four washes. Then enhancement solution (ES) was added (200 µl/well), incubated for 5 min (RT, slow shake) and the Eu Fluorescence signal was measured with multi-label counter, Victor. Sample concentration was calculated using the Multicalc program (Perkin Elmer).

Effect of Incubation Time

Effect of incubation time of 5 min to 4 h was tested for the non-competitive assay using MC-LR (conc in well: 0-30 µg/L) at RT.

Detection of MC-LR from Spiked Water Samples

Five water samples (distilled MQ water from the laboratory, tap water sample from the laboratory and three environmental water samples from three different lakes of Finland) were used for spiking with MC-LR. Environmental samples were previously tested with ELISA, PPIA, HPLC and MS/MS and found to be free of intracellular MCs/Nods. The samples were spiked with MC-LR over a range of concentrations (0, 0.2, 0.4, 1 and 4 µg/L).

Detection of Cyanotoxin from Environmental Water Sample

Environmental samples (collected during 2009 from Finland and Estonia) were tested using the single-step non-competitive TR-IFMA assay for internal/cellular and extracellular/released toxin in water. For each sample there were two sets. One set of samples were stored at −20° C. in lyophilized form and have been tested with ELISA, PPIA, HPLC, and LC-MS for the cellular cyanotoxin amounts/ variants as well as for the presence of cyanobacteria. The methods including sample collections were described earlier (Meriluoto and Codd, 2005), (Hautala et al., 2013). The lyophilized samples were reconstituted in MQ to the final conc of 4× or 1× before being used by the non-competitive assay. Another set of each samples (2 ml aliquots) which were frozen fresh and stored at −20° C. were used as such after thawing to RT for determining the (extracellular) toxin amount by the developed non-competitive assay.

Results

The Single-Step Non-Competitive Immunoassay

Figure 2:
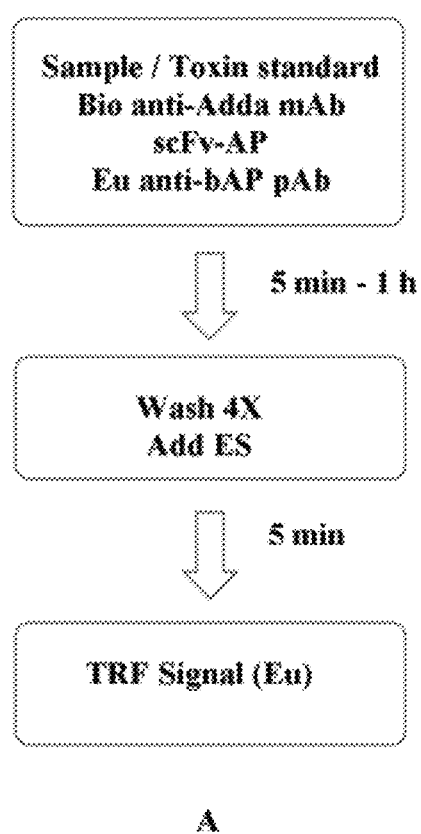
FIG. 2 illustrates a single-step non-competitive immunoassay procedure (A) and concept (B) of Example 2. Sensitive TR-IFMA signal generation is based on the use of Eu-labeled anti-AP pAb.
Figure 2:
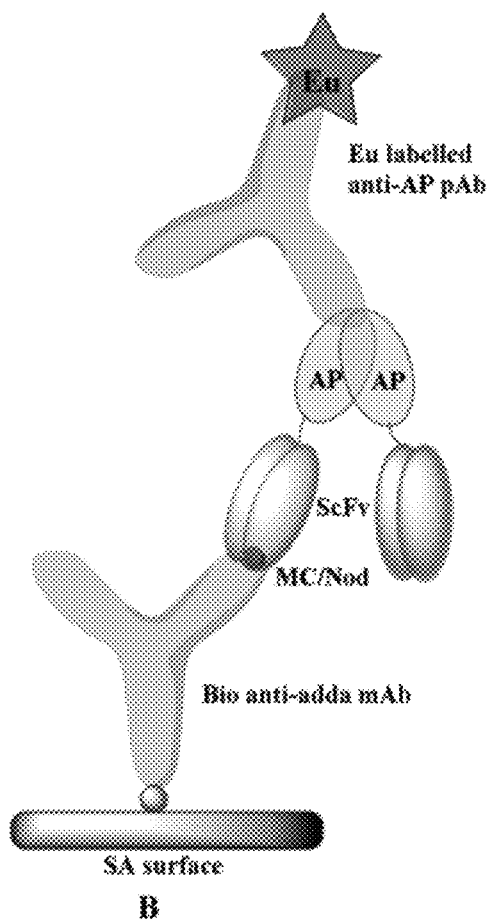

The scFv-AP clone SA51D1 was used to set up a single-step non-competitive immunoassay for the detection of MCs and Nods. The assay procedure and concept are shown in FIG. 2. In brief, samples or standards were pipetted in the volume of 100 µl on streptavidin coated microtiter wells followed by the addition of 100 µl of reagent mixture containing all the immunoreagents i.e. biotinylated anti-Adda mAb, anti-IC scFv-AP and Eu-labeled anti-AP pAb. The resulting IC sandwich was captured on the streptavidin surface. After a washing step, 200 µl enhancement solution was added, incubated for 5 min and highly sensitive measurement of time resolved-fluorescence (TR-IFMA) signal was performed.

Optimization of Assay Components

Amount of capture biotinylated anti-Adda mAb (50-200 ng/well), anti-IC binder scFv-AP SA51D1 (50-500 ng/well) and tracer Eu anti-bAP pAb (25-300 ng/well) were optimized for the single-step assays. Finally 100 ng of bio-anti-Adda mAb, 100 ng of scFv-AP and 50 ng of Eu anti-bAP pAb per well were used in subsequent experiments.

Effect of Incubation Time

Figure 3:
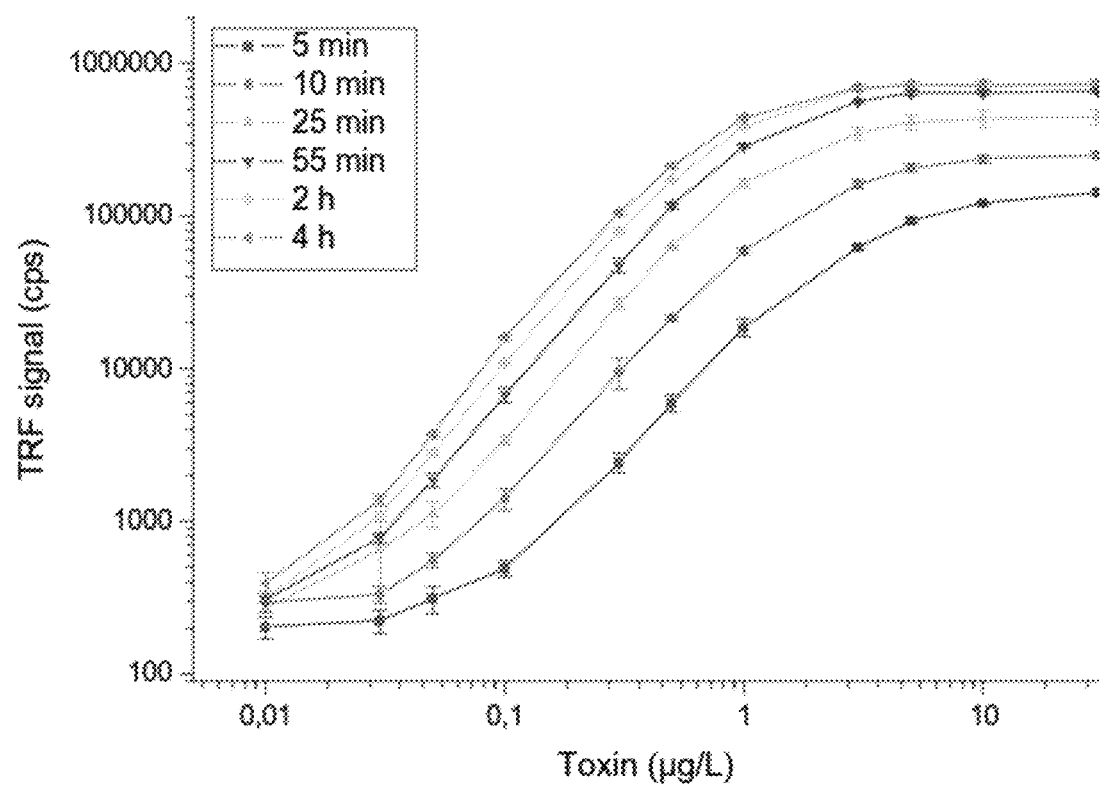
FIG. 3 illustrates the effect of incubation time ranging from 5 min to 4 h in the single-step non-competitive assay of Example 2. MC-LR was used in the experiment. Each value represents the average of two independent assays done on separate days using similar conditions.

The effect of incubation time was tested in the single-step non-competitive assay format. MC-LR (concentration in well: 0-30 µg/L), bio anti-Adda mAb, scFv-AP SA51D1, and Eu anti-bAP pAb were incubated together from 5 min to 4 h followed by four washes, addition of 200 µl of enhancement solution per well and signal generation for 5 min (FIG. 3). Sensitivity (blank+3SD, n=6) were 0.029 µg/L, 0.012 µg/L and 0.012 µg/L with 5 min, 55 min and 4 h incubation time respectively. Incubating longer than 1 h seems do not have any added benefit. Although WHO guideline value of 1 µg/L could easily be met by 5 min incubation assay, for practical reasons (such as sample handling, saturation of Eu signal) total 1 h assay (55 min incubation+5 min signal generations) was used in later experiments.

Determination of Cross-Reactivity with Different Cyanotoxin Variants

Figure 4:
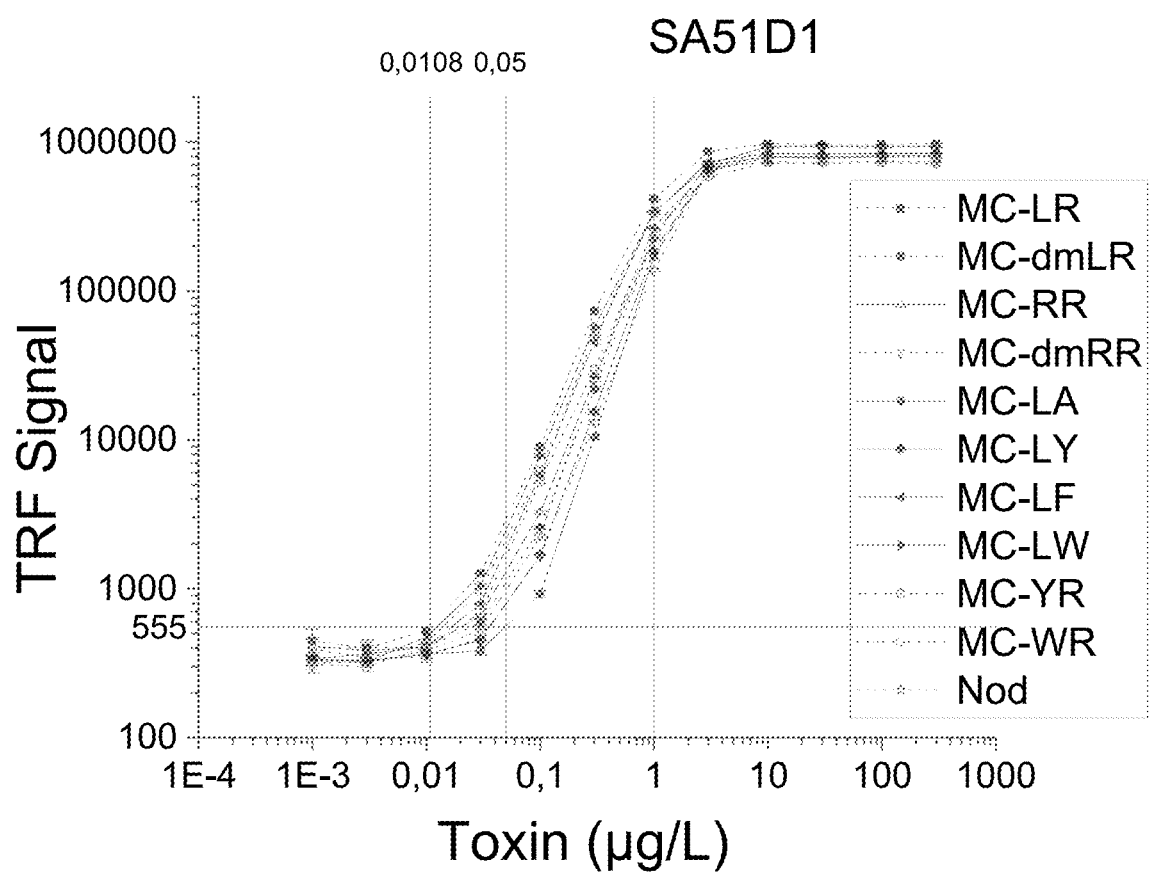
Figure 5:
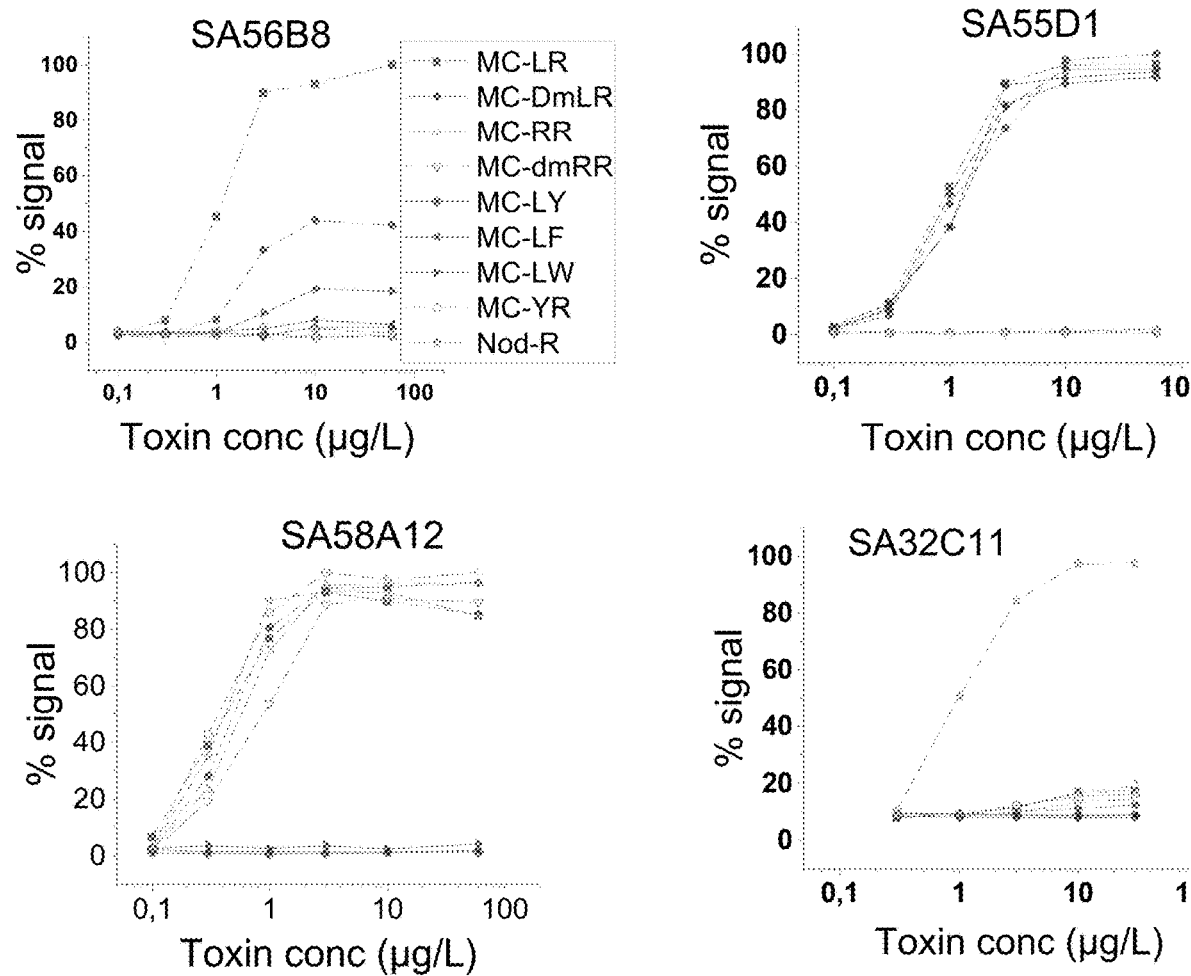
FIG. 5 shows an example of a cross-reactive pattern of four anti-IC binders: SA56B8, SA55D1, SA58A12 and SA32C11 against MC-XZ and Nod-R. Concentration of toxin (0.1 to 60 µg/L) is plotted as logarithmic scale in X axis and corresponding signal (%) is plotted in Y scale. Solid symbols represent all the MC-XZ, where X=L (Leu). Nod-R and MC-XZ where Z=R (Arg) are plotted as dashed line. Each value represents average of two replicates. Binder SA56B8 was found to be MC-LR and MC-dmLR specific and MC-LW was recognized weakly (signal below 20%). Binder SA55D1 was found to be specific towards MC-XZ, where X=L (Leu) whereas binder SA58A12 was specific towards MC-XZ where Z=R (Arg) and also towards Nod-R. Binder SA32C11 shows specificity only towards Nod-R.

Assay specificity to eleven different cyanotoxins (FIG. 1A) was evaluated and results are shown in FIGS. 4 and 5.

Single-Step Assay with Spiked Water Sample

The developed assay was tested by the spiked water (0, 0.2-4 µg/L) and the recovery ranged from 80% to 137% without any dilution and concentration step of the sample. Table 1 shows the measured concentration and the recovery percentage. The same environmental samples were found to be free of detectable intracellular MCs or Nods tested by ELISA; PPIA; HPLC and LC/MS. Though the samples were free from internal toxins, there is a possibility that the water samples might have already released extracellular toxins.

TABLE 1

Detection results of spiked water samples

| Origin of Water sample (Date of collection) | MC-LR added to the sample (µg/L) | MC-LR determined by non-competitive immunoassay (µg/L) | CV (%) | Recovery (%) |
|---|---|---|---|---|
| 1 MQ (9 Aug. 2012) | 0 | 0 | — | — |
|  | 0.2 | 0.25 | 5.9 | 127 |
|  | 0.4 | 0.46 | 3.5 | 114 |
|  | 1 | 1.06 | 0.7 | 106 |
|  | 4 | 5.49 | 4.0 | 137 |
| 2 TAP water (9 Aug. 2012) | 0 | 0 | — | — |
|  | 0.2 | 0.24 | 13.1 | 118 |
|  | 0.4 | 0.38 | 4.8 | 95 |
|  | 1 | 1.02 | 0.5 | 102 |
|  | 4 | 4.85 | 6.3 | 121 |
| 3 Haunisten Allas, (4 Nov. 2009) | 0 | 0.05 | 31.2 | — |
|  | 0.2 | 0.23 | 11.1 | 117 |
|  | 0.4 | 0.42 | 2.6 | 105 |
|  | 1 | 1.02 | 1.5 | 102 |
|  | 4 | 4.99 | 5.4 | 125 |
| 4 Björby träsk, Åland (28 Jul. 2009) | 0 | 0.045 | 15.8 | — |
|  | 0.2 | 0.20 | 6.4 | 101 |
|  | 0.4 | 0.36 | 3.5 | 89 |
|  | 1 | 0.80 | 5.9 | 80 |
|  | 4 | 3.88 | 7.7 | 97 |
| 5 Toböle träsk, södra, Åland (28 Jul. 2009) | 0 | 0.031 | 9.5 | — |
|  | 0.2 | 0.20 | 16.9 | 98 |
|  | 0.4 | 0.36 | 2.3 | 90 |
|  | 1 | 0.84 | 5.9 | 84 |
|  | 4 | 4.17 | 8.2 | 104 |

The MQ was sterilized by autoclaving. The collected environmental samples were stored at −20° C. until use. Coefficient of variations % (CV %) are of two replicate measurements.

Detection of MCs and Nod from Environmental Samples

A total of 20 environmental water samples from Åland island of Finland, mainland Finland and Estonia were analyzed with the developed single-step non-competitive TR-IFMA assay to determine the cellular and external MC/Nod concentration present in the water. The samples included lake and sea water. The samples were previously analyzed with ELISA, PPIA, HPLC and LC-MS for the cellular toxin amount. Positive correlation was found with both cellular and extracellular toxin concentration measured by single-step assay compared to the cellular toxin concentration measured by other methods. The correlations were 0.9969, 0.8723, 0.9807, 0.9912 for cellular toxins and 0.9569, 0.9272, 0.8969, 0.968 for extracellular toxin measured by ELISA, PPIA, HPLC and LC-MS respectively. Amount of released toxin in the water in several samples are found to be higher than the extracted cellular toxin in many samples. The measured concentration by the non-competitive immunoassay falls between the different measured values indicating the practical applicability of the assay which includes direct use of environmental water as well as cell extracted toxin samples.

TABLE 2

Microcystin/nodularin concentrations, identified toxin variants and main cyanobacterial genera in environmental water samples from Finland and Estonia.

| Place and Sampling date | MCs/Nod amount (µg/L) | | | | | | Observed MCs/Nod variant | | Main cyanobacterial genera |
|---|---|---|---|---|---|---|---|---|---|
|  | Single-step non-competitive assay External | ELISA cellular | PPIA cellular | HPLC cellular | LC-MS cellular | | HPLC | LC-MS | |
| Karviken (Sea), Åland, Finland. 28 Jul. 2009 | 0.026 | 0 | 0 | 0 | 0 | 0 | — | — | *Aphanizomenon* |

TABLE 2-continued

Microcystin/nodularin concentrations, identified toxin variants and main cyanobacterial genera in environmental water samples from Finland and Estonia.

| | MCs/Nod amount (µg/L) | | | | | | | | |
|---|---|---|---|---|---|---|---|---|---|
| | Single-step non-competitive assay | | ELISA | PPIA | HPLC | LC-MS | | | Main |
| Place and | Ex- | cel- | cel- | cel- | cel- | cel- | Observed MCs/Nod variant | | cyanobacterial |
| Sampling date | ternal | lular | lular | lular | lular | lular | HPLC | LC-MS | genera |
| Brantsböle träsk, Åland, Finland. 27 Jul. 2009 | 23.05 | 18.78 | 29.3 | 11.3 | 20.0 | 21.4 | MC-LR, MC-LY | MC-dmLR, MC-LR, MC-LY, MC-LW, MC-LF | Microcystis, Anabaena |
| Nåtö hemviken, Åland, Finland. 30 Jul. 2009 | 13.92 | 6.73 | 11.3 | 8.9 | 4.6 | 8.6 | MC-RR, MC-YR, MC-LR | MC-dmRR, MC-RR, MC-YR, MC-dmLR, MC-LR | M. aeruginosa, M. viridis, M. flosaquae, Aphanizomenon, Anabaena spp. A. solitaria |
| Nåtö vägbank, (Sea), Åland, Finland. 29 Jul. 2009 | 1.109 | 0.471 | 1.5 | 0.2 | 1.1 | 1.5 | NOD | NOD | Aphanizomenon, Nodularia |
| Hauninen, Turku, Finland. 1 Jul. 2009 | 3.885 | 0.545 | 1.2 | 0.36 | 0.85 | 1.1 | MC-dmRR | MC-dmRR | Planktothrix, Aphanizomenon, Anabaena, Microcystis |
| Hauninen, Turku, Finland. 17 Aug. 2009 | 0.368 | 0.23 | 0.55 | 0.23 | 0.29 | 0.39 | MC-dmRR | MC-dmRR, MC-RR, MC-dmLR, 1031.5 | Planktothrix, Aphanizomenon, Anabaena |
| Savojärvi, Finland. 27 Aug. 2009 | 15.21 | 10.36 | 14.8 | 4.8 | 11.3 | 13.3 | MC-dmRR, MC-RR, MC-dmLR, MC-LR | MC-didmRR, MC-dmRR, MC-didmLR, MC-dmLR | Anabaena, Snowella |
| Vandö kanal Åland, Finland. 28 Jul. 2009 | 0 | 0 | 0 | 0 | 0 | 0 | — | — | Microcystis |
| Höckböle träsk, Åland, Finland. 28 Jul. 2009 | 0.04 | 0.06 | 0.07 | 0 | 0 | 0 | — | — | A. lemmermannii |
| Dalkarby träsk, Åland, Finland. 29 Jul. 2009 | 0 | 0 | 0 | 0 | 0 | 0 | — | — | M. aeruginosa |
| Merttilän pato, Raisio-Naantali, Finland. 24 Aug. 2009 | 0.15 | 0.073 | 0.08 | 0 | 0 | 0.04 | — | MC-dmRR, MC-RR | NA |
| Ridasjärvi, Finland. 28 Jul. 2009 | 0 | 0 | 0.04 | 0.09 | 0 | 0 | — | — | NA |
| Suolijärvi Holma, Finland. 3 Aug. 2009 | 0.28 | 0.138 | 0.08 | 0 | 0 | 0.13 | — | MC-dmRR | NA |
| Hirvijärvi, Finland. 5 Aug. 2009 | 0.05 | 0.010 | 0.04 | 0 | 0 | 0.01 | — | MC-dmRR | NA |
| Tuusulanjärvi, Finland. 13 Jul. 2009 | 0.07 | 0.010 | 0.03 | 0 | 0 | 0.01 | — | MC-dmRR | NA |
| Littoistenjärvi, Finland. 4 Jul. 2009 | 0.05 | 0.061 | 0.08 | 0 | 0 | 0.02 | — | MC-dmRR | NA |
| Narva pumppuasema, Estonia. 5 Aug. 2009 | 0.47 | 0.073 | 0.08 | 0 | 0 | 0.1 | — | MC-dmRR, MC-RR, MC-LR | NA |
| Mustvee (Peipsi), Estonia. 24 Aug. 2009 | 0.25 | 0.042 | 0.06 | 0 | 0 | 0.08 | — | MC-dmRR, MC-RR, MC-LR | NA |
| Stroomi rand (Sea), Estonia. 18 Aug. 2009 | 0.08 | 0.176 | 0.34 | 0.17 | 0.17 | 0.25 | NOD | MC-dmRR, NOD | NA |
| Harku järvi, Estonia. 18 Aug. 2009 | 3.4 | 2.9 | 4.1 | 2.4 | 4.6 | 2.0 | MC-dmRR, MC-RR, MC-LR | MC-dmRR, MC-RR, MC-YR, MC-dmLR, MC-LR | NA |

Example 3. Single-Step Non-Competitive Chromogenic Assay

This example demonstrates that the present anti-IC antibodies are suitable also for use in a chromogenic non-competitive ELISA assay.

Biotinylated anti-Adda mAb (50 ng) and 200 ng of SA51D1 scFv-alkaline phosphatase fusion protein in 100 µL of PBS, pH 7.4 buffer were dispensed in streptavidin-coated 96-well microtiter plate (Kaivogen, Turku, Finland) together with 100 µL of each nine different CCPH standard (FIG. 1A) solutions ranging from 0.003 to 30 µg/L as duplicates. Wells were incubated in shaking at room temperature for one hour and then washed for four times. Color formation was started by adding 200 µL of para-Nitrophenylphosphate Liquid Substrate System (Sigma Aldrich, USA). Color formation was measured at different time points from 1 hour to 19 hours by reading absorbance at 405 nm with Victor multilabel counter (Perkin-Elmer Wallac, Turku, Finland).

Figure 6:
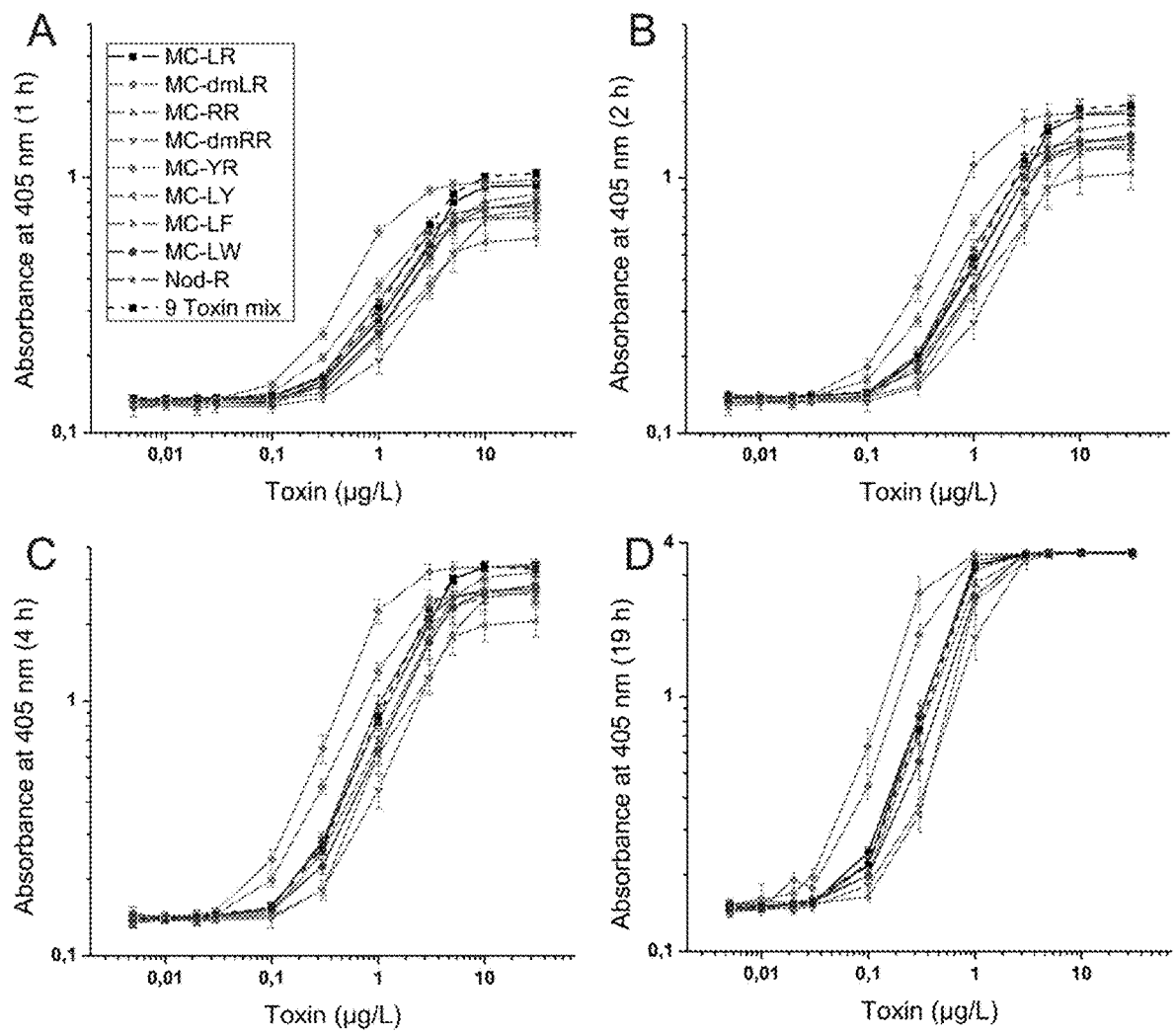
FIG. 6 illustrates single-step ELISA sandwich immunoassay standard curves for nine different CCPH using SA51D1 as a secondary antibody for recognizing the IC. Alkaline phosphatase activity for 1 h (A), 2 h (B), 4 h (C) or 19 h (D) was measured with pNPP as substrate for signal generation at 405 nm. Also nine toxin variants mixed in equal ratio in one sample was used to generate the standard curve. Each point is average signal of two independent assays performed on different days. Standard errors of mean of the individual variants are also shown. For example, at 2 h measurement (B), the sensitivity of MC-dmLR and MC-YR falls below 0.1 µg/L and for the rest of the variants the sensitivity falls below 0.3 µg/L. Also, the signal to background ratio ranges from 2.1 to 5 for all the toxin variants at conc. 1 µg/L.

Results shown in FIG. 6 illustrate that the single-step ELISA assay with SA51D1 scFv-alkaline phosphatase fusion protein recognizes even with 1 hour signal development all tested CCPHs with sensitivity below 1 µg/L, which is maximum WHO guidance level for MC-LR in drinking water.

Example 4. Quantitative Lateral Flow Test with Fluorescent Nanoparticles Conjugated to Anti-Ic Antibodies This example demonstrates that the present anti-IC antibodies are also suitable for use in a lateral flow assay format.

Up-converting nanoparticles (UCNP, [~40 nm NaYF4:Yb3+, Er3+ up-converting phosphor nanoparticles) were activated using 1 mg of UCNP's and incubation in 20 mM MES, pH 6.1 buffer, 30 mM sulfo-NHS and 10 mM EDC for 45 min at room temperature. Excess reagents were removed and washed away with Nanosep 30K filter (Pall Life Sciences) and 20 mM MES, pH 6.1 buffer. Streptavidin (Bio-Spa, Italy) (50 µg) was added to activated UCNP solution and incubated for 2.5 hours at RT. Glycine (50 mM) was added to stop the conjugation reaction and unreacted components were removed by centrifugation with 300K Omega filter (Pall Life Sciences) and at the same step washed with 5 mM Tris, pH 8.5; 0.05% Tween-85; 0.5% BSA; 0.05% $NaN_3$ buffer. Streptavidin-UCNP conjugates were stored at +4° C.

Anti-ADDA mAb (100 µg) was biotinylated using 40-fold molar excess of isothiocyanate derivative of biotin (Perkin-Elmer Life Sciences, Turku, Finland) in 50 mM carbonate buffer, pH 9.8 for 4 hours at room temperature. Mixture was purified after reaction using two NAP-columns according to manufacturer's instructions and 50 mM Tris-HCl, 150 mM NaCl, 0.02% $NaN_3$, pH 7.75 as buffer.

For lateral flow test strips the HF180 nitrocellulose (Millipore) was printed for the test line with 0.6 mg/mL of Anti-Alkaline Phosphatase polyclonal antibody (Lifespan LS-C59288) using Linomat 5 printer (Camag, Switzerland). The lateral flow strips also had 16 mm width glass fiber sample pad (Millipore) and 24 mm width cellulose as adsorption pad (Millipore).

Quantitative lateral flow test was started by mixing 40 µL of microcystin or nodularin standards (FIG. 1A) at 1 µg/L in ionpurified water with 40 µL of antibody solution containing of 100 ng biotinylated Anti-ADDA Mab, 20 ng of SA51D1 or SA32C11 scFv-alkaline phosphatase fusion protein and $5 \times 10^6$ pieces of SA-UCNP in PBS, pH 7.4, 0.02% Tween20, 0.1% BSA buffer. For negative control, 40 µL of ionpurified water was used instead of CCPH standard. Each sample was measured as triplicate. Mixture was incubated for 10 minutes at room temperature. Lateral flow test strip was added to each sample, and incubated for 20 min to allow liquid to absorb to the test strip. Test strip was transferred to 100 µL of PBS, pH 7.4, 0.02% Tween20, 0.1% BSA buffer for washing of the strip. For time-resolved fluorescence measurement, a modified Chameleon 8 multilabel reader (Hidex, Turku, Finland) was used with 550 nm emission wavelength and 1 mm steps.

Figure 7:
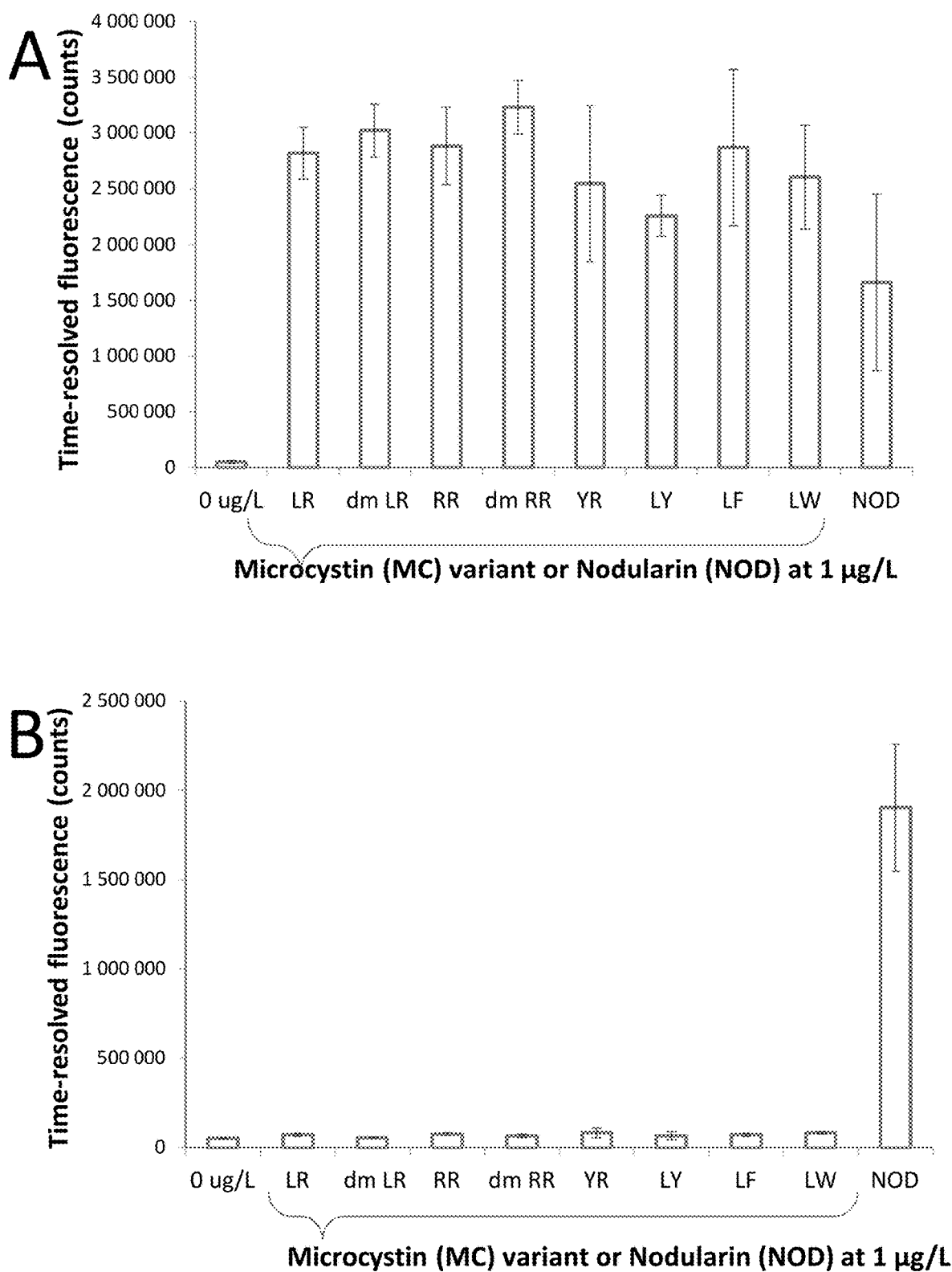
FIG. 7 illustrates the quantitative lateral flow test results for nine different cyanobacterial hepatotoxin variants (FIG. 1A) using two different secondary antibodies and streptavidin coated up-converting nanoparticles for signal formation. (A) SA51D1 as a secondary antibody recognizes all CCPH variants tested. (B) Only Nodularin was recognized using SA32C11 as a secondary antibody. For both figures, error bars for three replicates are shown. Each CCPH was tested at concentration of 1 µg/l.

The results in FIG. 7A show that all eight microcystin variants and nodularin are recognized by lateral flow test with signal-to-background ratio of >33 using SA51D1 as secondary antibody and FIG. 7B shows that only Nodularin was recognized using SA32C11 as secondary antibody with signal-to-background ratio of 38.

Example 5. Homogeneous Mix and Measure Assay

Figure 8:
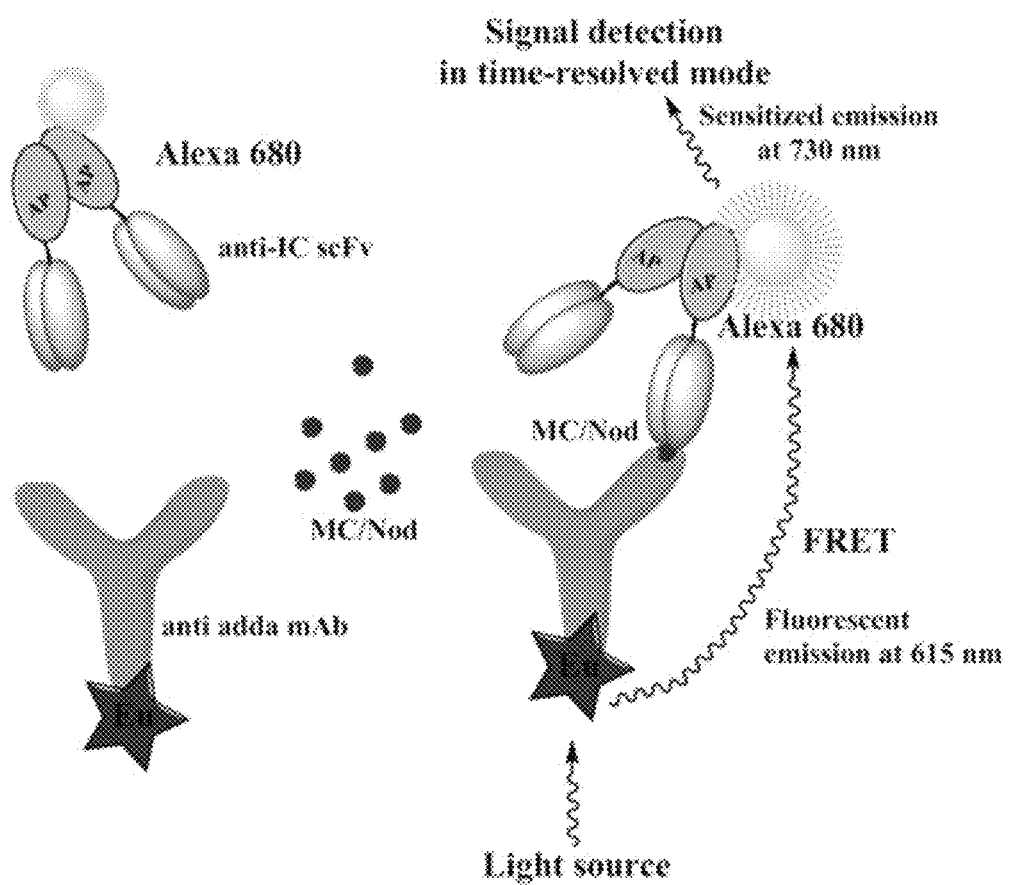
FIG. 8 shows the basic principle of the established homogenous non-competitive sandwich-type FRET immunoassay for CCPH. Eu-labeled Adda-specific monoclonal antibody and Alexa 680-labeled anti-IC scFv SA51D1 are added in water sample containing MCs/nods or not. In the absence of toxin the fluorophores are free in the solution and fluorescence is not detected. FRET occurs only at the close proximity of the two fluorophores when anti-IC scFv binds specifically to the anti-Adda mAb-MC/Nod IC.

This example demonstrates that the present anti-IC antibodies are also suitable for use in a homogeneous mix and measure type TR-FRET assay format. FIG. 8 illustrates the basic principle of the assay which is exemplified by employing anti-IC antibody SA51D1 labeled with Alexa 680 and an Adda-specific monoclonal antibody labelled with Eu-chelate.

The intrinsically luminescent heptadentate chelate (7d-EuIII) [2,2',2",2"'-[[4-[(4-isothiocyanatophenyl) ethynyl] pyridine-2,6-diyl] bis(methylenenitrilo)]tetrakis(acetato) europium(III)] was used (Takalo et al., 1994) to label the anti-Adda mAb for homogenous FRET assay. Anti adda mAb (700 µg) and a 100-fold molar excess of Eu(III) chelate was dissolved into a total volume of 438 µl of 50 mM carbonate buffer pH 9.8. The labeling reaction was incubated overnight at +4° C. while protected from light. The labeled antibody was purified with gel filtration with a Superdex 200 column and eluted in TSA buffer (50 mM Tris-HCl, pH 7.75, 150 mM NaCl, and 0.5 g L-1 $NaN_3$). The labeling degree of the purified product was determined. Euroium(III) chelate concentration in the labeled Eu(III) Adda mAb was measured by comparing the fluorescence of the purified product against a known Eu(III) standard. The Adda mAb concentration was measured by absorbance at 280 nm. In purified product, DTPA treated BSA was added to a final conc of 0.1% and filtered through 0.22 µm and stored at +4° C.

For conjugations of anti IC-scFv with Acceptor fluorophore 350 µg pure scFv SA51D1 was mixed with 8-fold molar excess of AF680 (dissolved in N,N-dimethylformamide from Sigma-Aldrich) in 50 mM carbonate buffer, pH 9.3 in 500 µL volume for 1 hour at room temperature. The labeled products were purified by double gel filtration using NAP5 and NAP10 columns from GE Healthcare and eluted in TSA, pH7.5 buffer. The labeling degrees of the purified products were measured by absorbance together with appropriate wavelengths and molar absorptivities of the acceptors (provided by the manufacturer).

Low-fluorescence yellow 96-well Maxisorp microtitration plates from Nunc (Roskilde, Denmark) were precoated with BSA prior to the assays with saturation solution containing 0.1% BSA (Bioreba, Switzerland) in presence of 0.1% (w/v) Germall II (ISP, Wayne, N.J.), and 3% (w/v) trehalose (Sigma-Aldrich, St. Louis, Mo.) in 0.05 M Tris-HCl, pH 7.2. Briefly 250 µl/well of saturation solution was added, incubated for 1 h at room temperature with slow shaking followed by aspiration of liquid. Plates were dried for 2 h and stored at +4° C. in sealed bag until used.

In BSA coated microtiter wells 20 µl/well of CCPH standard (stock concentration: 0-1000 µg/L) or sample were added in duplicates. Then reagent mixture consisting of Eu Adda mAb (15 ng) and Alexa 680 labeled scfv-AP (96 ng) was added as 60 µl/well making the total volume of each well 80 µl. Wells were then incubated for 2 to 30 min in room temperature with low shaking. At different time points, the sensitized emissions from AF680 generated by FRET were measured at 720 nm, with a Victor 1420 multilabel counter equipped with a red-sensitive Model R4632 photomultiplier tube (Hamamatsu Photonics, Hamamatsu, Japan) and 730 nm bandpass emission filter with a bandwidth of 10 nm and 70% transmission maximum (Nabburg, Interferenzoptik Elektronik GmbH, Germany). The excitation wavelength was 340 nm while the delay time and measuring time were 75 and 50 µs respectively.

Figure 9:
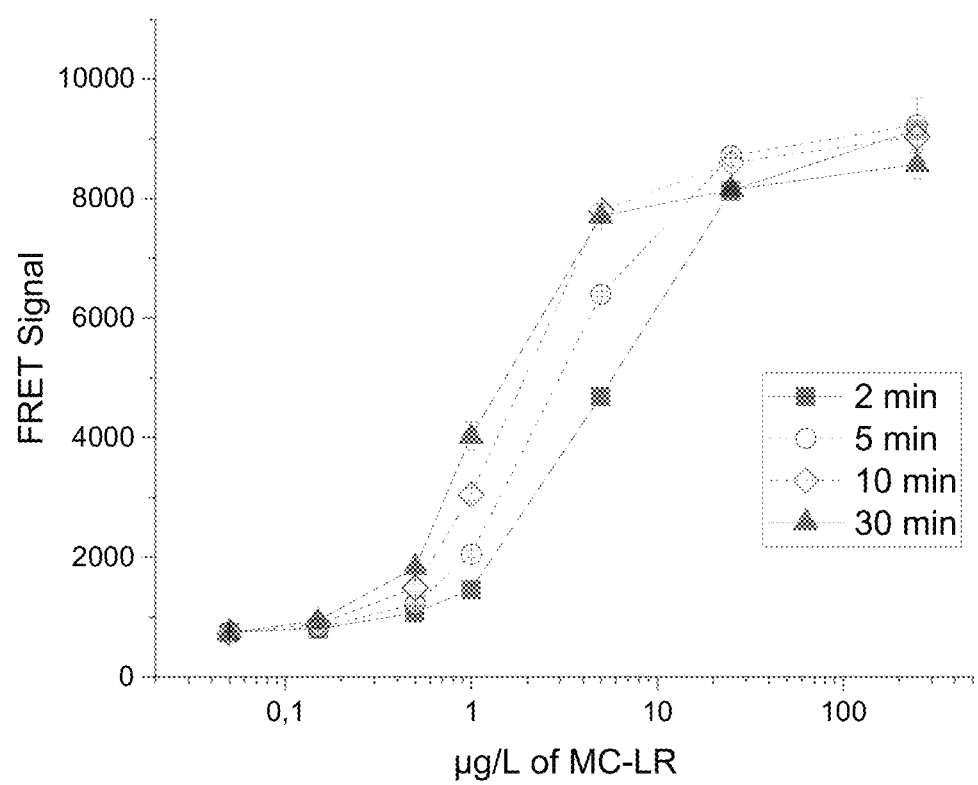
FIG. 9 exemplifies a homogeneous assay performed using Europium(III) labeled anti Adda-mAb as donor and SA51D1 anti-IC scFv conjugated with fluorescent dye AF680 as acceptor. In BSA coated microtiter wells, different concentration (0.05 to 250 µg/L) of MC-LR (plotted in logarithmic scale in X axis) was used to generate FRET signal (730 nm, plotted in Y axis) at different incubation time (2-30 min) points. Error bars of duplicate measurements are shown. The shortest (2 min) and the lengthiest (30 min) incubation time points are plotted as solid line. The sensitivity of the assay was found to be below 0.3 µg/L for MC-LR even within 2 min measurement.
Figure 10:
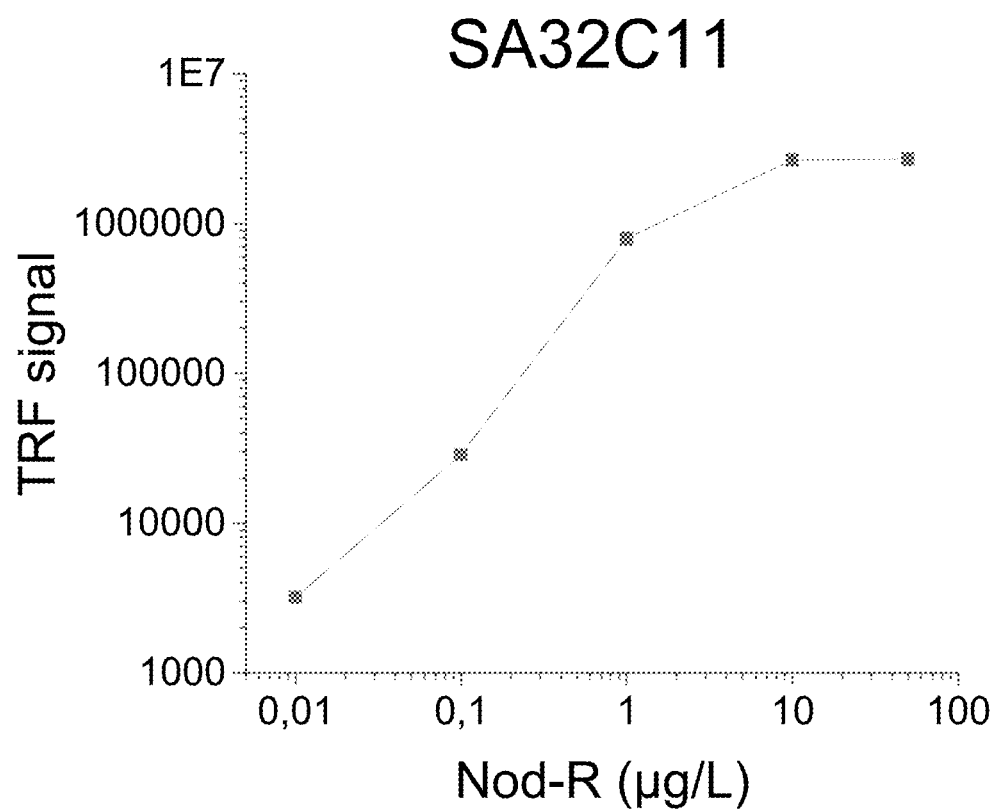
FIG. 10 illustrates the functionality of the IC assay with reversed capture. It shows standard curve for Nod-R using Nod specific binder SA32C11, where IC was captured on microtiter wells by binding of the secondary antibody SA32C11 to the solid phase using anti bAP pAb. Signal generation was performed by using Eu labelled anti Adda-mAb. Concentration of toxin (0.1-50 µg/L) are shown on X axis while the TRF signal is shown on Y Axis in logarithmic scale. Each point represents average of two replicates and error bars (as standard deviations) are shown.

The results shown in FIG. 9 demonstrate that MC-LR can be detected at concentrations below the World Health Organization guideline limit (1 µg/L of MC-LR) by a rapid (2-30 min) mix and measure homogenous assay without any washing steps. Using only 20 µl of a water sample in a 2 min-assay, the sensitivity (blank+3SD) for MC-LR was below 0.3 µg/L. The effect of incubation time on MC-LR standard was checked at different time points. Incubation times over 10 min seemed not to have any additional beneficiary effect.

Example 6. Functional Reversed Assay

This example demonstrates that the non-competetive assay may be performed also by capturing the IC-secondary antibody complex by using anti-AP pAb for immobilization.

Maxisorb microtiter plates were coated beforehand using 1 µg/200 µl/well of anti bAP pAb and stored dry at +4 C before use.

Anti bAP pAb coated wells were prewashed and saturated with Fab-AP (200 ng/200 µl/well) by 1 h at RT, followed by two washes. 90 µl of AB was added in each well. Nod-R standard stocks (in MQ) or blank (MQ) were added in duplicates as 10 µl/well. 100 µl of reagent mixture (prepared in AB containing Eu labelled Adda-mAb and SA32C11scFv-AP) was added (each component as 100 ng/well). Final concentration of standard in wells ranges from 0.01 to 50 µg/L. Wells were incubated at RT for 30 min with slow shaking followed by four washes. Finally Enhancement solution (ES) was added (200 µl/well) and after 5 min incubation, Eu signal was measured by VICTOR using Time Resolved Fluorometry.

Labeling of anti-Adda mAb with Eu(III) chelate was according as described in Example 5.

Example 7. Comparison of Anti-CCPH Antibodies Obtained by Immunization

Affinity and specificity of an IC binder antibody is the most crucial factor affecting an immunoassay performance. The IC binder should not recognize the primary antibody when antigen (CCPH) is not present, but should bind with high affinity when CCPH is present. Nagata et al (1999) show in FIG. 2 of their article that their best IC binder, a clone named 3F7, has severe problems to meet this requisite. This unwanted recognition is the most probable reason why Nagata describes very time-demanding (at least 40 hours containing 2-3 overnight incubations) immunoassay where long incubation times are needed to drive the kinetics of the assay to desired level. By comparison, we have shown that it is possible to generate an IC binder with minimal binding to naked primary antibody (FIG. 11) and this translates to very rapid and simple one-incubation step immunoassay with as low as 10 minute total incubation times.

By way of example, the specificity of SA51D1 to the immune complex was also seen in our immunoassay, where streptavidin-coated 96-well microtiter wells were used to capture a complex formed by biotinylated anti-Adda Mab, CCPH, SA51D1 antibody fused to alkaline phosphatase and this complex was detected with europium-labelled anti-alkaline phosphatase Pab. In this assay the background fluorescence signal level (biotinylated anti-Adda Mab, no CCPH, SA51D1 antibody fused to alkaline phosphatase and europium-labelled anti-alkaline phosphatase Pab) was extremely low, 404 counts which provides proof of insignificant binding of SA51D1 to anti-Adda Mab when CCPH is not present. With 10 µg/l level of MC-LR the fluorescence signal was 789966 counts. When seven other anti-IC antibody clones (SA56B8, SA55D1, SA51D12, SA41B5, SA42A3, SA44C11 and SA32C11) were tested together with SA51D1 clone in a corresponding immunoassay, their background fluorescence signal levels were similar (140-444 counts) thus proving them to be free of direct binding to anti-Adda Mab when no MC is present.

Example 8. Detection Results of Blinded Water Samples

The validity of CCPH-variant specific IC binding antibodies was evaluated by participation in the "Abraxis Microcystins proficiency testing program for recreational waters 2016-03" during April-August 2016. In this program 30 laboratories used their routine analysis methods to test four unknown water samples prepared by Abraxis Inc, Pennsylvania, USA. We used the assay described in Akter et al (2016) where broad-specific SA51D1 detected the four unknown samples correctly (table 1). The assay was also varied by using seven different anti-IC antibody variants to profile the unknown samples. The anti-IC antibodies tested were SA56B8 (MC-LR specific), SA55D1 (MC-LZ specific), SA51D12 (MC-LR and MC-LZ specific), SA41B5 (MC-RR specific), SA42A3 (MC-RR and MC-dmRR specific) and SA44C11 (MC-XR and Nod-R specific) and SA32C11 (nodularin-R specific). The results are shown in Table 3. For the first time, sample toxin profiles were correctly profiled with combination of seven anti-IC antibodies. MC-TK6 sample containing MC-RR and MC-YR (both at 1 µg/l) was found positive with clones SA41B5 (MC-RR specific), SA42A3 (MC-RR and MC-dmRR specific) and SA44C11 (MC-XR or Nod-R specific) and negative with other antibodies. Sample MC-TK7 containing 1 µg/l of MC-LR was positive with clones SA56B8 (MC-LR specific), SA55D1 (MC-LZ specific), SA51D12 (MC-LR and MC-LZ specific) and SA44C11 (MC-XR or Nod-R specific) and negative with other antibodies. Sample MC-TK8 contained 4 µg/l MC-LR, 1 µg/l MC-RR and 1 µg/l MC-YR and was found positive with antibodies SA56B8 (MC-LR specific), SA55D1 (MC-LZ specific), SA51D12 (MC-LR and MC-LZ specific), SA41B5 (MC-RR specific), SA42A3 (MC-RR and MC-dmRR specific) and SA44C11 (MC-XR or Nod-R specific) but not with Nod5 (nodularin specific). Sample MC-TK5 had no detectable microcystin and was negative with all tested immunoassay formats. This immunoassay combination allowed profiling water samples that have no detectable CCPH, have MC but not the most relevant MC congener MC-LR, have MC-LR in WHO guideline concentration of 1 µg/l, or have combination of several relevant MC congeners (MC-LR, MC-RR and MC-YR).

TABLE 3

CCPH profile of four unknown water samples.
Unknown samples were analyzed by anti-IC immunoassay using different anti-IC antibodies to reveal the CCPH profile of the samples.

| Unknown sample code | MC-TK5 | MC-TK6 | MC-TK7 | MC-TK8 |
|---|---|---|---|---|
| Certified CCPH content | none | MC-RR + MC-YR | MC-LR | MC-LR + MC-RR + MC-YR |
| Certified concentration (µg/l) | 0 | 1 + 1, total 2 | 1 | 4 + 1 + 1, total 6 |
| Specific anti-IC assay (clone) | | | | |
| Total CCPH, µg/l (SA51D1) | <LOD* | 1.88 | 1.38 | 6.57 |
| MC-LR? (SA56B8) | − | − | ++ | +++ |
| MC-LX? (SA55D1) | − | − | + | ++ |
| MC-LR or MC-LX? (SA51D12) | − | − | +++ | +++ |
| MC-RR? (SA41B5) | − | ++ | − | (+) |
| MC-RR or MC-dmRR? (SA42A3) | − | +++ | − | ++ |
| Nodularin? (SA32C11) | − | − | − | − |
| Interpretation | Negative | MC-RR | MC-LR ± MC-LX | MC-LR ± MC-LX |

Example 9. Cross-Reactivity Studies

Figure 12:
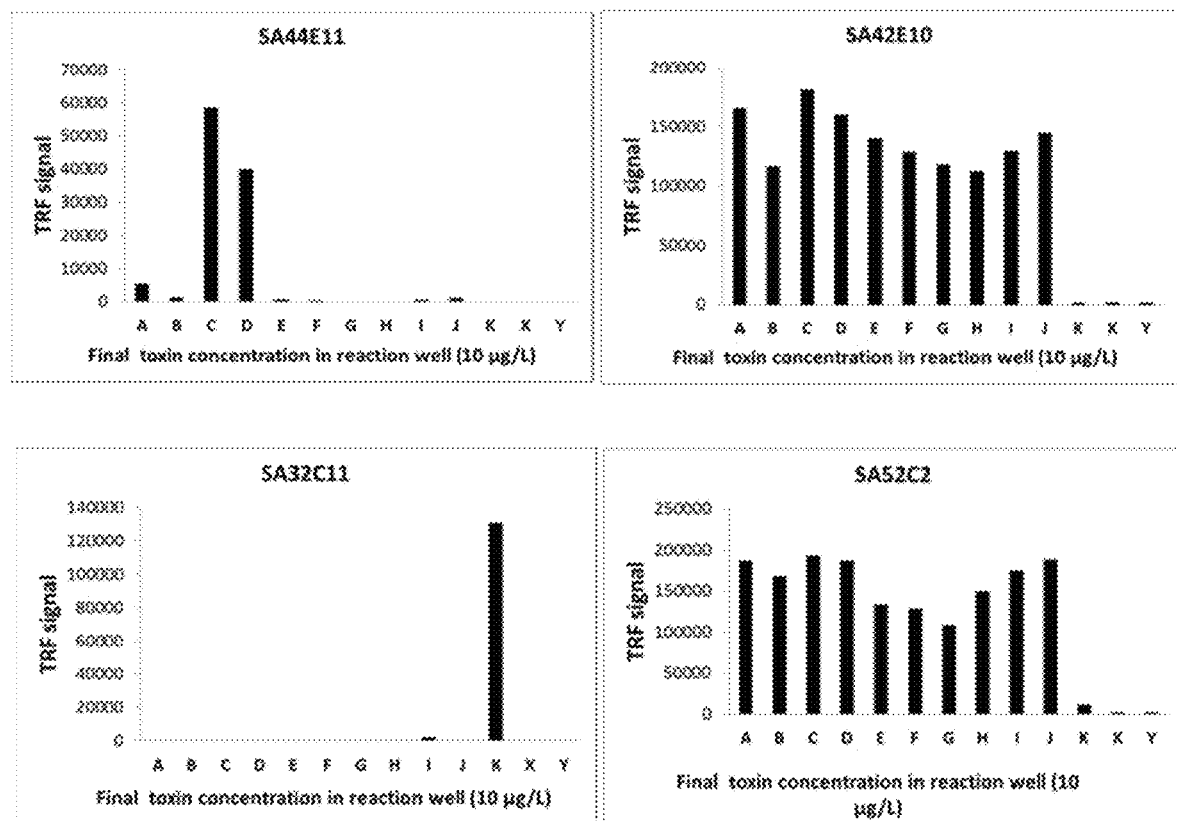
FIG. 12 shows reactivity data of exemplified anti-immunocomplex scFv-AP binders, namely SA51D1, SA51F6, SA56B8, SA59G2, SA56E7, SA51D12, SA57D4, SA56D5, SA41B5, SA42A3, SA44E11, SA32C11, SA32F1, SA34G1, SA42E10, SA52C2, SA55D1, SA51H4, SA58A12, SA33D5, SA41F2, and SA52B4.
Figure 12:
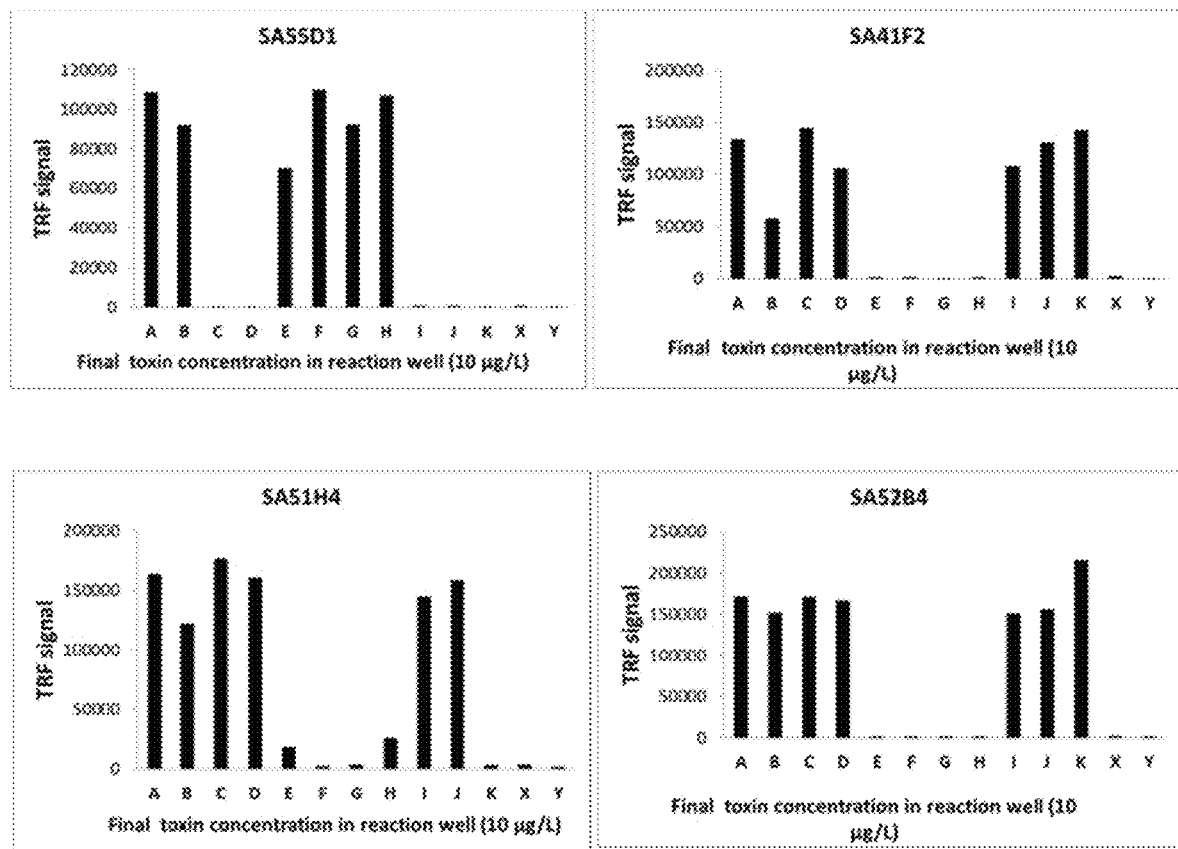
Figure 12:
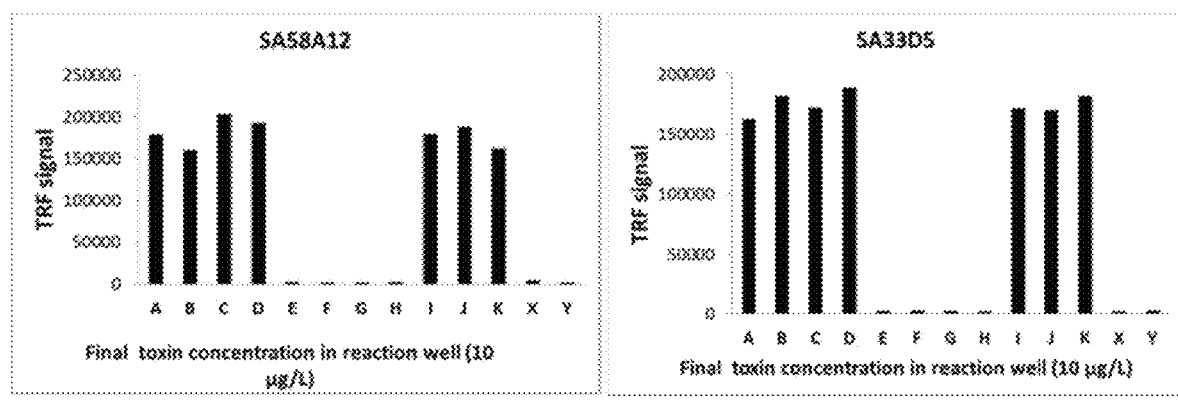

Anti-IC antibodies exemplified herein were subjected to cross-reactivity studies carried out as follows. In streptavidin coated well toxin standard solution (A=MC-LR, B=MC-dmLR, C=RR, D=MC-dmRR, E=MC-LA, F=MC-LY, G=MC-LF, H=MC-LW, I=MC-YR, J=MC-WR, K=Nodularin-R) (prepared in reagent water) of 20 µg/L were added as 50 µl per well (concentration of toxin becomes 10 µg/L in final 100 µl reaction well). For wells X and Y, 50 µl of reagent water was added instead of toxin. Then in each well, except in condition X, 25 µl (1 µg/ml solution) per well of biotinylated anti-Adda-mab was added. In well ×25 µl of assay buffer was used. After that, in each well 25 µl/well of scFv-AP (~2 µg/ml solution for His affinity pure scFv-AP, or diluted solution of crude sonicated culture extract) was added. Wells were then incubated for 30 to 40 min and washed for two times. Then in each well 100 µl per well (10 ng) of europium labeled bacterial anti alkaline phosphatase antibody was added. Wells were incubated for 1 h at RT (room temperature) and washed four times. Then europium fluorescence intensifier solution was added as 200 µl per well. Plates were incubated for at least five minute and time resolved fluorescence signal of Eu-chelate label was measured with a victor1420 Multilabel counter. The results of the cross-reactivity studies are shown in FIG. 12.

The invention claimed is:

1. An anti-immunocomplex (anti-IC) antibody, comprising:
   a region configured for specifically binding to an immunocomplex formed by one or more cyanobacterial cyclic peptide hepatotoxin (CCPH) variants and an anti-Adda antibody, wherein the CCPH variant is selected from the group consisting of MC-dmRR, MC-LY, MC-LF, MC-LW, MC-WR and Nod-R.

2. The anti-IC antibody according to claim 1, comprising:
   a light chain variable region with CDR1 having SEQ ID NO: 2, CDR2 having SEQ ID NO: 3, and CDR3 having SEQ ID NO: 4.

3. The anti-IC antibody according to claim 1, configured for specifically recognizing an immunocomplex formed between the anti-Adda antibody and a CPPH selected from the group consisting of MC-LR, MC-dmLR, MC-LA, MC-RR and MC-YR.

4. The anti-IC antibody according to claim 3, which is group-specific and configured to specifically recognize an immunocomplex formed between the anti-Adda antibody and at least CCPH variants MC-LR, MC-dmLR, MC-LA, MC-RR, MC-dmRR, MC-YR, MC-LY, MC-LF, MC-LW, MC-WR and Nod-R, the anti-IC antibody having a light chain variable region having CDRs 1-3 set forth in SEQ ID NO: 5, and a heavy chain variable region having CDRs 1-3 set forth in SEQ ID NO: 30.

5. The anti-IC antibody according to claim 4, comprising:
   a light chain variable region having SEQ ID NO: 5, and a heavy chain variable region having SEQ ID NO: 30.

6. The anti-IC antibody according to claim 3, which is group-specific and configured to specifically recognize an immunocomplex formed between the anti-Adda antibody and at least CCPH variants MC-LR, MC-dmLR, MC-LA, MC-RR, MC-dmRR, MC-YR, MC-LY, MC-LF, MC-LW, MC-WR and Nod-R, the anti-IC antibody having a light chain variable region having CDRs 1-3 set forth in SEQ ID NO: 6, and a heavy chain variable region having CDRs 1-3 set forth in SEQ ID NO: 31.

7. The anti-IC antibody according to claim 6, comprising:
   a light chain variable region having SEQ ID NO: 6, and a heavy chain variable region having SEQ ID NO: 31.

8. The anti-IC antibody according to claim 3, which is MC subgroup-specific and configured to specifically recognize an immunocomplex formed between the anti-Adda antibody and at least CCPH variants MC-LR, MC-dmLR, MC-LA, MC-RR, MC-dmRR, MC-YR, MC-LY, MC-LF, MC-LW, and MC-WR, the anti-IC antibody having a light chain variable region having CDRs 1-3 set forth in SEQ ID NO: 15 and a heavy chain variable region having CDRs 1-3 set forth SEQ ID NO: 40.

9. The anti-IC antibody according to claim 8, comprising:
   a light chain variable region having SEQ ID NO: 15, and a heavy chain variable region having SEQ ID NO: 40.

10. The anti-IC antibody according to claim 3, which is MC subgroup-specific and configured to specifically recognize an immunocomplex formed between the anti-Adda antibody and at least CCPH variants MC-LR, MC-dmLR, MC-LA, MC-RR, MC-dmRR, MC-YR, MC-LY, MC-LF, MC-LW, and MC-WR, the anti-IC antibody having a light chain variable region having CDRs 1-3 set forth in SEQ ID NOs: 16, and a heavy chain variable region having CDRs 1-3 set forth in SEQ ID NO: 41.

11. The anti-IC antibody according to claim 10, comprising:
a light chain variable region having SEQ ID NO: 16, and a heavy chain variable region having SEQ ID NO: 41.

12. The anti-IC antibody according to claim 3, which is MC-LZ subgroup-specific and configured to specifically recognize an immunocomplex formed between the anti-Adda antibody and at least CCPH variants MC-LR, dmMC-LR, MC-LY, MC-LF, MC-LA and MC-LW, the anti-IC antibody having a light chain variable region having CDRs 1-3 set forth in SEQ ID NOs: 17, and a heavy chain variable region comprising CDRs 1-3 set forth in SEQ ID NO: 42.

13. The anti-IC antibody according to claim 12, comprising:
a light chain variable region having SEQ ID NO: 17, and a heavy chain variable region having SEQ ID NO: 42.

14. The anti-IC antibody according to claim 3, which is MC-XR sub-group-specific and configured to specifically recognize an immunocomplex formed between the anti-Adda antibody and at least CCPH variants MC-LR, MC-RR, dmMC-RR, and MC-YR, the anti-IC antibody including:
a light chain variable region having CDRs 1-3 set forth in SEQ ID NO: 18, and a heavy chain variable region having CDRs 1-3 set forth in SEQ ID NO: 43; or
a light chain variable region having CDRs 1-3 set forth in SEQ ID NO: 19, and a heavy chain variable region having CDRs 1-3 set forth in SEQ ID NO: 44.

15. The anti-IC antibody according to claim 14, comprising:
a light chain variable region having SEQ ID NO: 18, and a heavy chain variable region having SEQ ID NO: 43; or
a light chain variable region comprising SEQ ID NO: 19, and a heavy chain variable region having SEQ ID NO: 44.

16. The anti-IC antibody according to claim 3, which is XR subgroup-specific and configured to specifically recognize an immunocomplex formed between the anti-Adda antibody and at least CCPH variants MC-LR, MC-RR, dmMC-RR, MC-YR, and Nod-R, the anti-IC antibody including:
a light chain variable region having CDRs 1-3 set forth in SEQ ID NO: 20, and a heavy chain variable region having CDRs 1-3 set forth in SEQ ID NO: 45; or
a light chain variable region having CDRs 1-3 set forth in SEQ ID NO: 21, and a heavy chain variable region having CDRs 1-3 set forth in SEQ ID NO: 46; or
a light chain variable region having CDRs 1-3 set forth in SEQ ID NO: 22, and a heavy chain variable region having CDRs 1-3 set forth in SEQ ID NO: 47; or
a light chain variable region having CDRs 1-3 set forth in SEQ ID NO: 23, and a heavy chain variable region having CDRs 1-3 set forth in SEQ ID NO: 48.

17. The anti-IC antibody according to claim 16, comprising:
a light chain variable region having SEQ ID NO: 20, and a heavy chain variable region having SEQ ID NO: 45; or
a light chain variable region having SEQ ID NO: 21, and a heavy chain variable region having SEQ ID NO: 46; or
a light chain variable region having SEQ ID NO: 22, and a heavy chain variable region having SEQ ID NO: 47; or
a light chain variable region having SEQ ID NOs: 23; and a heavy chain variable region having SEQ ID NO: 48.

18. The anti-IC antibody according to claim 1, which is MC-RR subgroup-specific and configured to specifically recognize an immunocomplex between the anti-Adda antibody and at least MC-RR and dmMC-RR, the anti-IC antibody comprising:
a light chain variable region having CDRs 1-3 set forth in SEQ ID NOs: 28; and a heavy chain variable region having CDRs 1-3 set forth in SEQ ID NO: 53; or
a light chain variable region having CDRs 1-3 set forth in SEQ ID NOs: 29; and a heavy chain variable region having CDRs 1-3 set forth in SEQ ID NO: 54.

19. The anti-IC antibody according to claim 18, comprising:
a light chain variable region having SEQ ID NOs: 28, and a heavy chain variable region having SEQ ID NO: 53; or
a light chain variable region having SEQ ID NOs: 29, and a heavy chain variable region having SEQ ID NO: 54.

20. The anti-IC antibody according to claim 1, which is Nod-R variant specific and configured to specifically recognize only an immunocomplex between the anti-Adda antibody and Nod-R, the anti-IC antibody having a light chain variable region having CDRs 1-3 set forth in SEQ ID NO: 12, and a heavy chain variable region having CDRs 1-3 set forth in SEQ ID NOs: 37.

21. The anti-IC antibody according to claim 20, comprising:
a light chain variable region having SEQ ID NO: 12, and a heavy chain variable region having SEQ ID NOs: 37.

22. The anti-IC antibody according to claim 1, which is Nod-R variant specific and configured to specifically recognize only an immunocomplex between the anti-Adda antibody and Nod-R, the anti-IC antibody having a light chain variable region having CDRs 1-3 set forth in SEQ ID NO: 13, and a heavy chain variable region having CDRs 1-3 set forth in SEQ ID NOs: 38.

23. The anti-IC antibody according to claim 22, comprising: a light chain variable region having SEQ ID NO: 13, and a heavy chain variable region having SEQ ID NOs: 38.

24. The anti-IC antibody according to claim 1, which is Nod-R variant specific and configured to specifically recognize only an immunocomplex between the anti-Adda antibody and Nod-R, the anti-IC antibody having a light chain variable region having CDRs 1-3 set forth in SEQ ID NO: 14, and a heavy chain variable region having CDRs 1-3 set forth in SEQ ID NOs: 39.

25. The anti-IC antibody according to claim 24, comprising: a light chain variable region having SEQ ID NO: 14, and a heavy chain variable region having SEQ ID NOs: 39.

26. The antibody according to claim 1, wherein the antibody is configured as a recombinant antibody or a fragment thereof, including as a Fab, Fab', F(ab')2, Fv or scFv fragment.

27. The antibody according to claim 26, wherein the antibody is configured as a scFv fragment comprising:
a linker peptide which includes an amino acid sequence depicted in SEQ ID NO:1 or a conservative sequence variant thereof or a variant having at least 80% sequence identity with SEQ ID NO:1.

28. A set of anti-IC antibodies comprising:
at least two antibodies according to claim 1.

29. The set according to claim 28, comprising:
at least one group-specific antibody selected from the group consisting of antibodies which include a light chain variable region having an amino acid sequence selected from the group consisting of SEQ ID NOs: 5-6, and a respective heavy chain variable region having an amino acid sequence selected from the group consisting of SEQ ID NOs: 30-31; and at least one other antibody selected from the group consisting of antibodies including a light chain variable region having an amino acid sequence selected from the group consisting of SEQ ID NOs: 7-29, and a respective heavy chain variable region having an amino acid sequence selected from the group consisting of SEQ ID NOs: 32-54.

30. A method for the preparation of an anti-immunocomplex (anti-IC) antibody, including a region configured for specifically binding to an immunocomplex formed by one or more cyanobacterial cyclic peptide hepatotoxin (CCPH) variants and an anti-Adda antibody, wherein the CCPH variant is selected from the group consisting of MC-dmRR, MC-LY, MC-LF, MC-LW, MC-WR and Nod-R, wherein the method comprises:

obtaining the antibody from a recombinant expression library by selecting an antibody that binds to an immunocomplex of one or more CCPH variants and an anti-Adda primary antibody, wherein the CCPH variant is selected from the group consisting of MC-LR, MC-dmLR, MC-LA, MC-RR, MC-dmRR, MC-YR, MC-LY, MC-LF, MC-LW, MC-WR and Nod-R.

31. The method according to claim 30, wherein recombinant anti-IC antibody fragments are prepared from a phage display library.

32. The method according to claim 30, wherein a primary antibody without a CCPH is used for negative selection to select an anti-IC antibody that recognizes the immunocomplex but not free primary antibody nor free CCPH.

33. The method according to claim 31, wherein the display phages are first preincubated with a bound primary antibody to sort out those antibodies binding to the primary antibody as such, whereafter unbound phages are separated and incubated with a mixture of CCPH and immobilised primary antibody to select phages that bind to the immunocomplex formed between the immobilized primary antibody and CCPH, but not to the primary antibody as such.

34. An anti-IC antibody obtained by the method according to claim 30.

35. An immunoassay for detecting one or more CCPH variants in an aqueous sample, comprising:

a) reacting the sample with a set of antibodies including at least an anti-immunocomplex (anti-IC) antibody, including a region configured for specifically binding to an immunocomplex formed by one or more cyanobacterial cyclic peptide hepatotoxin (CCPH) variants and an anti-Adda antibody, wherein the CCPH variant is selected from the group consisting of MC-dmRR, MC-LY, MC-LF, MC-LW, MC-WR and Nod-R and an anti-Adda primary antibody, wherein said anti-Adda primary antibody binds to the one or more CCPH variants present in the sample, if any, and forms an immunocomplex therewith, and wherein said at least one anti-IC antibody binds specifically to said immunocomplex forming a sandwiched immunocomplex; and b) detecting presence or absence of said sandwiched immunocomplex indicating the presence or absence of said one or more CCPH variants in said sample, respectively.

36. The assay according to claim 35, which is a non-competitive homogeneous immunoassay.

37. The assay according to claim 35, which is a non-competitive heterogeneous immunoassay.

38. A method comprising:

providing an anti-immunocomplex (anti-IC) antibody, including a region configured for specifically binding to an immunocomplex formed by one or more cyanobacterial cyclic peptide hepatotoxin (CCPH) variants and an anti-Adda antibody, wherein the CCPH variant is selected from the group consisting of MC-dmRR, MC-LY, MC-LF, MC-LW, MC-WR and Nod-R; and detecting the presence or absence of one or more CCPH variants in an aqueous sample.

39. The method according to claim 38, wherein said aqueous sample is a water sample, selected from the group consisting of a drinking water sample, a well water sample, a recreational water sample, a bathing water sample, and an environmental water sample.

40. A kit for detecting one or more CCPH variants in an aqueous sample, comprising:

an anti-immunocomplex (anti-IC) antibody, including a region configured for specifically binding to an immunocomplex formed by one or more cyanobacterial cyclic peptide hepatotoxin (CCPH) variants and an anti-Adda antibody, wherein the CCPH variant is selected from the group consisting of MC-dmRR, MC-LY, MC-LF, MC-LW, MC-WR and Nod-R.

41. The kit according to claim 40, comprising:

an anti-CCPH antibody.

42. The kit according to claim 40, comprising:

one or more components for carrying out an immunoassay, selected from the group consisting of blots, microtiter plates, reaction vials, lateral flow strips, appropriate standards, buffers, detection reagents, and wash solutions.

* * * * *

SEQUENCE LISTING

```
<160> NUMBER OF SEQ ID NOS: 54

<210> SEQ ID NO 1
<211> LENGTH: 20
<212> TYPE: PRT
<213> ORGANISM: Artificial Sequence
<220> FEATURE:
<223> OTHER INFORMATION: Peptide linker

<400> SEQUENCE: 1

Gly Gly Gly Gly Ser Gly Ala Gly Gly Ser Gly Gly Gly Gly Thr Gly
1               5                   10                  15

Gly Gly Gly Ser
            20

<210> SEQ ID NO 2
<211> LENGTH: 12
<212> TYPE: PRT
<213> ORGANISM: Artificial Sequence
<220> FEATURE:
<223> OTHER INFORMATION: LCDR1
<220> FEATURE:
<221> NAME/KEY: MISC_FEATURE
<222> LOCATION: (10)..(10)
<223> OTHER INFORMATION: Xaa is N, A, or Y

<400> SEQUENCE: 2

Arg Ala Ser Gln Ser Val Ser Ser Xaa Leu Ala
1               5                   10

<210> SEQ ID NO 3
<211> LENGTH: 7
<212> TYPE: PRT
<213> ORGANISM: Artificial Sequence
<220> FEATURE:
<223> OTHER INFORMATION: LCDR2

<400> SEQUENCE: 3
```

```
Gly Ala Ser Ser Arg Ala Thr
1               5

<210> SEQ ID NO 4
<211> LENGTH: 9
<212> TYPE: PRT
<213> ORGANISM: Artificial Sequence
<220> FEATURE:
<223> OTHER INFORMATION: LCDR3
<220> FEATURE:
<221> NAME/KEY: MISC_FEATURE
<222> LOCATION: (3)..(3)
<223> OTHER INFORMATION: Xaa is Y, S, or M
<220> FEATURE:
<221> NAME/KEY: MISC_FEATURE
<222> LOCATION: (4)..(4)
<223> OTHER INFORMATION: Xaa is S, Y, or H
<220> FEATURE:
<221> NAME/KEY: MISC_FEATURE
<222> LOCATION: (6)..(6)
<223> OTHER INFORMATION: Xaa is T, Y, L

<400> SEQUENCE: 4

Gln Gln Xaa Xaa Ser Xaa Pro Trp Thr
1               5

<210> SEQ ID NO 5
<211> LENGTH: 110
<212> TYPE: PRT
<213> ORGANISM: Artificial Sequence
<220> FEATURE:
<223> OTHER INFORMATION: Clone SA51D1
<220> FEATURE:
<221> NAME/KEY: DOMAIN
<222> LOCATION: (24)..(35)
<223> OTHER INFORMATION: CDR1
<220> FEATURE:
<221> NAME/KEY: DOMAIN
<222> LOCATION: (51)..(57)
<223> OTHER INFORMATION: CDR2
<220> FEATURE:
<221> NAME/KEY: DOMAIN
<222> LOCATION: (90)..(98)
<223> OTHER INFORMATION: CDR3

<400> SEQUENCE: 5

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Asn Leu Ala Trp Tyr Gln Gln Lys Pro Gly Gln Ala Pro Arg Leu Leu
        35                  40                  45

Ile Tyr Gly Ala Ser Ser Arg Ala Thr Gly Val Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Met His Ser Thr Pro
                85                  90                  95

Trp Thr Phe Gly Gln Gly Thr Lys Val Glu Ile Lys Arg Thr
            100                 105                 110

<210> SEQ ID NO 6
<211> LENGTH: 110
<212> TYPE: PRT
<213> ORGANISM: Artificial Sequence
<220> FEATURE:
<223> OTHER INFORMATION: Clone SA51F6
```

```
<220> FEATURE:
<221> NAME/KEY: DOMAIN
<222> LOCATION: (24)..(35)
<223> OTHER INFORMATION: CDR1
<220> FEATURE:
<221> NAME/KEY: DOMAIN
<222> LOCATION: (51)..(57)
<223> OTHER INFORMATION: CDR2
<220> FEATURE:
<221> NAME/KEY: DOMAIN
<222> LOCATION: (90)..(98)
<223> OTHER INFORMATION: CDR3

<400> SEQUENCE: 6

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Val Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Ser Ser Ser Thr Pro
                85                  90                  95

Trp Thr Phe Gly Gln Gly Thr Lys Val Glu Ile Lys Arg Thr
            100                 105                 110

<210> SEQ ID NO 7
<211> LENGTH: 110
<212> TYPE: PRT
<213> ORGANISM: Artificial Sequence
<220> FEATURE:
<223> OTHER INFORMATION: Clone SA56B8
<220> FEATURE:
<221> NAME/KEY: DOMAIN
<222> LOCATION: (24)..(35)
<223> OTHER INFORMATION: CDR1
<220> FEATURE:
<221> NAME/KEY: DOMAIN
<222> LOCATION: (51)..(57)
<223> OTHER INFORMATION: CDR2
<220> FEATURE:
<221> NAME/KEY: DOMAIN
<222> LOCATION: (90)..(98)
<223> OTHER INFORMATION: CDR3

<400> SEQUENCE: 7

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Val Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Ser Ser Ser Tyr Pro
                85                  90                  95

Trp Thr Phe Gly Gln Gly Thr Lys Val Glu Ile Lys Arg Thr
            100                 105                 110
```

```
<210> SEQ ID NO 8
<211> LENGTH: 110
<212> TYPE: PRT
<213> ORGANISM: Artificial Sequence
<220> FEATURE:
<223> OTHER INFORMATION: Clone SA59G2
<220> FEATURE:
<221> NAME/KEY: DOMAIN
<222> LOCATION: (24)..(35)
<223> OTHER INFORMATION: CDR1
<220> FEATURE:
<221> NAME/KEY: DOMAIN
<222> LOCATION: (51)..(57)
<223> OTHER INFORMATION: CDR2
<220> FEATURE:
<221> NAME/KEY: DOMAIN
<222> LOCATION: (90)..(98)
<223> OTHER INFORMATION: CDR3

<400> SEQUENCE: 8

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Ala Leu Ala Trp Tyr Gln Gln Lys Pro Gly Gln Ala Pro Arg Leu Leu
        35                  40                  45

Ile Tyr Gly Ala Ser Ser Arg Ala Thr Gly Val Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Ser Ser Ser Leu Pro
                85                  90                  95

Trp Thr Phe Gly Gln Gly Thr Lys Val Glu Ile Lys Arg Thr
            100                 105                 110

<210> SEQ ID NO 9
<211> LENGTH: 110
<212> TYPE: PRT
<213> ORGANISM: Artificial Sequence
<220> FEATURE:
<223> OTHER INFORMATION: Clone SA56E7
<220> FEATURE:
<221> NAME/KEY: DOMAIN
<222> LOCATION: (24)..(35)
<223> OTHER INFORMATION: CDR1
<220> FEATURE:
<221> NAME/KEY: DOMAIN
<222> LOCATION: (51)..(57)
<223> OTHER INFORMATION: CDR2
<220> FEATURE:
<221> NAME/KEY: DOMAIN
<222> LOCATION: (90)..(98)
<223> OTHER INFORMATION: CDR3

<400> SEQUENCE: 9

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Asn Leu Ala Trp Tyr Gln Gln Lys Pro Gly Gln Ala Pro Arg Leu Leu
        35                  40                  45

Ile Tyr Gly Ala Ser Ser Arg Ala Thr Gly Val Pro Asp Arg Phe Ser
    50                  55                  60

Gly Ser Gly Ser Gly Thr Asp Phe Thr Leu Thr Ile Ser Arg Leu Glu
65                  70                  75                  80
```

```
Pro Glu Asp Phe Ala Val Tyr Tyr Cys Gln Gln Ser Tyr Ser Tyr Pro
                85                  90                  95

Trp Thr Phe Gly Gln Gly Thr Lys Val Glu Ile Lys Arg Thr
            100                 105                 110

<210> SEQ ID NO 10
<211> LENGTH: 109
<212> TYPE: PRT
<213> ORGANISM: Artificial Sequence
<220> FEATURE:
<223> OTHER INFORMATION: Clone SA51D12
<220> FEATURE:
<221> NAME/KEY: DOMAIN
<222> LOCATION: (24)..(35)
<223> OTHER INFORMATION: CDR1
<220> FEATURE:
<221> NAME/KEY: DOMAIN
<222> LOCATION: (51)..(57)
<223> OTHER INFORMATION: CDR2
<220> FEATURE:
<221> NAME/KEY: DOMAIN
<222> LOCATION: (90)..(98)
<223> OTHER INFORMATION: CDR3

<400> SEQUENCE: 10

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Asn Leu Ala Trp Tyr Gln Gln Lys Pro Gly Gln Ala Pro Arg Leu Leu
        35                  40                  45

Ile Tyr Gly Ala Ser Ser Arg Ala Thr Gly Val Pro Asp Arg Phe Ser
50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Ser Ser Thr Pro Trp
                85                  90                  95

Thr Phe Gly Gln Gly Thr Lys Val Glu Ile Lys Arg Thr
            100                 105

<210> SEQ ID NO 11
<211> LENGTH: 110
<212> TYPE: PRT
<213> ORGANISM: Artificial Sequence
<220> FEATURE:
<223> OTHER INFORMATION: Clone SA41B5
<220> FEATURE:
<221> NAME/KEY: DOMAIN
<222> LOCATION: (24)..(35)
<223> OTHER INFORMATION: CDR1
<220> FEATURE:
<221> NAME/KEY: DOMAIN
<222> LOCATION: (51)..(57)
<223> OTHER INFORMATION: CDR2
<220> FEATURE:
<221> NAME/KEY: DOMAIN
<222> LOCATION: (90)..(98)
<223> OTHER INFORMATION: CDR3

<400> SEQUENCE: 11

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Asn Leu Ala Trp Tyr Gln Gln Lys Pro Gly Gln Ala Pro Arg Leu Leu
```

-continued

```
                35                  40                  45
Ile Tyr Gly Ala Ser Ser Arg Ala Thr Gly Val Pro Asp Arg Phe Ser
        50                  55                  60
Gly Ser Gly Ser Gly Thr Asp Phe Thr Leu Thr Ile Ser Arg Leu Glu
 65                  70                  75                  80
Pro Glu Asp Phe Ala Val Tyr Tyr Cys Gln Gln Ser Ser Ser Leu Pro
                85                  90                  95
Trp Thr Phe Gly Gln Gly Thr Lys Val Glu Ile Lys Arg Thr
            100                 105                 110
```

<210> SEQ ID NO 12
<211> LENGTH: 110
<212> TYPE: PRT
<213> ORGANISM: Artificial Sequence
<220> FEATURE:
<223> OTHER INFORMATION: Clone SA32C11
<220> FEATURE:
<221> NAME/KEY: DOMAIN
<222> LOCATION: (24)..(35)
<223> OTHER INFORMATION: CDR1
<220> FEATURE:
<221> NAME/KEY: DOMAIN
<222> LOCATION: (51)..(57)
<223> OTHER INFORMATION: CDR2
<220> FEATURE:
<221> NAME/KEY: DOMAIN
<222> LOCATION: (90)..(98)
<223> OTHER INFORMATION: CDR3

<400> SEQUENCE: 12

```
Glu Ile Val Leu Thr Gln Ser Pro Gly Thr Leu Ser Leu Ser Pro Gly
 1               5                  10                  15
Glu Arg Ala Thr Leu Ser Cys Arg Ala Ser Gln Ser Val Ser Ser Ser
                20                  25                  30
Asn Leu Ala Trp Tyr Gln Gln Lys Pro Gly Gln Ala Pro Arg Leu Leu
                35                  40                  45
Ile Tyr Gly Ala Ser Ser Arg Ala Thr Gly Val Pro Asp Arg Phe Ser
        50                  55                  60
Gly Ser Gly Ser Gly Thr Asp Phe Thr Leu Thr Ile Ser Arg Leu Glu
 65                  70                  75                  80
Pro Glu Asp Phe Ala Val Tyr Tyr Cys Gln Gln Ser Ser Ser Leu Pro
                85                  90                  95
Trp Thr Phe Gly Gln Gly Thr Lys Val Glu Ile Lys Arg Thr
            100                 105                 110
```

<210> SEQ ID NO 13
<211> LENGTH: 110
<212> TYPE: PRT
<213> ORGANISM: Artificial Sequence
<220> FEATURE:
<223> OTHER INFORMATION: Clone SA32F1
<220> FEATURE:
<221> NAME/KEY: DOMAIN
<222> LOCATION: (24)..(35)
<223> OTHER INFORMATION: CDR1
<220> FEATURE:
<221> NAME/KEY: DOMAIN
<222> LOCATION: (51)..(57)
<223> OTHER INFORMATION: CDR2
<220> FEATURE:
<221> NAME/KEY: DOMAIN
<222> LOCATION: (90)..(98)
<223> OTHER INFORMATION: CDR3

<400> SEQUENCE: 13

```
Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Ala Leu Ala Trp Tyr Gln Gln Lys Pro Gly Gln Ala Pro Arg Leu Leu
        35                  40                  45

Ile Tyr Gly Ala Ser Ser Arg Ala Thr Gly Val Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Ser Ser Ser Tyr Pro
                85                  90                  95

Trp Thr Phe Gly Gln Gly Thr Lys Val Glu Ile Lys Arg Thr
            100                 105                 110
```

<210> SEQ ID NO 14
<211> LENGTH: 110
<212> TYPE: PRT
<213> ORGANISM: Artificial Sequence
<220> FEATURE:
<223> OTHER INFORMATION: Clone SA34G1
<220> FEATURE:
<221> NAME/KEY: DOMAIN
<222> LOCATION: (24)..(35)
<223> OTHER INFORMATION: CDR1
<220> FEATURE:
<221> NAME/KEY: DOMAIN
<222> LOCATION: (51)..(57)
<223> OTHER INFORMATION: CDR2
<220> FEATURE:
<221> NAME/KEY: DOMAIN
<222> LOCATION: (90)..(98)
<223> OTHER INFORMATION: CDR3

<400> SEQUENCE: 14

```
Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Asn Leu Ala Trp Tyr Gln Gln Lys Pro Gly Gln Ala Pro Arg Leu Leu
        35                  40                  45

Ile Tyr Gly Ala Ser Ser Arg Ala Thr Gly Val Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Ser Ser Ser Thr Pro
                85                  90                  95

Trp Thr Phe Gly Gln Gly Thr Lys Val Glu Ile Lys Arg Thr
            100                 105                 110
```

<210> SEQ ID NO 15
<211> LENGTH: 110
<212> TYPE: PRT
<213> ORGANISM: Artificial Sequence
<220> FEATURE:
<223> OTHER INFORMATION: Clone SA42E10
<220> FEATURE:
<221> NAME/KEY: DOMAIN
<222> LOCATION: (24)..(35)
<223> OTHER INFORMATION: CDR1
<220> FEATURE:
<221> NAME/KEY: DOMAIN
<222> LOCATION: (51)..(57)
<223> OTHER INFORMATION: CDR2

<220> FEATURE:
<221> NAME/KEY: DOMAIN
<222> LOCATION: (90)..(98)
<223> OTHER INFORMATION: CDR3

<400> SEQUENCE: 15

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Val Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Ser Ser Ser Leu Pro
                85                  90                  95

Trp Thr Phe Gly Gln Gly Thr Lys Val Glu Ile Lys Arg Thr
            100                 105                 110

<210> SEQ ID NO 16
<211> LENGTH: 110
<212> TYPE: PRT
<213> ORGANISM: Artificial Sequence
<220> FEATURE:
<223> OTHER INFORMATION: Clone SA52C2
<220> FEATURE:
<221> NAME/KEY: DOMAIN
<222> LOCATION: (24)..(35)
<223> OTHER INFORMATION: CDR1
<220> FEATURE:
<221> NAME/KEY: DOMAIN
<222> LOCATION: (51)..(57)
<223> OTHER INFORMATION: CDR2
<220> FEATURE:
<221> NAME/KEY: DOMAIN
<222> LOCATION: (90)..(98)
<223> OTHER INFORMATION: CDR3

<400> SEQUENCE: 16

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser
            20                  25                  30

Asn Leu Ala Trp Tyr Gln Gln Lys Pro Gly Gln Ala Pro Arg Leu Leu
        35                  40                  45

Ile Tyr Gly Ala Ser Ser Arg Ala Thr Gly Val Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Met His Ser Thr Pro
                85                  90                  95

Trp Thr Phe Gly Gln Gly Thr Lys Val Glu Ile Lys Arg Thr
            100                 105                 110

<210> SEQ ID NO 17
<211> LENGTH: 110
<212> TYPE: PRT
<213> ORGANISM: Artificial Sequence
<220> FEATURE:
<223> OTHER INFORMATION: Clone SA55D1
<220> FEATURE:

```
<221> NAME/KEY: DOMAIN
<222> LOCATION: (24)..(35)
<223> OTHER INFORMATION: CDR1
<220> FEATURE:
<221> NAME/KEY: DOMAIN
<222> LOCATION: (51)..(57)
<223> OTHER INFORMATION: CDR2
<220> FEATURE:
<221> NAME/KEY: DOMAIN
<222> LOCATION: (90)..(98)
<223> OTHER INFORMATION: CDR3

<400> SEQUENCE: 17

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Ala Leu Ala Trp Tyr Gln Gln Lys Pro Gly Gln Ala Pro Arg Leu Leu
        35                  40                  45

Ile Tyr Gly Ala Ser Ser Arg Ala Thr Gly Val Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Ser Tyr Ser Tyr Pro
                85                  90                  95

Trp Thr Phe Gly Gln Gly Thr Lys Val Glu Ile Lys Arg Thr
            100                 105                 110

<210> SEQ ID NO 18
<211> LENGTH: 110
<212> TYPE: PRT
<213> ORGANISM: Artificial Sequence
<220> FEATURE:
<223> OTHER INFORMATION: Clone SA51H4
<220> FEATURE:
<221> NAME/KEY: DOMAIN
<222> LOCATION: (24)..(35)
<223> OTHER INFORMATION: CDR1
<220> FEATURE:
<221> NAME/KEY: DOMAIN
<222> LOCATION: (51)..(57)
<223> OTHER INFORMATION: CDR2
<220> FEATURE:
<221> NAME/KEY: DOMAIN
<222> LOCATION: (90)..(98)
<223> OTHER INFORMATION: CDR3

<400> SEQUENCE: 18

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Asn Leu Ala Trp Tyr Gln Gln Lys Pro Gly Gln Ala Pro Arg Leu Leu
        35                  40                  45

Ile Tyr Gly Ala Ser Ser Arg Ala Thr Gly Val Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Ser Ser Ser Tyr Pro
                85                  90                  95

Trp Thr Phe Gly Gln Gly Thr Lys Val Glu Ile Lys Arg Thr
            100                 105                 110
```

```
<210> SEQ ID NO 19
<211> LENGTH: 110
<212> TYPE: PRT
<213> ORGANISM: Artificial Sequence
<220> FEATURE:
<223> OTHER INFORMATION: Clone SA41A5
<220> FEATURE:
<221> NAME/KEY: DOMAIN
<222> LOCATION: (24)..(35)
<223> OTHER INFORMATION: CDR1
<220> FEATURE:
<221> NAME/KEY: DOMAIN
<222> LOCATION: (51)..(57)
<223> OTHER INFORMATION: CDR2
<220> FEATURE:
<221> NAME/KEY: DOMAIN
<222> LOCATION: (90)..(98)
<223> OTHER INFORMATION: CDR3

<400> SEQUENCE: 19

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Ala Leu Ala Trp Tyr Gln Gln Lys Pro Gly Gln Ala Pro Arg Leu Leu
        35                  40                  45

Ile Tyr Gly Ala Ser Ser Arg Ala Thr Gly Val Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Met His Ser Thr Pro
                85                  90                  95

Trp Thr Phe Gly Gln Gly Thr Lys Val Glu Ile Lys Arg Thr
            100                 105                 110

<210> SEQ ID NO 20
<211> LENGTH: 110
<212> TYPE: PRT
<213> ORGANISM: Artificial Sequence
<220> FEATURE:
<223> OTHER INFORMATION: Clone SA58A12
<220> FEATURE:
<221> NAME/KEY: DOMAIN
<222> LOCATION: (24)..(35)
<223> OTHER INFORMATION: CDR1
<220> FEATURE:
<221> NAME/KEY: DOMAIN
<222> LOCATION: (51)..(57)
<223> OTHER INFORMATION: CDR2
<220> FEATURE:
<221> NAME/KEY: DOMAIN
<222> LOCATION: (90)..(98)
<223> OTHER INFORMATION: CDR3

<400> SEQUENCE: 20

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Asn Leu Ala Trp Tyr Gln Gln Lys Pro Gly Gln Ala Pro Arg Leu Leu
        35                  40                  45

Ile Tyr Gly Ala Ser Ser Arg Ala Thr Gly Val Pro Asp Arg Phe Ser
    50                  55                  60

Gly Ser Gly Ser Gly Thr Asp Phe Thr Leu Thr Ile Ser Arg Leu Glu
65                  70                  75                  80
```

```
Pro Glu Asp Phe Ala Val Tyr Tyr Cys Gln Gln Ser Ser Tyr Pro
            85                  90                  95

Trp Thr Phe Gly Gln Gly Thr Lys Val Glu Ile Lys Arg Thr
            100                 105                 110

<210> SEQ ID NO 21
<211> LENGTH: 110
<212> TYPE: PRT
<213> ORGANISM: Artificial Sequence
<220> FEATURE:
<223> OTHER INFORMATION: Clone SA33D5
<220> FEATURE:
<221> NAME/KEY: DOMAIN
<222> LOCATION: (24)..(35)
<223> OTHER INFORMATION: CDR1
<220> FEATURE:
<221> NAME/KEY: DOMAIN
<222> LOCATION: (51)..(57)
<223> OTHER INFORMATION: CDR2
<220> FEATURE:
<221> NAME/KEY: DOMAIN
<222> LOCATION: (90)..(98)
<223> OTHER INFORMATION: CDR3

<400> SEQUENCE: 21

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser
            20                  25                  30

Asn Leu Ala Trp Tyr Gln Gln Lys Pro Gly Gln Ala Pro Arg Leu Leu
            35                  40                  45

Ile Tyr Gly Ala Ser Ser Arg Ala Thr Gly Val Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Ser Ser Tyr Pro
            85                  90                  95

Trp Thr Phe Gly Gln Gly Thr Lys Val Glu Ile Lys Arg Thr
            100                 105                 110

<210> SEQ ID NO 22
<211> LENGTH: 110
<212> TYPE: PRT
<213> ORGANISM: Artificial Sequence
<220> FEATURE:
<223> OTHER INFORMATION: Clone SA41F2
<220> FEATURE:
<221> NAME/KEY: DOMAIN
<222> LOCATION: (24)..(35)
<223> OTHER INFORMATION: CDR1
<220> FEATURE:
<221> NAME/KEY: DOMAIN
<222> LOCATION: (51)..(57)
<223> OTHER INFORMATION: CDR2
<220> FEATURE:
<221> NAME/KEY: DOMAIN
<222> LOCATION: (90)..(98)
<223> OTHER INFORMATION: CDR3

<400> SEQUENCE: 22

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser
            20                  25                  30

Ala Leu Ala Trp Tyr Gln Gln Lys Pro Gly Gln Ala Pro Arg Leu Leu
            35                  40                  45
```

-continued

Ile Tyr Gly Ala Ser Ser Arg Ala Thr Gly Val Pro Asp Arg Phe Ser
        50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Ser Ser Thr Pro
                85                  90                  95

Trp Thr Phe Gly Gln Gly Thr Lys Val Glu Ile Lys Arg Thr
                100                 105                 110

<210> SEQ ID NO 23
<211> LENGTH: 110
<212> TYPE: PRT
<213> ORGANISM: Artificial Sequence
<220> FEATURE:
<223> OTHER INFORMATION: Clone SA52B4
<220> FEATURE:
<221> NAME/KEY: DOMAIN
<222> LOCATION: (24)..(35)
<223> OTHER INFORMATION: CDR1
<220> FEATURE:
<221> NAME/KEY: DOMAIN
<222> LOCATION: (51)..(57)
<223> OTHER INFORMATION: CDR2
<220> FEATURE:
<221> NAME/KEY: DOMAIN
<222> LOCATION: (90)..(98)
<223> OTHER INFORMATION: CDR3

<400> SEQUENCE: 23

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
                20                  25                  30

Ala Leu Ala Trp Tyr Gln Gln Lys Pro Gly Gln Ala Pro Arg Leu Leu
            35                  40                  45

Ile Tyr Gly Ala Ser Ser Arg Ala Thr Gly Val Pro Asp Arg Phe Ser
        50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Ser Ser Thr Pro
                85                  90                  95

Trp Thr Phe Gly Gln Gly Thr Lys Val Glu Ile Lys Arg Thr
                100                 105                 110

<210> SEQ ID NO 24
<211> LENGTH: 110
<212> TYPE: PRT
<213> ORGANISM: Artificial Sequence
<220> FEATURE:
<223> OTHER INFORMATION: Clone SA57D4
<220> FEATURE:
<221> NAME/KEY: DOMAIN
<222> LOCATION: (24)..(35)
<223> OTHER INFORMATION: CDR1
<220> FEATURE:
<221> NAME/KEY: DOMAIN
<222> LOCATION: (51)..(57)
<223> OTHER INFORMATION: CDR2
<220> FEATURE:
<221> NAME/KEY: DOMAIN
<222> LOCATION: (90)..(98)
<223> OTHER INFORMATION: CDR3

<400> SEQUENCE: 24

Glu Ile Val Leu Thr Gln Ser Pro Gly Thr Leu Ser Leu Ser Pro Gly

```
                1               5                  10                 15
Glu Arg Ala Thr Leu Ser Cys Arg Ala Ser Gln Ser Val Ser Ser
                20                 25                 30

Ala Leu Ala Trp Tyr Gln Gln Lys Pro Gly Gln Ala Pro Arg Leu Leu
                35                 40                 45

Ile Tyr Gly Ala Ser Ser Arg Ala Thr Gly Val Pro Asp Arg Phe Ser
        50                 55                 60

Gly Ser Gly Ser Gly Thr Asp Phe Thr Leu Thr Ile Ser Arg Leu Glu
65                 70                 75                 80

Pro Glu Asp Phe Ala Val Tyr Tyr Cys Gln Gln Ser Tyr Ser Leu Pro
                85                 90                 95

Trp Thr Phe Gly Gln Gly Thr Lys Val Glu Ile Lys Arg Thr
                100                105                110

<210> SEQ ID NO 25
<211> LENGTH: 110
<212> TYPE: PRT
<213> ORGANISM: Artificial Sequence
<220> FEATURE:
<223> OTHER INFORMATION: Clone SA56D5
<220> FEATURE:
<221> NAME/KEY: DOMAIN
<222> LOCATION: (24)..(35)
<223> OTHER INFORMATION: CDR1
<220> FEATURE:
<221> NAME/KEY: DOMAIN
<222> LOCATION: (51)..(57)
<223> OTHER INFORMATION: CDR2
<220> FEATURE:
<221> NAME/KEY: DOMAIN
<222> LOCATION: (90)..(98)
<223> OTHER INFORMATION: CDR3

<400> SEQUENCE: 25

Glu Ile Val Leu Thr Gln Ser Pro Gly Thr Leu Ser Leu Ser Pro Gly
1               5                  10                 15

Glu Arg Ala Thr Leu Ser Cys Arg Ala Ser Gln Ser Val Ser Ser
                20                 25                 30

Asn Leu Ala Trp Tyr Gln Gln Lys Pro Gly Gln Ala Pro Arg Leu Leu
                35                 40                 45

Ile Tyr Gly Ala Ser Ser Arg Ala Thr Gly Val Pro Asp Arg Phe Ser
        50                 55                 60

Gly Ser Gly Ser Gly Thr Asp Phe Thr Leu Thr Ile Ser Arg Leu Glu
65                 70                 75                 80

Pro Glu Asp Phe Ala Val Tyr Tyr Cys Gln Gln Ser Ser Tyr Pro
                85                 90                 95

Trp Thr Phe Gly Gln Gly Thr Lys Val Glu Ile Lys Arg Thr
                100                105                110

<210> SEQ ID NO 26
<211> LENGTH: 110
<212> TYPE: PRT
<213> ORGANISM: Artificial Sequence
<220> FEATURE:
<223> OTHER INFORMATION: Clone SA57A3
<220> FEATURE:
<221> NAME/KEY: DOMAIN
<222> LOCATION: (24)..(35)
<223> OTHER INFORMATION: CDR1
<220> FEATURE:
<221> NAME/KEY: DOMAIN
<222> LOCATION: (51)..(57)
<223> OTHER INFORMATION: CDR2
<220> FEATURE:
```

<221> NAME/KEY: DOMAIN
<222> LOCATION: (90)..(98)
<223> OTHER INFORMATION: CDR3

<400> SEQUENCE: 26

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Asn Leu Ala Trp Tyr Gln Gln Lys Pro Gly Gln Ala Pro Arg Leu Leu
        35                  40                  45

Ile Tyr Gly Ala Ser Ser Arg Ala Thr Gly Val Pro Asp Arg Phe Ser
50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Ser Ser Ser Tyr Pro
                85                  90                  95

Trp Thr Phe Gly Gln Gly Thr Lys Val Glu Ile Lys Arg Thr
            100                 105                 110

<210> SEQ ID NO 27
<211> LENGTH: 110
<212> TYPE: PRT
<213> ORGANISM: Artificial Sequence
<220> FEATURE:
<223> OTHER INFORMATION: Clone SA60A1
<220> FEATURE:
<221> NAME/KEY: DOMAIN
<222> LOCATION: (24)..(35)
<223> OTHER INFORMATION: CDR1
<220> FEATURE:
<221> NAME/KEY: DOMAIN
<222> LOCATION: (51)..(57)
<223> OTHER INFORMATION: CDR2
<220> FEATURE:
<221> NAME/KEY: DOMAIN
<222> LOCATION: (90)..(98)
<223> OTHER INFORMATION: CDR3

<400> SEQUENCE: 27

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Asn Leu Ala Trp Tyr Gln Gln Lys Pro Gly Gln Ala Pro Arg Leu Leu
        35                  40                  45

Ile Tyr Gly Ala Ser Ser Arg Ala Thr Gly Val Pro Asp Arg Phe Ser
50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Ser Tyr Ser Tyr Pro
                85                  90                  95

Trp Thr Phe Gly Gln Gly Thr Lys Val Glu Ile Lys Arg Thr
            100                 105                 110

<210> SEQ ID NO 28
<211> LENGTH: 110
<212> TYPE: PRT
<213> ORGANISM: Artificial Sequence
<220> FEATURE:
<223> OTHER INFORMATION: Clone SA42A3
<220> FEATURE:
<221> NAME/KEY: DOMAIN
<222> LOCATION: (24)..(35)
<223> OTHER INFORMATION: CDR1
<220> FEATURE:
<221> NAME/KEY: DOMAIN
<222> LOCATION: (51)..(57)
<223> OTHER INFORMATION: CDR2
<220> FEATURE:
<221> NAME/KEY: DOMAIN
<222> LOCATION: (90)..(90)
<223> OTHER INFORMATION: CDR3

<400> SEQUENCE: 28

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Asn Leu Ala Trp Tyr Gln Gln Lys Pro Gly Gln Ala Pro Arg Leu Leu
        35                  40                  45

Ile Tyr Gly Ala Ser Ser Arg Ala Thr Gly Val Pro Asp Arg Phe Ser
50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Ser Ser Ser Tyr Pro
                85                  90                  95

Trp Thr Phe Gly Gln Gly Thr Lys Val Glu Ile Lys Arg Thr
            100                 105                 110

<210> SEQ ID NO 29
<211> LENGTH: 110
<212> TYPE: PRT
<213> ORGANISM: Artificial Sequence
<220> FEATURE:
<223> OTHER INFORMATION: Clone SA44E11
<220> FEATURE:
<221> NAME/KEY: DOMAIN
<222> LOCATION: (24)..(35)
<223> OTHER INFORMATION: CDR1
<220> FEATURE:
<221> NAME/KEY: DOMAIN
<222> LOCATION: (51)..(57)
<223> OTHER INFORMATION: CDR2
<220> FEATURE:
<221> NAME/KEY: DOMAIN
<222> LOCATION: (90)..(98)
<223> OTHER INFORMATION: CDR3

<400> SEQUENCE: 29

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Ala Leu Ala Trp Tyr Gln Gln Lys Pro Gly Gln Ala Pro Arg Leu Leu
        35                  40                  45

Ile Tyr Gly Ala Ser Ser Arg Ala Thr Gly Val Pro Asp Arg Phe Ser
50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Ser Ser Leu Pro
                85                  90                  95

Trp Thr Phe Gly Gln Gly Thr Lys Val Glu Ile Lys Arg Thr
            100                 105                 110

<210> SEQ ID NO 30

<211> LENGTH: 121
<212> TYPE: PRT
<213> ORGANISM: Artificial Sequence
<220> FEATURE:
<223> OTHER INFORMATION: Clone SA51D1
<220> FEATURE:
<221> NAME/KEY: DOMAIN
<222> LOCATION: (31)..(35)
<223> OTHER INFORMATION: CDR1
<220> FEATURE:
<221> NAME/KEY: DOMAIN
<222> LOCATION: (50)..(66)
<223> OTHER INFORMATION: CDR2
<220> FEATURE:
<221> NAME/KEY: DOMAIN
<222> LOCATION: (99)..(110)
<223> OTHER INFORMATION: CDR3

<400> SEQUENCE: 30

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30

Ser Met His Trp Val Arg Gln Ala Pro Gly Lys Gly Leu Glu Trp Val
        35                  40                  45

Ser Glu Ile Thr Pro Tyr Asp Gly Asn Thr Asp Tyr Ala Asp Ser Val
50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Glu Trp Trp Ser Ser Asn Trp Ile Tyr Leu Asp Tyr Trp Gly
            100                 105                 110

Gln Gly Thr Leu Val Thr Val Ser Ser
        115                 120

<210> SEQ ID NO 31
<211> LENGTH: 119
<212> TYPE: PRT
<213> ORGANISM: Artificial Sequence
<220> FEATURE:
<223> OTHER INFORMATION: Clone SA51F6
<220> FEATURE:
<221> NAME/KEY: DOMAIN
<222> LOCATION: (31)..(35)
<223> OTHER INFORMATION: CDR1
<220> FEATURE:
<221> NAME/KEY: DOMAIN
<222> LOCATION: (50)..(66)
<223> OTHER INFORMATION: CDR2
<220> FEATURE:
<221> NAME/KEY: DOMAIN
<222> LOCATION: (99)..(108)
<223> OTHER INFORMATION: CDR3

<400> SEQUENCE: 31

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Asp Tyr
            20                  25                  30

Trp Met His Trp Val Arg Gln Ala Pro Gly Lys Gly Leu Glu Trp Val
        35                  40                  45

Ser Glu Ile Trp Tyr Ser Ser Gly Tyr Thr Asn Tyr Ala Asp Ser Val
50                  55                  60

Lys Gly Arg Phe Thr Ile Ser Arg Asp Asn Ser Lys Asn Thr Leu Tyr

```
                65                  70                  75                  80
Leu Gln Met Asn Ser Leu Arg Ala Glu Asp Thr Ala Val Tyr Tyr Cys
                    85                  90                  95

Ala Arg Asp Ala Phe Pro Trp Asp Val Phe Asp Tyr Trp Gly Gln Gly
                100                 105                 110

Thr Leu Val Thr Val Ser Ser
        115

<210> SEQ ID NO 32
<211> LENGTH: 117
<212> TYPE: PRT
<213> ORGANISM: Artificial Sequence
<220> FEATURE:
<223> OTHER INFORMATION: Clone SA56B8
<220> FEATURE:
<221> NAME/KEY: DOMAIN
<222> LOCATION: (31)..(35)
<223> OTHER INFORMATION: CDR1
<220> FEATURE:
<221> NAME/KEY: DOMAIN
<222> LOCATION: (50)..(66)
<223> OTHER INFORMATION: CDR2
<220> FEATURE:
<221> NAME/KEY: DOMAIN
<222> LOCATION: (99)..(106)
<223> OTHER INFORMATION: CDR3

<400> SEQUENCE: 32

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Asp Tyr
                20                  25                  30

Trp Met His Trp Val Arg Gln Ala Pro Gly Lys Gly Leu Glu Trp Val
            35                  40                  45

Ser Tyr Ile Asn Pro Tyr Gly Gly Tyr Thr Asp Tyr Ala Asp Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                    85                  90                  95

Ala Arg Tyr Val Arg Arg His Phe Asp Tyr Trp Gly Gln Gly Thr Leu
                100                 105                 110

Val Thr Val Ser Ser
        115

<210> SEQ ID NO 33
<211> LENGTH: 120
<212> TYPE: PRT
<213> ORGANISM: Artificial Sequence
<220> FEATURE:
<223> OTHER INFORMATION: Clone SA59G2
<220> FEATURE:
<221> NAME/KEY: DOMAIN
<222> LOCATION: (31)..(35)
<223> OTHER INFORMATION: CDR1
<220> FEATURE:
<221> NAME/KEY: DOMAIN
<222> LOCATION: (51)..(66)
<223> OTHER INFORMATION: CDR2
<220> FEATURE:
<221> NAME/KEY: DOMAIN
<222> LOCATION: (99)..(109)
<223> OTHER INFORMATION: CDR3

<400> SEQUENCE: 33
```

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30

Tyr Met His Trp Val Arg Gln Ala Pro Gly Lys Gly Leu Glu Trp Val
            35                  40                  45

Ser Tyr Ile Asp Pro Val Gly Gly Glu Thr Tyr Tyr Ala Asp Ser Val
50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Tyr Tyr Tyr Trp Gly Tyr Arg Ala Phe Asp Tyr Trp Gly Gln
            100                 105                 110

Gly Thr Leu Val Thr Val Ser Ser
            115                 120

<210> SEQ ID NO 34
<211> LENGTH: 122
<212> TYPE: PRT
<213> ORGANISM: Artificial Sequence
<220> FEATURE:
<223> OTHER INFORMATION: Clone SA56E7
<220> FEATURE:
<221> NAME/KEY: DOMAIN
<222> LOCATION: (31)..(35)
<223> OTHER INFORMATION: CDR1
<220> FEATURE:
<221> NAME/KEY: DOMAIN
<222> LOCATION: (50)..(66)
<223> OTHER INFORMATION: CDR2
<220> FEATURE:
<221> NAME/KEY: DOMAIN
<222> LOCATION: (99)..(111)
<223> OTHER INFORMATION: CDR3

<400> SEQUENCE: 34

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Arg Tyr
            20                  25                  30

Tyr Met His Trp Val Arg Gln Ala Pro Gly Lys Gly Leu Glu Trp Val
            35                  40                  45

Ser Tyr Ile Trp Pro Val Asp Gly Glu Thr Asp Tyr Ala Asp Ser Val
50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Tyr Val Tyr Gly Asn Ser Val Gly Arg Val Phe Asp Tyr Trp
            100                 105                 110

Gly Gln Gly Thr Leu Val Thr Val Ser Ser
            115                 120

<210> SEQ ID NO 35
<211> LENGTH: 122
<212> TYPE: PRT
<213> ORGANISM: Artificial Sequence
<220> FEATURE:
<223> OTHER INFORMATION: Clone SA51D12
<220> FEATURE:
<221> NAME/KEY: DOMAIN

```
<222> LOCATION: (31)..(35)
<223> OTHER INFORMATION: CDR1
<220> FEATURE:
<221> NAME/KEY: DOMAIN
<222> LOCATION: (50)..(66)
<223> OTHER INFORMATION: CDR2
<220> FEATURE:
<221> NAME/KEY: DOMAIN
<222> LOCATION: (99)..(111)
<223> OTHER INFORMATION: CDR3

<400> SEQUENCE: 35
```

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Asp
            20                  25                  30

Val Met His Trp Val Arg Gln Ala Pro Gly Lys Gly Leu Glu Trp Val
        35                  40                  45

Ser Val Ile Ser Gly Tyr Asp Gly Tyr Thr Arg Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Val Pro Tyr Leu Tyr Gly Ala Tyr Ser Phe Asp Tyr Trp
            100                 105                 110

Gly Gln Gly Thr Leu Val Thr Val Ser Ser
            115                 120

```
<210> SEQ ID NO 36
<211> LENGTH: 120
<212> TYPE: PRT
<213> ORGANISM: Artificial Sequence
<220> FEATURE:
<223> OTHER INFORMATION: Clone SA41B5
<220> FEATURE:
<221> NAME/KEY: DOMAIN
<222> LOCATION: (31)..(35)
<223> OTHER INFORMATION: CDR1
<220> FEATURE:
<221> NAME/KEY: DOMAIN
<222> LOCATION: (50)..(66)
<223> OTHER INFORMATION: CDR2
<220> FEATURE:
<221> NAME/KEY: DOMAIN
<222> LOCATION: (99)..(109)
<223> OTHER INFORMATION: CDR3

<400> SEQUENCE: 36
```

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Asp
            20                  25                  30

Val Met His Trp Val Arg Gln Ala Pro Gly Lys Gly Leu Glu Trp Val
        35                  40                  45

Ser Val Ile Asn Pro Tyr Asp Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Ala Val Ala Gly Gln Gly Gly Tyr Phe Asp Tyr Trp Gly Gln
            100                 105                 110

```
Gly Thr Leu Val Thr Val Ser Ser
        115                 120
```

<210> SEQ ID NO 37
<211> LENGTH: 119
<212> TYPE: PRT
<213> ORGANISM: Artificial Sequence
<220> FEATURE:
<223> OTHER INFORMATION: Clone SA32C11
<220> FEATURE:
<221> NAME/KEY: DOMAIN
<222> LOCATION: (31)..(35)
<223> OTHER INFORMATION: CDR1
<220> FEATURE:
<221> NAME/KEY: DOMAIN
<222> LOCATION: (50)..(66)
<223> OTHER INFORMATION: CDR2
<220> FEATURE:
<221> NAME/KEY: DOMAIN
<222> LOCATION: (99)..(108)
<223> OTHER INFORMATION: CDR3

<400> SEQUENCE: 37

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Asp Tyr
            20                  25                  30

Trp Met His Trp Val Arg Gln Ala Pro Gly Lys Gly Leu Glu Trp Val
        35                  40                  45

Ser Glu Ile Asn Thr Ser Asn Gly Asn Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Glu Ser Trp Trp Pro Tyr Ser Phe Asp Tyr Trp Gly Gln Gly
            100                 105                 110

Thr Leu Val Thr Val Ser Ser
        115
```

<210> SEQ ID NO 38
<211> LENGTH: 122
<212> TYPE: PRT
<213> ORGANISM: Artificial Sequence
<220> FEATURE:
<223> OTHER INFORMATION: Clone SA32F1
<220> FEATURE:
<221> NAME/KEY: DOMAIN
<222> LOCATION: (31)..(35)
<223> OTHER INFORMATION: CDR1
<220> FEATURE:
<221> NAME/KEY: DOMAIN
<222> LOCATION: (50)..(66)
<223> OTHER INFORMATION: CDR2
<220> FEATURE:
<221> NAME/KEY: DOMAIN
<222> LOCATION: (99)..(110)
<223> OTHER INFORMATION: CDR3

<400> SEQUENCE: 38

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30

Tyr Met His Trp Val Arg Gln Ala Pro Gly Lys Gly Phe Glu Trp Val
```

```
                35                  40                  45
Ser Ser Ile Ile Thr Asn Gly Gly Glu Thr Asp Tyr Ala Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Leu Pro Val Thr Arg Pro Tyr Tyr Ala Val Phe Asp Tyr Trp
            100                 105                 110

Gly Gln Gly Thr Leu Val Thr Val Ser Ser
            115                 120

<210> SEQ ID NO 39
<211> LENGTH: 119
<212> TYPE: PRT
<213> ORGANISM: Artificial Sequence
<220> FEATURE:
<223> OTHER INFORMATION: Clone SA34G1
<220> FEATURE:
<221> NAME/KEY: DOMAIN
<222> LOCATION: (31)..(35)
<223> OTHER INFORMATION: CDR1
<220> FEATURE:
<221> NAME/KEY: DOMAIN
<222> LOCATION: (50)..(66)
<223> OTHER INFORMATION: CDR2
<220> FEATURE:
<221> NAME/KEY: DOMAIN
<222> LOCATION: (99)..(108)
<223> OTHER INFORMATION: CDR3

<400> SEQUENCE: 39

Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Ser Asp Tyr
                 20                  25                  30

Trp Met His Trp Val Arg Gln Ala Pro Gly Lys Gly Leu Glu Trp Val
             35                  40                  45

Ser Glu Ile Ile Pro Tyr Ser Gly Tyr Thr Asn Tyr Ala Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Glu Thr Trp Gly Tyr Pro Ser Phe Asp Tyr Trp Gly Gln Gly
            100                 105                 110

Thr Leu Val Thr Val Ser Ser
            115

<210> SEQ ID NO 40
<211> LENGTH: 125
<212> TYPE: PRT
<213> ORGANISM: Artificial Sequence
<220> FEATURE:
<223> OTHER INFORMATION: Clone SA42E10
<220> FEATURE:
<221> NAME/KEY: DOMAIN
<222> LOCATION: (31)..(35)
<223> OTHER INFORMATION: CDR1
<220> FEATURE:
<221> NAME/KEY: DOMAIN
<222> LOCATION: (50)..(66)
<223> OTHER INFORMATION: CDR2
<220> FEATURE:
```

```
<221> NAME/KEY: DOMAIN
<222> LOCATION: (99)..(114)
<223> OTHER INFORMATION: CDR3

<400> SEQUENCE: 40
```

| | | | | | | | | | | | | | | |
|---|---|---|---|---|---|---|---|---|---|---|---|---|---|---|
| Glu | Val | Gln | Leu | Leu | Glu | Ser | Gly | Gly | Gly | Leu | Val | Gln | Pro | Gly | Gly |
| 1 | | | | 5 | | | | | 10 | | | | | 15 |

Ser Leu Arg Leu Ser Cys Ala Ala Ser Gly Phe Thr Phe Ser Asp Tyr
            20                  25                  30

Ala Met His Trp Val Arg Gln Ala Pro Gly Lys Gly Leu Glu Trp Val
        35                  40                  45

Ser Ser Ile Ile Pro Tyr Thr Gly Thr Thr Asp Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Thr Asp Asp Leu Ile Gly His Tyr Asp Val Tyr Tyr Tyr Phe
            100                 105                 110

Asp Tyr Trp Gly Gln Gly Thr Leu Val Thr Val Ser Ser
        115                 120                 125

```
<210> SEQ ID NO 41
<211> LENGTH: 118
<212> TYPE: PRT
<213> ORGANISM: Artificial Sequence
<220> FEATURE:
<223> OTHER INFORMATION: Clone SA52C2
<220> FEATURE:
<221> NAME/KEY: DOMAIN
<222> LOCATION: (31)..(35)
<223> OTHER INFORMATION: CDR1
<220> FEATURE:
<221> NAME/KEY: DOMAIN
<222> LOCATION: (50)..(66)
<223> OTHER INFORMATION: CDR2
<220> FEATURE:
<221> NAME/KEY: DOMAIN
<222> LOCATION: (99)..(107)
<223> OTHER INFORMATION: CDR3

<400> SEQUENCE: 41
```

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Asp
            20                  25                  30

Val Met His Trp Val Arg Gln Ala Pro Gly Lys Gly Leu Glu Trp Val
        35                  40                  45

Ser Glu Ile Asp Pro Ser Asp Gly Thr Thr Asn Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Ser Tyr Leu Asp Trp Pro Leu Asp Val Trp Gly Gln Gly Thr
            100                 105                 110

Leu Val Thr Val Ser Ser
        115

```
<210> SEQ ID NO 42
<211> LENGTH: 121
```

```
<212> TYPE: PRT
<213> ORGANISM: Artificial Sequence
<220> FEATURE:
<223> OTHER INFORMATION: Clone SA55D1
<220> FEATURE:
<221> NAME/KEY: DOMAIN
<222> LOCATION: (31)..(35)
<223> OTHER INFORMATION: CDR1
<220> FEATURE:
<221> NAME/KEY: DOMAIN
<222> LOCATION: (50)..(66)
<223> OTHER INFORMATION: CDR2
<220> FEATURE:
<221> NAME/KEY: DOMAIN
<222> LOCATION: (99)..(110)
<223> OTHER INFORMATION: CDR3

<400> SEQUENCE: 42

Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Ser Ser Asp
            20                  25                  30

Val Met His Trp Val Arg Gln Ala Pro Gly Lys Gly Leu Glu Trp Val
        35                  40                  45

Ser Val Ile Ser Pro Tyr Asp Gly Tyr Thr Arg Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg His Lys Gly Gly Tyr Arg Ala Tyr Met Asp Tyr Trp Gly
            100                 105                 110

Gln Gly Thr Leu Val Thr Val Ser Ser
        115                 120

<210> SEQ ID NO 43
<211> LENGTH: 119
<212> TYPE: PRT
<213> ORGANISM: Artificial Sequence
<220> FEATURE:
<223> OTHER INFORMATION: Clone SA51H4
<220> FEATURE:
<221> NAME/KEY: DOMAIN
<222> LOCATION: (31)..(35)
<223> OTHER INFORMATION: CDR1
<220> FEATURE:
<221> NAME/KEY: DOMAIN
<222> LOCATION: (50)..(66)
<223> OTHER INFORMATION: CDR2
<220> FEATURE:
<221> NAME/KEY: DOMAIN
<222> LOCATION: (99)..(108)
<223> OTHER INFORMATION: CDR3

<400> SEQUENCE: 43

Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Ser Asp Tyr
            20                  25                  30

Trp Met His Trp Val Arg Gln Ala Pro Gly Lys Gly Leu Glu Trp Val
        35                  40                  45

Ser Glu Ile Trp Pro Tyr Asp Gly Tyr Thr Asn Tyr Ala Asp Ser Val
    50                  55                  60

Lys Gly Arg Phe Thr Ile Ser Arg Asp Asn Ser Lys Asn Thr Leu Tyr
65                  70                  75                  80
```

Leu Gln Met Asn Ser Leu Arg Ala Glu Asp Thr Ala Val Tyr Tyr Cys
                85                  90                  95

Ala Arg Asp Pro Gly Pro Glu Gly Val Phe Asp Tyr Trp Gly Gln Gly
            100                 105                 110

Thr Leu Val Thr Val Ser Ser
        115

<210> SEQ ID NO 44
<211> LENGTH: 119
<212> TYPE: PRT
<213> ORGANISM: Artificial Sequence
<220> FEATURE:
<223> OTHER INFORMATION: Clone SA41A5
<220> FEATURE:
<221> NAME/KEY: DOMAIN
<222> LOCATION: (31)..(35)
<223> OTHER INFORMATION: CDR1
<220> FEATURE:
<221> NAME/KEY: DOMAIN
<222> LOCATION: (50)..(66)
<223> OTHER INFORMATION: CDR2
<220> FEATURE:
<221> NAME/KEY: DOMAIN
<222> LOCATION: (99)..(108)
<223> OTHER INFORMATION: CDR3

<400> SEQUENCE: 44

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30

Tyr Met His Trp Val Arg Gln Ala Pro Gly Lys Gly Leu Glu Trp Val
        35                  40                  45

Ser Glu Ile Asn Tyr Asp Gly Glu Thr Asp Tyr Ala Asp Ser Val Lys
    50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Arg Asp Gly Phe Trp Tyr Gly Thr Ala Phe Asp Tyr Trp Gly Gln Gly
            100                 105                 110

Thr Leu Val Thr Val Ser Ser
        115

<210> SEQ ID NO 45
<211> LENGTH: 121
<212> TYPE: PRT
<213> ORGANISM: Artificial Sequence
<220> FEATURE:
<223> OTHER INFORMATION: Clone SA58A12
<220> FEATURE:
<221> NAME/KEY: DOMAIN
<222> LOCATION: (31)..(35)
<223> OTHER INFORMATION: CDR1
<220> FEATURE:
<221> NAME/KEY: DOMAIN
<222> LOCATION: (50)..(65)
<223> OTHER INFORMATION: CDR2
<220> FEATURE:
<221> NAME/KEY: DOMAIN
<222> LOCATION: (98)..(110)
<223> OTHER INFORMATION: CDR3

<400> SEQUENCE: 45

Glu Val Gln Leu Leu Glu Ser Gly Gly Gly Leu Val Gln Pro Gly Gly

```
                1               5                   10                  15
Ser Leu Arg Leu Ser Cys Ala Ala Ser Gly Phe Thr Phe Ser Asn Tyr
            20                  25                  30

Gly Met His Trp Val Arg Gln Ala Pro Gly Lys Gly Leu Glu Trp Val
            35                  40                  45

Ser Glu Ile Trp Pro Asn Asn Gly Thr Thr Asn Tyr Ala Asp Ser Val
    50                  55                  60

Lys Gly Arg Phe Thr Ile Ser Arg Asp Asn Ser Lys Asn Thr Leu Tyr
65                      70                  75                  80

Leu Gln Met Asn Ser Leu Arg Ala Glu Asp Thr Ala Val Tyr Tyr Cys
                    85                  90                  95

Ala Arg Glu Ser Gly Gln Trp Trp Tyr Gly Val Phe Asp Tyr Trp Gly
                100                 105                 110

Gln Gly Thr Leu Val Thr Val Ser Ser
            115                 120

<210> SEQ ID NO 46
<211> LENGTH: 123
<212> TYPE: PRT
<213> ORGANISM: Artificial Sequence
<220> FEATURE:
<223> OTHER INFORMATION: Clone SA33D5
<220> FEATURE:
<221> NAME/KEY: DOMAIN
<222> LOCATION: (31)..(35)
<223> OTHER INFORMATION: CDR1
<220> FEATURE:
<221> NAME/KEY: DOMAIN
<222> LOCATION: (50)..(66)
<223> OTHER INFORMATION: CDR2
<220> FEATURE:
<221> NAME/KEY: DOMAIN
<222> LOCATION: (99)..(112)
<223> OTHER INFORMATION: CDR3

<400> SEQUENCE: 46

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Asp
            20                  25                  30

Val Met His Trp Val Arg Gln Ala Pro Gly Lys Gly Leu Glu Trp Val
            35                  40                  45

Ser Glu Ile Asp Pro Asn Asp Gly Ser Thr Arg Tyr Ala Asp Ser Val
    50                  55                  60

Lys Gly Arg Phe Thr Ile Ser Arg Asp Asn Ser Lys Asn Thr Leu Tyr
65                      70                  75                  80

Leu Gln Met Asn Ser Leu Arg Ala Glu Asp Thr Ala Val Tyr Tyr Cys
                    85                  90                  95

Ala Arg Glu Tyr Gly Ala Val Ser Trp Ser Val Val Phe Asp Tyr
                100                 105                 110

Trp Gly Gln Gly Thr Leu Val Thr Val Ser Ser
            115                 120

<210> SEQ ID NO 47
<211> LENGTH: 121
<212> TYPE: PRT
<213> ORGANISM: Artificial Sequence
<220> FEATURE:
<223> OTHER INFORMATION: Clone SA41F2
<220> FEATURE:
<221> NAME/KEY: DOMAIN
<222> LOCATION: (31)..(35)
```

```
<223> OTHER INFORMATION: CDR1
<220> FEATURE:
<221> NAME/KEY: DOMAIN
<222> LOCATION: (50)..(66)
<223> OTHER INFORMATION: CDR2
<220> FEATURE:
<221> NAME/KEY: DOMAIN
<222> LOCATION: (99)..(110)
<223> OTHER INFORMATION: CDR3

<400> SEQUENCE: 47
```

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30

Gly Met His Trp Val Arg Gln Ala Pro Gly Lys Gly Leu Glu Trp Val
        35                  40                  45

Ser Glu Ile Asp Tyr Val Asp Gly Asn Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Glu Val Tyr Ala His Gly Ile Ala Ala Phe Asp Tyr Trp Gly
            100                 105                 110

Gln Gly Thr Leu Val Thr Val Ser Ser
            115                 120

```
<210> SEQ ID NO 48
<211> LENGTH: 121
<212> TYPE: PRT
<213> ORGANISM: Artificial Sequence
<220> FEATURE:
<223> OTHER INFORMATION: Clone SA52B4
<220> FEATURE:
<221> NAME/KEY: DISULFID
<222> LOCATION: (31)..(35)
<223> OTHER INFORMATION: CDR1
<220> FEATURE:
<221> NAME/KEY: DISULFID
<222> LOCATION: (50)..(66)
<223> OTHER INFORMATION: CDR2
<220> FEATURE:
<221> NAME/KEY: DISULFID
<222> LOCATION: (99)..(110)
<223> OTHER INFORMATION: CDR3

<400> SEQUENCE: 48
```

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Asp Tyr
            20                  25                  30

Ser Met His Trp Val Arg Gln Ala Pro Gly Lys Gly Leu Glu Trp Val
        35                  40                  45

Ser Glu Ile Trp Thr Asn Thr Gly Tyr Thr Asn Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Glu Ser Trp Gly Trp Phe Ser Ile Val Phe Asp Tyr Trp Gly
            100                 105                 110

Gln Gly Thr Leu Val Thr Val Ser Ser
        115                 120

<210> SEQ ID NO 49
<211> LENGTH: 117
<212> TYPE: PRT
<213> ORGANISM: Artificial Sequence
<220> FEATURE:
<223> OTHER INFORMATION: Clone SA57D4
<220> FEATURE:
<221> NAME/KEY: DOMAIN
<222> LOCATION: (31)..(35)
<223> OTHER INFORMATION: CDR1
<220> FEATURE:
<221> NAME/KEY: DOMAIN
<222> LOCATION: (50)..(66)
<223> OTHER INFORMATION: CDR2
<220> FEATURE:
<221> NAME/KEY: DOMAIN
<222> LOCATION: (99)..(106)
<223> OTHER INFORMATION: CDR3

<400> SEQUENCE: 49

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Gly Tyr
            20                  25                  30

Gly Met His Trp Val Arg Gln Ala Pro Gly Lys Gly Leu Glu Trp Val
        35                  40                  45

Ser Ala Ile Ser Asp Leu Asn Gly Ser Thr Tyr Tyr Ala Asp Ser Val
    50                  55                  60

Lys Gly Arg Phe Thr Ile Ser Arg Asp Asn Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asn Gly Trp Gly Asp Met Asp Leu Trp Gly Gln Gly Thr Leu
            100                 105                 110

Val Thr Val Ser Ser
        115

<210> SEQ ID NO 50
<211> LENGTH: 123
<212> TYPE: PRT
<213> ORGANISM: Artificial Sequence
<220> FEATURE:
<223> OTHER INFORMATION: Clone SA56D5
<220> FEATURE:
<221> NAME/KEY: DOMAIN
<222> LOCATION: (31)..(35)
<223> OTHER INFORMATION: CDR1
<220> FEATURE:
<221> NAME/KEY: DOMAIN
<222> LOCATION: (50)..(66)
<223> OTHER INFORMATION: CDR2
<220> FEATURE:
<221> NAME/KEY: DOMAIN
<222> LOCATION: (99)..(112)
<223> OTHER INFORMATION: CDR3

<400> SEQUENCE: 50

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Asp Tyr
            20                  25                  30

Tyr Met His Trp Val Arg Gln Ala Pro Gly Lys Gly Leu Glu Trp Val
        35                  40                  45

Ser Tyr Ile Asp Gly Asn Gly Gly Tyr Thr Asp Tyr Ala Asp Ser Val
    50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                85                  90                  95

Ala Arg Tyr Trp Phe Asp Ser Ser Tyr Lys His Arg Tyr Phe Asp Tyr
            100                 105                 110

Trp Gly Gln Gly Thr Leu Val Thr Val Ser Ser
            115                 120

<210> SEQ ID NO 51
<211> LENGTH: 122
<212> TYPE: PRT
<213> ORGANISM: Artificial Sequence
<220> FEATURE:
<223> OTHER INFORMATION: Clone SA57A3
<220> FEATURE:
<221> NAME/KEY: DOMAIN
<222> LOCATION: (31)..(35)
<223> OTHER INFORMATION: CDR1
<220> FEATURE:
<221> NAME/KEY: DOMAIN
<222> LOCATION: (50)..(66)
<223> OTHER INFORMATION: CDR2
<220> FEATURE:
<221> NAME/KEY: DOMAIN
<222> LOCATION: (99)..(111)
<223> OTHER INFORMATION: CDR3

<400> SEQUENCE: 51

Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Ser Asp Tyr
                20                  25                  30

Tyr Met His Trp Val Arg Gln Ala Pro Gly Lys Gly Leu Glu Trp Val
            35                  40                  45

Ser Tyr Ile Asn Thr Tyr Asp Gly Asn Thr Asp Tyr Ala Asp Ser Val
    50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                85                  90                  95

Ala Arg Tyr Tyr Asn Pro Tyr Thr Arg Arg Arg Val Phe Asp Tyr Trp
            100                 105                 110

Gly Gln Gly Thr Leu Val Thr Val Ser Ser
            115                 120

<210> SEQ ID NO 52
<211> LENGTH: 123
<212> TYPE: PRT
<213> ORGANISM: Artificial Sequence
<220> FEATURE:
<223> OTHER INFORMATION: Clone SA60A1
<220> FEATURE:
<221> NAME/KEY: DOMAIN
<222> LOCATION: (31)..(35)
<223> OTHER INFORMATION: CDR1
<220> FEATURE:
<221> NAME/KEY: DOMAIN
<222> LOCATION: (50)..(66)
<223> OTHER INFORMATION: CDR2
<220> FEATURE:
<221> NAME/KEY: DOMAIN

```
<222> LOCATION: (99)..(112)
<223> OTHER INFORMATION: CDR3

<400> SEQUENCE: 52
```

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Pro Tyr
            20                  25                  30

Tyr Met His Trp Val Arg Gln Ala Pro Gly Lys Gly Leu Glu Trp Val
        35                  40                  45

Ser Tyr Ile Thr Pro Tyr Asp Gly Tyr Thr Asp Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Tyr Ser Tyr Val Gly Ser Val Arg Thr Arg Val Phe Asp Tyr
            100                 105                 110

Trp Gly Gln Gly Thr Leu Val Thr Val Ser Ser
            115                 120

```
<210> SEQ ID NO 53
<211> LENGTH: 115
<212> TYPE: PRT
<213> ORGANISM: Artificial Sequence
<220> FEATURE:
<223> OTHER INFORMATION: Clone SA42A3
<220> FEATURE:
<221> NAME/KEY: DOMAIN
<222> LOCATION: (31)..(35)
<223> OTHER INFORMATION: CDR1
<220> FEATURE:
<221> NAME/KEY: DOMAIN
<222> LOCATION: (50)..(66)
<223> OTHER INFORMATION: CDR2
<220> FEATURE:
<221> NAME/KEY: DOMAIN
<222> LOCATION: (99)..(104)
<223> OTHER INFORMATION: CDR3

<400> SEQUENCE: 53
```

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30

Ser Met His Trp Val Arg Gln Ala Pro Gly Lys Gly Leu Glu Trp Val
        35                  40                  45

Ser Ser Ile Tyr Tyr Asp Gly Glu Thr Asp Tyr Ala Asp Ser Val Lys
    50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Arg Ser Asp Gly Asp Val Asp Tyr Trp Gly Gln Gly Thr Leu Val Thr
            100                 105                 110

Val Ser Ser
        115

```
<210> SEQ ID NO 54
<211> LENGTH: 116
<212> TYPE: PRT
```

```
<213> ORGANISM: Artificial Sequence
<220> FEATURE:
<223> OTHER INFORMATION: Clone SA44E11
<220> FEATURE:
<221> NAME/KEY: DOMAIN
<222> LOCATION: (31)..(35)
<223> OTHER INFORMATION: CDR1
<220> FEATURE:
<221> NAME/KEY: DOMAIN
<222> LOCATION: (50)..(66)
<223> OTHER INFORMATION: CDR2
<220> FEATURE:
<221> NAME/KEY: DOMAIN
<222> LOCATION: (99)..(105)
<223> OTHER INFORMATION: CDR3

<400> SEQUENCE: 54

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Asp Tyr
            20                  25                  30

Tyr Met His Trp Val Arg Gln Ala Pro Gly Lys Gly Leu Glu Trp Val
        35                  40                  45

Ser Glu Ile Ser Thr Tyr Asn Gly Tyr Thr Asp Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Gly Glu Pro Gly Asp Asp Trp Gly Gln Gly Thr Leu Val
            100                 105                 110

Thr Val Ser Ser
            115
```